United States Patent
Araki et al.

(10) Patent No.: US 6,762,197 B2
(45) Date of Patent: Jul. 13, 2004

(54) DIFLUOROMETHYLTRIAZOLONE COMPOUNDS, USE OF THE SAME AND INTERMEDIATES FOR THE PRODUCTION THEREOF

(75) Inventors: Tomohiro Araki, Toyonaka (JP); Yoshiharu Kinoshita, Toyonaka (JP); Hiroshi Sakaguchi, Toyonaka (JP); Akio Manabe, Sanda (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/149,034

(22) PCT Filed: Dec. 1, 2000

(86) PCT No.: PCT/JP00/08558

§ 371 (c)(1),
(2), (4) Date: Jun. 6, 2002

(87) PCT Pub. No.: WO01/42227

PCT Pub. Date: Jun. 14, 2001

(65) Prior Publication Data

US 2003/0119670 A1 Jun. 26, 2003

(30) Foreign Application Priority Data

| Dec. 8, 1999 | (JP) | ............................................. 11-348884 |
| Apr. 12, 2000 | (JP) | ....................................... 2000-110682 |
| Jun. 1, 2000 | (JP) | ....................................... 2000-164223 |
| Aug. 9, 2000 | (JP) | ....................................... 2000-240866 |

(51) Int. Cl.[7] .................. C07D 249/14; C07D 401/10; C07D 403/10; A01N 43/653

(52) U.S. Cl. ........................ 514/359; 514/336; 514/344; 514/345; 514/256; 514/269; 548/263.2; 546/272.4; 544/310; 544/315; 544/319

(58) Field of Search .................... 548/263.2; 546/272.4; 544/310, 315, 319; 514/336, 344, 345, 359, 256, 269

(56) References Cited

U.S. PATENT DOCUMENTS

| 4,473,709 A | 9/1984 | Montgomery et al. |
| 5,475,115 A | 12/1995 | Linker et al. |
| 5,508,420 A | 4/1996 | Haas et al. |

FOREIGN PATENT DOCUMENTS

| DE | 198 34 557 A1 | 7/1998 |
| EP | 1 010 690 A1 | 6/2000 |
| EP | 1 103 548 A1 | 5/2001 |
| JP | 10-45754 A | 2/1998 |
| WO | 94/24116 A1 | 10/1994 |
| WO | 99/07687 A1 | 2/1999 |

Primary Examiner—Venkataraman Balasubramanian
(74) Attorney, Agent, or Firm—Sughrue Mion, PLLC

(57) ABSTRACT

A triazolone compound of the formula [I]:

[I]

(structure: R$^1$—T—CH$_2$ attached to N of triazolone ring bearing F$_2$HC substituent, =O, and N—CH$_3$)

wherein;
R$^1$ represents optionally substituted phenyl or the like, T represents m-phenylene optionally substituted by methyl or the like;
and a fungicidal composition containing it as an active ingredient.

9 Claims, No Drawings

DIFLUOROMETHYLTRIAZOLONE COMPOUNDS, USE OF THE SAME AND INTERMEDIATES FOR THE PRODUCTION THEREOF

TECHNICAL FIELD

The present invention relates to triazolone compounds, use thereof and production intermediates thereof.

BACKGROUND ART

WO99/07687 describes that a certain kind of triazolone compounds has a fungicidal activity.

DISCLOSURE OF THE INVENTION

The present invention provides compounds having a fungicidal activity, particularly an excellent fungicidal activity on fungi causing plant diseases and useful for controlling plant diseases.

Namely, the present invention provides a triazolone compound of the formula [I] (hereinafter, referred to as the compound of the invention):

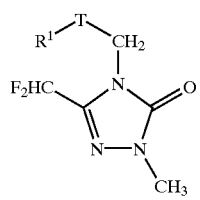

wherein, $R^1$ represents a $A^1$-$L^1$-, $A^1$-ON=$CA^2$—, $A^1$-ON=C(Me) $CH_2ON=CA^2$—, $A^1$-C($A^2$)=N—$OCH_2$—, $A^1S$—C($A^2$)=N—, $A^1$-C(=S)NH—, $A^1S$—C(=S)NH—, $A^1S$—C($SA^2$)=N—, $A^1$-ON=C(CN)—, $A^1$-ON=C(Me)$CH_2ON$=C(CN)—, $A^1$-C(CN)=N—$OCH_2$—, halogen atom, nitro or cyano;

wherein, $L^1$ represents single bond, oxygen atom, sulfur atom, carbonyl, —$OCH_2$—, —$SCH_2$—, —C(=O)O—, —OC(=O)—, —C(=O)$OCH_2$—, —NH— or $C_1$-$C_6$ alkylimino;

$A^1$ and $A^2$, which are the same or different, represent hydrogen atom, $C_1$-$C_{10}$ alkyl, $C_2$-$C_{10}$ alkenyl, $C_2$-$C_{10}$ alkynyl, $C_3$-$C_{10}$ cycloalkyl, ($C_3$-$C_{10}$ cycloalkyl) $C_1$-$C_{10}$ alkyl, $C_5$-$C_{10}$ cycloalkenyl, ($C_5$-$C_{10}$ cycloalkenyl) $C_1$-$C_{10}$ alkyl, phenyl, naphthyl, phenyl $C_1$-$C_{10}$ alkyl, naphtyl $C_1$-$C_{10}$ alkyl, 5- or 6-membered heterocyclic group optionally condensed with a benzene ring, or methyl substituted by 5- or 6-membered heterocyclic group optionally condensed with a benzene ring;

the alkyl, the alkenyl, the alkynyl, the cycloalkyl, the cycloalkylalkyl, the cycloalkenyl and the cycloalkenylalkyl, represented by $A^1$ and $A^2$, may optionally be each substituted by one or more substituents selected from the group consisting of halogen atom(s), cyano, nitro, $C_1$-$C_{10}$ alkoxy, $C_1$-$C_{10}$ haloalkoxy, $C_1$-$C_{10}$ alkylthio, $C_1$-$C_{10}$ haloalkylthio, ($C_1$-$C_9$ alkyl)carbonyl, ($C_1$-$C_9$ alkoxy)carbonyl, ($C_1$-$C_9$ alkyl)carbonylamino, phenyl, phenoxy, benzyloxy and tri($C_1$-$C_{10}$ alkyl)silyl;

the phenyl, the naphthyl, the benzene ring in the phenylalkyl, the naphthalene ring in the phenylnaphthyl, the heterocyclic group, and the heterocyclic ring in the methyl substituted by heterocylic group, represented by $A^1$ and $A^2$, may optionally be each substituted by one or more substituents selected from the group consisting of halogen atom(s), cyano, nitro, $C_1$-$C_{10}$ alkyl, $C_1$-$C_{10}$ haloalkyl, $C_3$-$C_{10}$ cycloalkyl, $C_1$-$C_{10}$ alkoxy, $C_1$-$C_{10}$ haloalkoxy, $C_1$-$C_{10}$ alkylthio, $C_1$-$C_{10}$ haloalkylthio, ($C_1$-$C_9$ alkyl)carbonyl, ($C_1$-$C_9$ alkoxy)carbonyl, ($C_1$-$C_9$ alkyl)carbonylamino, phenyl, phenoxy, benzyloxy, tri($C_1$-$C_{10}$ alkyl)silyl, methylenedioxy and difluoromethylenedioxy;

with the proviso, when $L^1$ is single bond, $A^1$ is not a hydrogen atom;

T represents optionally substituted m-phenylene, optionally substituted m-azaphenylene (m-pyridinediyl) or optionally substituted m-diazaphenylene (m-diazinediyl, namely, m-pyridazinediyl, m-pyrimidinediyl or m-pyrazinediyl) bonded to $R^1$ and to $CH_2$ each via a carbon atom;

wherein the substituents are one or more substituents selected from the group consisting of halogen atoms, cyano, nitro, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio and ($C_1$-$C_5$ alkoxy)carbonyl;

and a fungicidal composition containing this compound as an active ingredient.

The present invention provides also 5-difluoromethyl-2-methyl-2,4-dihydro-3H-1,2,4-triazol-3-one of the formula [L]:

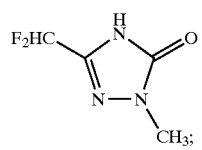

a difluoroacetyl semicarbazide compound of the formula [XXVI]:

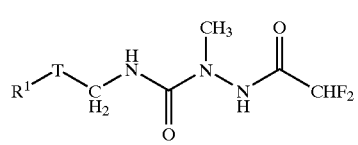

wherein $R^1$ and T have the same meanings as described above; a semicarbazide compound of the formula [VII]:

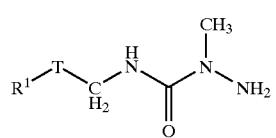

wherein $R^1$ and T have the same meanings as described above; 2-methyl-5-phenylbenzylamine of the formula [XVI-1]:

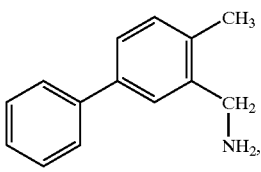

[XVI-1]

inorganic acid salt (for example, hydrochloric acid addition salt, hydrobromic acid addition salt, sulfuric acid addition salt) and sulfonic acid salt (for example, methanesulfonic acid addition salt) of 2-methyl-5-phenylbenzylamine; 2-methyl-5-phenylbenzyl chloride of the formula [XIII-1]:

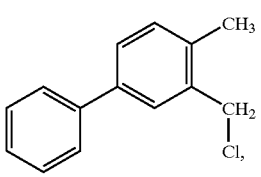

[XIII-1]

a sulfonate compounds of the formula [XIII-2]:

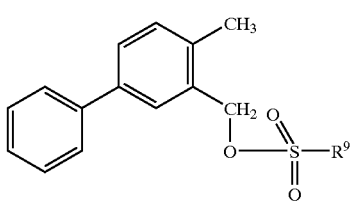

[XIII-2]

wherein $R^9$ represents a methyl or p-tolyl; N,N-dimethyl-(2-methyl-5-phenylbenzyl)amine of the formula [LI]:

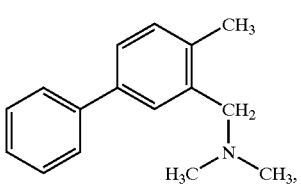

[LI]

inorganic acid salt (for example, hydrochloric acid addition salt, hydrobromic acid addition salt, sulfuric acid addition salt) and sulfonic acid salt (for example, methanesulfonic acid addition salt) of N,N-dimethyl-(2-methyl-5-phenylbenzyl)-amine, useful as a production intermediate for a compound of the invention.

In the present invention; as the $C_1$–$C_{10}$ alkyl represented by $A^1$ and $A^2$, for example, methyl, ethyl, propyl, isopropyl, butyl, isobutyl, 1-methylpropyl, pentyl, 1-methylbutyl, 1-ethylbutyl, 2-methylbutyl, 3-methylbutyl, 2,2-dimethylpropyl, 1,2-dimethylpropyl, 1,1-dimethylpropyl, hexyl, 1-methylpentyl, 1-ethylpentyl, 3,3-dimethylbutyl, heptyl, 3,7-dimethyloctyl and the like are listed; as the $C_2$–$C_{10}$ alkenyl represented by $A^1$ and $A^2$, for example, vinyl, allyl, 1-methyl-2-propenyl, 2-methyl-2-propenyl, 2-butenyl, 2-pentenyl, 3-methyl-2-butenyl and the like are listed; as the $C_2$–$C_{10}$ alkynyl represented by $A^1$ and $A^2$, for example, ethynyl, proparqyl, 1-methyl-2-propynyl, 2-butynyl and the like are listed; as the $C_3$–$C_{10}$ cycloalkyl represented by $A^1$ and $A^2$, for example, cyclopropyl, cyclopentyl, cyclohexyl and the like are listed; as the ($C_3$–$C_{10}$ cycloalkyl)alkyl represented by $A^1$ and $A^2$, for example, cyclopropylmethyl, cyclopentylmethyl, 2-cyclopentylethyl, cyclohexylmethyl and the like are listed; as the $C_5$–$C_{10}$ cycloalkenyl represented by $A^1$ and $A^2$, for example, cyclopentenyl, cyclohexenyl and the like are listed; as the ($C_5$–$C_{10}$ cycloalkenyl)alkyl represented by $A^1$ and $A^2$, for example, cyclopenten-1-ylmethyl, cyclohexen-1-ylmethyl and the like are listed; as the phenyl $C_1$–$C_{10}$ alkyl represented by $A^1$ and $A^2$, for example, phenylmethyl, 2-phenylethyl, 3-phenylpropyl, 4-phenylbutyl and the like are listed; as the naphthyl $C_1$–$C_{10}$ alkyl represented by $A^1$ and $A^2$, for example, α-naphthylmethyl, β-naphthylmethyl and the like are listed; as the 5- or 6-membered heterocyclic group optionally condensed with a benzene ring represented by $A^1$ and $A^2$, for example, 2-pyridyl, 3-pyridyl, 4-pyridyl, 2-pyrimidinyl, 4-pyrimidinyl, 5-pyrimidinyl, 2-pyrazinyl, 3-pyridazinyl, 4-pyridazinyl, 2-thienyl, 3-thienyl, 2-furyl, 3-furyl, pyrrol-1-yl, pyrrol-2-yl, pyrrol-3-yl, 1-pyrazolyl, 3-pyrazolyl, 4-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isooxazolyl, 4-isooxazolyl, 5-isooxazolyl, 1-imidazolyl, 2-imidazolyl, 4-imidazolyl, 5-imidazolyl, 1-(1,2,4-triazolyl), 3-(1,2,4-triazolyl), 4-(1,2,4-triazolyl), 2-benzothienyl, 3-benzothienyl, benzothiazol-2-yl, 2-quinolyl and the like are listed; and as the methyl substituted by a 5- or 6-membered heterocyclic group optionally condensed with a benzene ring represented by $A^1$ and $A^2$, for example, 2-eyridylmethyl, 4-pyridylmethyl, 2-pyrimidinylmethyl, 4-pyrimidinylmethyl, 3-pyrazolylmethyl, 2-thiazolylmethyl, 2-imidazolylmethyl, 3-(1,2,4-triazolyl)methyl, 2-quinolylmethyl and the like are listed.

Here, the alkyl, the alkenyl, the alkynyl, the cycloalkyl, the cycloalkylalkyl, the cycloalkenyl and the cycloalkenylalkyl represented by $A^1$ and $A^2$ may optionally be each substituted by one or more substituents selected from the group consisting of halogen atom(s) (fluorine atom, chlorine atom, bromine atom, iodine atom), cyano, nitro, $C_1$–$C_{10}$ alkoxy, $C_1$–$C_{10}$ haloalkoxy, $C_1$–$C_{10}$ alkylthio, $C_1$–$C_{10}$ haloalkylthio, ($C_1$–$C_9$ alkyl)carbonyl, ($C_1$–$C_9$ alkoxy)carbonyl, ($C_1$–$C_9$ alkyl)carbonylamino, phenyl, phenoxy, benzyloxy and tri($C_1$–$C_{10}$ alkyl)silyl; and as the alkoxy, for example, a methoxy, ethoxy, propoxy, isopropoxy, butoxy, sec-butoxy, isobutoxy, pentyloxy and the like are listed; as the haloalkoxy, for example, a trifluoromethoxy, difluoromethoxy, bromodifluoromethoxy, chlorodifluoromethoxy, fluoromethoxy, 2,2,2-trifluoroethoxy, 1,1,2,2-tetrafluoroethoxy and the like are listed; as the alkylthio, for example, a methylthio, ethylthio, propylthio, butylthio, isobutylthio, sec-butylthio, pentylthio, hexylthio and the like are listed, as the haloalkylthio, for example, a trifluoromethylthio, difluoromethylthio, bromodifluoromethylthio, chlorodifluoromethylthio, fluoromethylthio, 2,2,2-trifluoroethylthio, 1,1,2,2-tetrafluoroethylthio and the like are listed; as the alkylcarbonyl, for example, an acetyl, propanoyl, butanoyl, 3-methylbutanoyl andthe like are listed; as the alkoxycarbonyl, for example, a methoxycarbonyl, ethoxycarbonyl, propoxycarbonyl, isopropoxycarbonyl, butoxycarbonyl, isobutoxycarbonyl, sec-butoxycarbonyl, pentyloxycarbonyl, hexyloxycarbonyl and the like are listed; as the alkylcarbonylamino, for example, an acetylamino, propanylamino, butanoylamino, 3-methylbutanoylamino and the like; and as the $C_3$–$C_{20}$ trialkylsilyl, for example, a trimethylsilyl, triethylsilyl and the like are listed.

Further, the phenyl, the naphthyl, the benzene ring in the phenylalkyl, the naphthalene ring in the phenylnaphthyl, the heterocyclic group, and the heterocyclic ring in the methyl substituted by a heterocylic group, represented by $A^1$ and $A^2$, may optionally be each substituted by one or more substituents selected from the group consisting of halogen atom(s) (fluorine atom, chlorine atom, bromine atom, iodine atom), cyano, nitro, $C_1$–$C_{10}$ alkyl, $C_1$–$C_{10}$ haloalkyl, $C_3$–$C_{10}$ cycloalkyl, $C_1$–$C_{10}$ alkoxy, $C_1$–$C_{10}$ haloalkoxy, $C_1$–$C_{10}$ alkylthio, $C_1$–$C_{10}$ haloalkylthio, ($C_1$–$C_9$ alkyl)carbonyl, ($C_1$–$C_9$ alkoxy)carbonyl, ($C_1$–$C_9$ alkyl)carbonylamino, phenyl, phenoxy, benzyloxy, tri ($C_1$–$C_{10}$ alkyl)silyl, methylenedioxy and difluoromethylenedioxy; and as the alkoxy, the haloalkoxy, the alkylthio, the haloalkylthio, the alkylcarbonyl, the alkoxycarbonyl, the alkylcarbonylamino and the trialkylsilyl, the same substituents as described above are listed; as the alkyl, for example, methyl, ethyl, propyl, isopropyl, butyl, isobutyl, 1-methylpropyl, pentyl, 1-methylbutyl, 1-ethylbutyl, 2-methylbutyl, 3-methylbutyl, 2,2-dimethylpropyl, 1,2-dimethylpropyl, 1,1-dimethylpropyl, hexyl, 1-methylpentyl, 1-ethylpentyl, 3,3-dimethylbutyl, heptyl, 3,7-dimethyloctyl and the like are listed; as the haloalkyl, for example, trifluoromethyl, 2,2,2-trifluoroethyl, 1,1,2,2-tetrafluoroethyl and the like are listed; and as the cycloalkyl, for example, cyclopropyl, cyclopentyl, cyclohexyl and the like are listed; and the methylenedioxy and the difluoromethylenedioxy are each substituted on adjacent two carbon atoms in a benzene ring, naphthalene ring or heterocyclic ring.

The m-phenylene, m-azaphenylene and m-diazaphenylene, bonded to $R^1$ and to $CH_2$ each via a carbon atom, represented by T may optionally be substituted by halogen atoms (fluorine atom, chlorine atom, bromine atom, iodine atom), cyano, nitro, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ haloalkylthio or ($C_1$–$C_5$ alkoxy)carbonyl; and as the alkyl, for example, methyl, ethyl and the like are listed; as the haloalkyl, for example, fluoromethyl, difluoromethyl, trifluoromethyl, chloromethyl and the like are listed; as the alkoxy, for example, methoxy, ethoxy and the like are listed; as the haloalkoxy, for example, trifluoromethoxy, difluoromethoxy, bromodifluoromethoxy, chlorodifluoromethoxy, fluoromethoxy, 2,2,2-trifluoroethoxy, 1,1,2,2-tetrafluoroethoxy and the like are listed; as the alkylthio, for example, methylthio, ethylthio and the like are listed; as the haloalkylthio, for example, a trifluoromethylthio, difluoromethylthio, bromodifluoromethylthio, chlorodifluoromethylthio, fluoromethylthio, 2,2,2-trifluoroethylthio, 1,1,2,2-tetrafluoroethylthioandthe like are listed; and as the alkoxycarbonyl, for example, methoxycarbonyl, ethoxycarbonyl and the like are listed.

As more specific examples of T, groups of the following formulae:

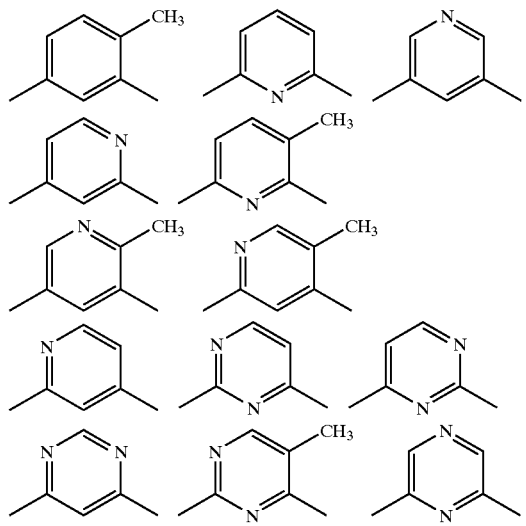

are listed.

Among the compounds of the invention, the compounds in which $R^1$ is optionally substituted phenyl (namely, $R^1$ is a $A^1$-$L^1$-, $L^1$ is single bond, and $A^1$ is optionally substituted phenyl) are preferable because of an excellent fungicidal effect. Further, the compounds in which T is m-phenylene or substituted m-phenylene are preferable because of an excellent fungicidal effect, and the preferable substituents include methyl, fluorine atom, chlorine atom and trifluoromethyl.

Particularly, the compounds of the following formula [LX] in which $R^1$ is optionally substituted phenyl and T is methylphenylene described below are preferable because of an excellent fungicidal effect.

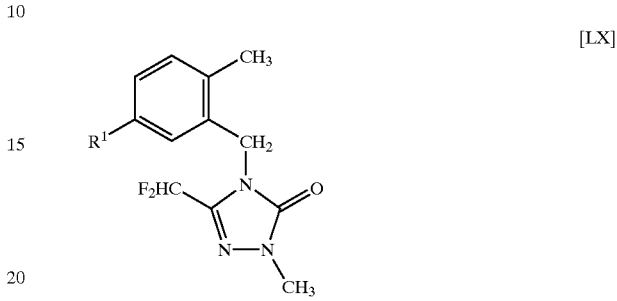

[LX]

As the specific example of such compounds, 5-difluoromethyl-2-methyl-4-(2-methyl-5-phenylbenzyl)-2,4-dihydro-3H-1,2,4-triazol-3-one [Compound 1] of the formula:

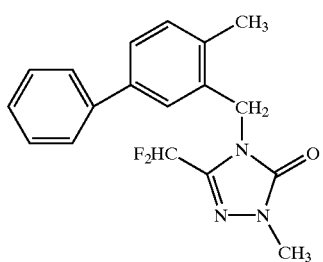

is mentioned.

The compound of the invention can be produced according to the following Production Method A to Production Method G. Depending on the definition of $R^1$, a desired $R^1$ can be introduced or structured last (for example, Production Method H). In these Production Methods, a protective group can be used for protecting a functional group from reaction, if necessary.

Production Method A

The compound of the invention of the formula [I] can be produced from a formyl compound of the formula [II] by, for example, a method shown in the following chemical reaction formula:

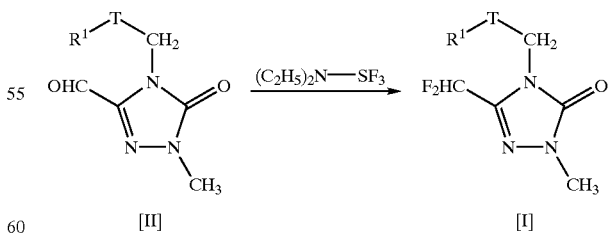

wherein, $R^1$ and T have the same meanings as described above.

The reaction temperature of the reaction of obtaining the compound of the invention of the formula [I] from the formyl compound of the formula [II] is usually in the range from −20° C. to 100° C., and the reaction time is usually in the range from 10 minutes to 10 hours. The ratio of diethylaminosulfur trifluoride used for this reaction is usually 1 to 20 mol per mol of the formyl compound of the formula [II].

The reactLion is conducted usually in a solvent, and as the solvent used, for example, halogenated hydrocarbons such as chloroform, chlorobenzene and the like, ethers such as 1,4-dioxane, tetrehydrofuran, diethyl ether and the like, aliphatic hydrocarbons such as hexane, petroleum ether and the like, aromatic hydrocarbons such as toluene, xylene and the like, and mixtures thereof are listed.

The reaction solution after completion of the reaction is subjected to post treatments such as, for example, washing with a sodium bicarbonate solution before concentration of the organic layer, and the like, giving isolation of the intended compound. This intended compound can also be purified by re-crystallization, chromatography and the like.

The formyl compound of the formula [II] can be produced, for example, according to the following scheme.

usually 1 to 10 mol per mol of the isocyanate compound of the formula [III]. The reaction is usually conducted in a solvent, and as the solvent used, for example, ethers such as 1,4-dioxane, tetrehydrofuran, diethyl ether and the like, halogenated hydrocarbons such as chloroform, chlorobenzene and the like, aliphatic hydrocarbons such as hexane, petroleum ether and the like, aromatic hydrocarbons such as toluene, xylene and the like, amides such as N,N-dimethylformamide and the like, dimethylsulfoxide and the like, and mixtures thereof are listed. The reaction solution after completion of the reaction is subjected to post treatments such as concentration, and the like, giving isolation of the intended compound. This intended compound can also be purified by re-crystallization, chromatography and the like. A semicarbazide compound of the formula [VIII] can be produced by reacting the isocyanate compound of the formula [III] with 1-methyl-2-hydroxyacetylhydrazine in

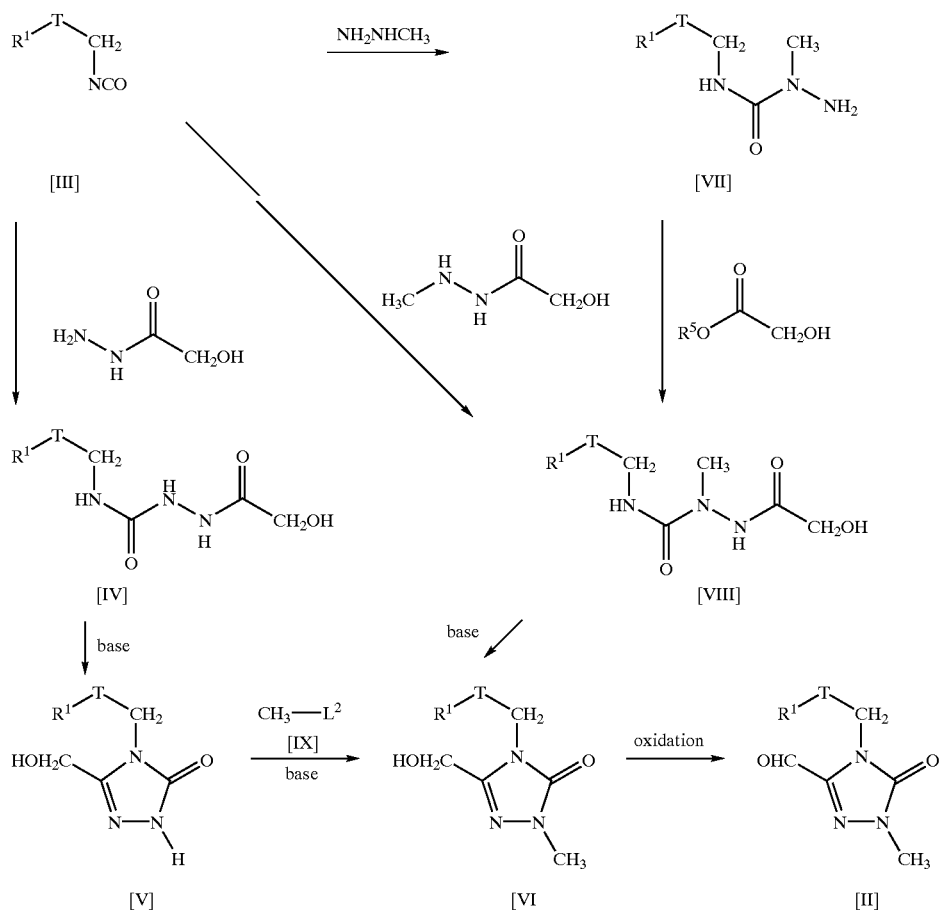

wherein, $R^1$ and T have the same meanings as described above, $L^2$ represents a leaving group such as a chlorine atom, bromine atom, iodine atom, p-toluenesulfonyloxy, methanesulfonyloxy, trifluoromethanesulfonyloxy and the like, and $R^5$ represents a $C_1$-$C_5$ alkyl (for example, methyl, ethyl and the like), phenyl or trihaloethyl (for example, trichloroethyl and the like).

A semicarbazide compound of the formula [VII] can be produced by reacting an isocyanate compound of the formula [III] with methylhydrazine. The reaction temperature of the reaction is usually in the range from −20° C. to 50° C., and the reaction time is usually in the range from 1 to 100 hours. The ratio of methylhydrazine used for this reaction is the same manner as described above. A semicarbazide compound of the formula [IV] can also be produced by reacting the isocyanate compound of the formula [III] with hydroxyacetylhydrazine in the same manner as described above.

A compound of the formula [V] can be obtained by reacting the semicarbazide compound of the formula [IV] with a base, and for example, can be obtained by treating the compound of the formula [V] with an aqueous potassium hydroxide solution.

A compound of the formula [VI] can be obtained by reacting the semicarbazide compound of the formula [VIII] with a base, and for example, can be obtained by treating the compound of the formula [VI] with an aqueous potassium hydroxide solution.

A compound of the formula [VI] can be obtained by reacting the compound of the formula [V] with a base, and as the base used, for example, potassium carbonate is mentioned.

The compound of the formula [II] can be obtained by oxidizing the compound of the formula [VI], and as the oxidizing agent used, for example, manganese dioxide is mentioned.

The isocyanate compound of the formula [III] can be produced, for example, according to the following scheme.

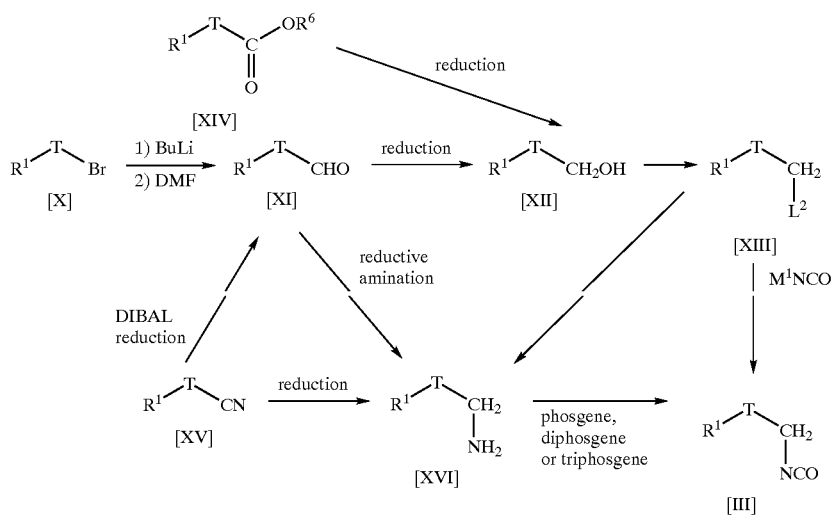

wherein, $R^1$, $L^2$ and T have the same meanings as described above, $R^6$ represents a $C_1$–$C_4$ alkyl (for example, methyl, ethyl and the like), $M^1$ represents silver or sodium, DIBAL represents diisobutyl aluminum hydride, BuLi represents butyllithium and DMF represents N,N-dimethylformamide.

The reaction of reacting an amine compound of the formula [XVI] with triphosgene, diphosgene or phosgene to obtain the isocyanate compound of the formula [III] can be conducted, for example, by a method described in J. Org. Chem. 61, 3883–3884 (1996) or by a method described in Intermediate Production Example 3 described later.

The reaction of reducing a nitrile compound of the formula [XV] to obtain the amine compound of the formula [XVI] can be conducted, for example, by a method of reduction using aluminum lithium hydride (LiAlH$_4$), by a method of hydrogenating the nitrile compound of the formula [XV] in the presence of a catalyst, and by the like manner; as the catalyst used in hydrogenation, for example, Raney nickel, palladium and the like are listed. Regarding the method of using Raney nickel, JP-A No. 8-291116 can be refered, and regarding the method of using pallaridum, J. Am. Chem. Soc., 50, 3370 (1928) can be refered, respectively.

The reaction of obtaining a compound of the formula [XIII] wherein $L^2$ represents a p-toluenesulfonyloxy, methanesulfonyloxy or trifluoromethanesulfonyloxy from an alcohol compound of the formula [XII] can be conducted, for example, according to a method described in Intermediate Production Example 12 described later.

The reaction of obtaining a compound of the formula [XIII] wherein $L^2$ represents a chlorine atom from the alcohol compound of the formula [XII] can be conducted, for example, by a method of reacting $CCl_4$-$PPh_3$ to the alcohol compound of the formula [XII] (specifically, method described in Intermediate Production Example 9 described later), by a method of reacting conc. Hydrochloric acid to the alcohol compound of the formula [XII] (see, Org. Synth., IV, 576 (1967)), and by the like manner. The similar methods are applicable to the compound which L2 is bromine atom or iodine atom.

The reaction of obtaining an amine compound of the formula [XVI] from a compound of the formula [XIII] can be conducted, for example, according to a method described in J. Org. Chem., 58, 270 (1993).

Other methods in the above-mentioned scheme can be conducted by ordinary methods.

An alcohol compound of the formula [XII] wherein T is the formula:

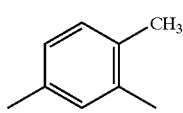

can also be produced from a benzyl chloride compound of the formula [XVII] according to the following chemical reaction formula:

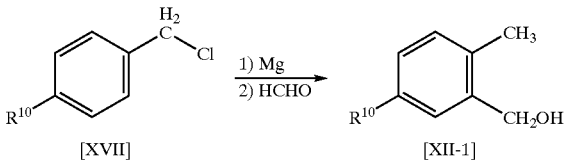

wherein, $R^{10}$ represents a substituent inactive in Grignard reaction among substituents defined for $R^1$.

This reaction is conducted in a solvent, and as the solvent used, ethers such as diethyl ether, tetrahydrofuran, diglyme, triglyme and the like, and mixed solvents of these ethers with aromatic hydrocarbons such as toluene, xylene and the like. If necessary, for example, J. Am. Chem. Soc., 73, 3237 (1951) can be refered.

Among the compounds of the formula [XIII], 2-methyl-5-phenylbenzyl chloride of the formula [XIII-1] can also be produced according to the following scheme.

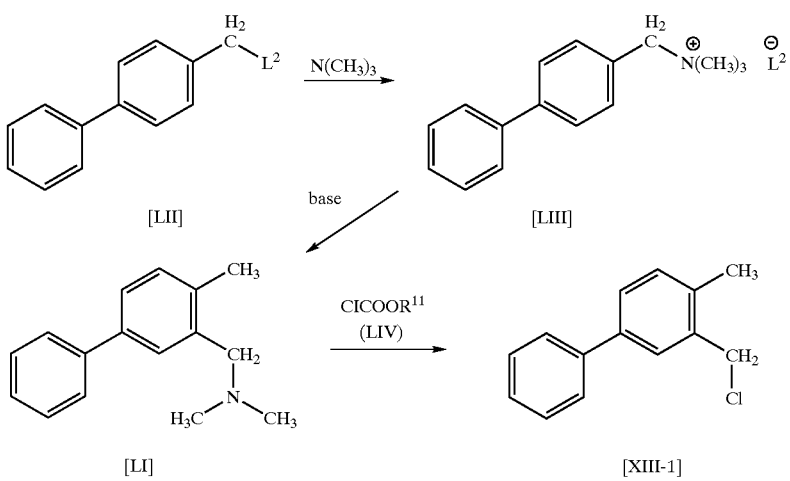

wherein, $L^2$ has the same meaning as described above, and $R^{11}$ represents a $C_1$–$C_4$ alkyl group (for example, methyl, ethyl and the like) or vinyl.

The reaction of obtaining a compound of the formula [LIII] from a compound of the formula [LII] can be conducted, for example, according to a method described in Tetrahedron, 50, 13697 (1994).

The reaction of obtaining N,N-dimethyl-(2-methyl-5-phenylbenzyl)amine of the formula [LI] from a compound of the formula [LIII] (Sommelet-Hauser rearrangement) can be conducted, for example, according to a method described in Organic Reactions, 18, 403–464 (1970). As the base used for this reaction, sodium hydride, potassium hydride, sodiumamide, potassiumamide, phenyllithium, butyllithium and the like are listed.

The reaction of obtaining 2-methyl-5-phenylbenzyl chloride of the formula [XIII-1] from N,N-dimethyl-(2-methyl-5-phenyl)benzylamine can be conducted, for example, according to a method described in Tetrahedron Lett., 24, 3233 (1983).

Production Method B

The compound of the invention of the formula [I] can be produced from a triazolone compound of the formula [XIX] according to the following chemical reaction formula.

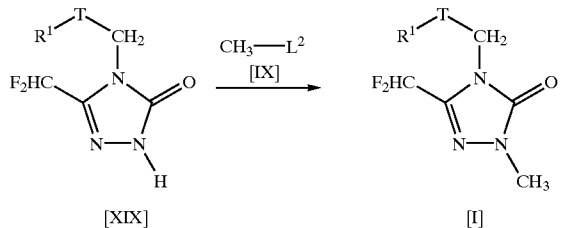

wherein, $R^1$, $L^2$ and T have the same meanings as described above.

The reaction is conducted usually in the presence of a base, and as the base used, for example, inorganic bases such as sodium hydride, sodium hydroxide, potassium hydroxide, sodium carbonate, potassium carbonate, and the like are listed.

The reaction temperature of the reaction of obtaining the compound of the invention of the formulae [I] from a triazolone compound of the formula [XIX] is usually in the range from –20° C. to 100° C., and the reaction time is usually in the range from 1 to 100 hours.

Regarding the amounts of reagents used for the reaction, the ratio of a methylating agent of the formula [IX] is 1 to 5 mol and the ratio of the base is 1 to 10 mol, per mol of the triazolone compound of the formula [XIX].

The reaction is conducted in a solvent if necessary, and as the solvent used, for example, ethers such as 1,4-dioxane, tetrehydrofuran, ethylene glycol dimethyl ether, diethylene glycol dimethyl ether, t-butyl methyl ether and the like, aliphatic hydrocarbons such as hexane, heptane, ligroin, petroleum ether and the like, aromatic hydrocarbons such as toluene, xylene and the like, organic bases such as pyridine, triethylamine, N-methylaniline, N,N-dimethylaniline, N,N-diethylaniline and the like, nitriles such as acetonitrile, isobutylonitrile and the like, N,N-dimethylformamide, dimethyl sulfoxide, water and the like, and mixtures thereof are listed. These solvents are selected depending on the kind of a base used.

The reaction solution after completion of the reaction is subjected to usual post treatments such as extraction with an organic solvent, concentration and the like, giving isolation of the intended compound. This intended compound can also be purified by re-crystallization, chromatography and the like.

The triazolone compound of the formula [XIX] can be produced, for example, according to the following scheme.

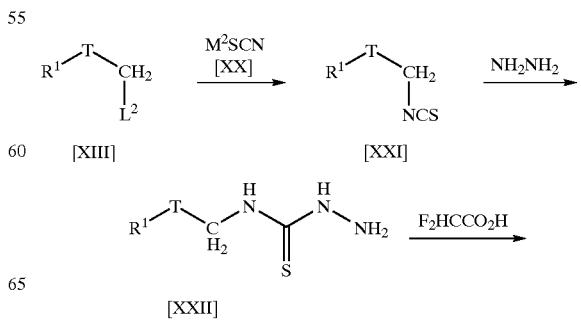

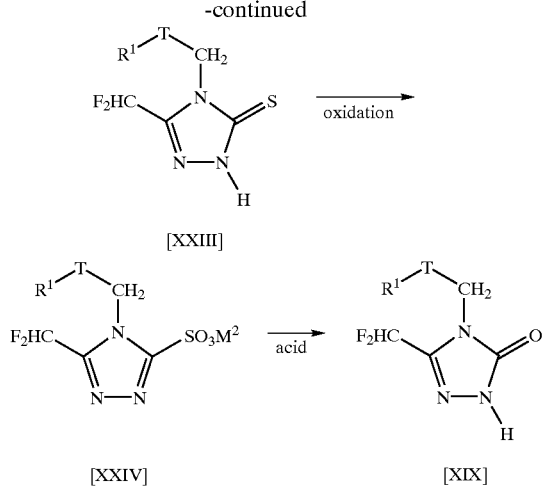

[XXIII]

[XXIV] [XIX]

wherein, $R^1$, $L^2$ and T have the same meanings as described above, and $M^2$ represents sodium or potassium.

An isothiocyanate compound of the formula [XXI] can be produced by reacting a compound of the formula [XIII] with a compound of the formula [XX]. A thiosemicarbazide compound of the formula [XXII] can be produced by reacting the isothiocyanate compound of the formula [XXI] with hydrazine (anhydrous hydrazine or water-containing hydrazine). A triazolinethion compound of the formula [XXIII] can be produced by reacting the thiosemicarbazide compound of the formula [XXII] with difluoroacetic acid. A sulfonic acid compound of the formula [XXIV] can be produced by oxidizing the triazolinethion compound of the formula [XXIII] using an oxidizing agent (for example, hydrogen peroxide). The triazolone compound of the formula [XIX] can be produced by hydrolyzing the sulfonic acid compound of the formula [XXIV] using an acid (for example, hydrochloric acid). In conducting processes starting from a thiosemicarbazide compound of the formula [XXII] to a triazolone compound of the formula [XIX], for example, JP-A No. 7-196630 can be referred.

The reaction solution after completion of the reaction is subjected to usual post treatments such as extraction with an organic solvent, concentration and the like, giving isolation of the intended compound. This intended compound can also be purified by re-crystallization, chromatography and the like.

Production Method C

The compound of the invention of the formula [I] can be produced from a semicarbazide compound of the formula [VII], for example, according to the following chemical reaction formula.

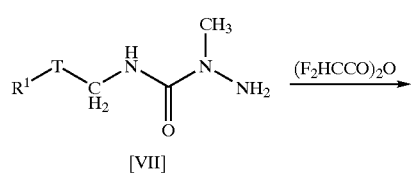

[VII]

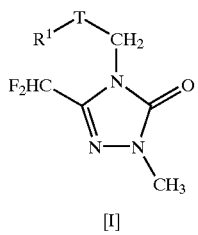

[I]

wherein, $R^1$ and T have the same meanings as described above.

The reaction temperature of the above-mentioned reaction of obtaining the compound of the invention of the formula [I] from a semicarbazide compound of the formula [VII] is usually in the range from −20° C. to 100° C., and the reaction time is usually in the range from 1 to 100 hours.

Regarding the amounts of reagents used for the reaction, the ratio of a difluoroacetic anhydride is usually 1 to 5 mol per mol of the semicarbazide compound of the formula [VII].

The reaction is usually conducted in a solvent, and as the solvent used, for example, aromatic hydrocarbons such as toluene, xylene and the like, ethers such as 1,4-dioxane, tetrehydrofuran, diethyl ether and the like, aliphatic hydrocarbons such as hexane, petroleum ether and the like, and mixtures thereof are listed.

In this reaction, a difluoroacetyl semicarbazide compound of the formula [XXVI] described later is formed as a by-product in some cases, however, it can be separated off by purifying the intended compound by chromatography and the like. The separated difluoroacetyl semicarbazide compound of the formula [XXVI] can be utilized as a starting material for Production Method F described later.

The reaction solution after completion of the reaction can be, for example after decomposition of excess difluoroacetic anhydride by a base such as an aqueous sodium hydroxide solution and the like, subjected to post treatment operations such as extraction with an organic solvent, concentration and the like, giving isolation of the intended compound. This intended compound can also be purified by re-crystallization, chromatography and the like.

Production Method D

The compound of the invention of the formula [I] can be produced from the semicarbazide compound of the formula [VII], for example, according to the following chemical reaction formula.

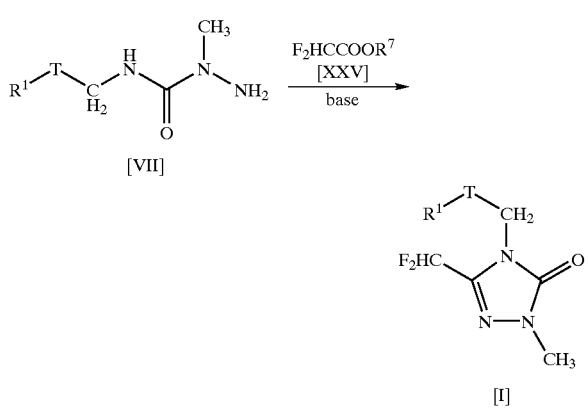

wherein, $R^1$ and T have the same meanings as described above, and $R^7$ represents a $C_1$–$C_4$ alkyl (for example, methyl, ethyl and the like).

The reaction temperature of the above-mentioned reaction of obtaining the compound of the invention of the formula [I] from the semicarbazide compound of the formula [VII] is usually in the range from −20° C. to 100° C., and the reaction time is usually in the range from 1 to 100 hours.

Regarding the amounts of reagents used for the reaction, the ratio of a compound of the formula [XXV] is usually 1 to 100 mol per mol of the semicarbazide compound of the formula [VII].

The reaction is conducted in the presence of a base, and as the base used, for example, metal alkoxides such as sodium methoxide, sodium ethoxide, potassium t-butoxide and the like, alkali metal hydroxides such as sodium hydroxide, potassium hydroxide and the like, alkaline earth metal hydroxides such as calcium hydroxide, magnesium hydroxide and the like, and organic bases such as triethylamine, pyridine and the like are listed, and the ratio of a base is usually 0.1 to 3 mol per mol of the semicarbazide compound of the formula [VII]

The reaction is conducted in a solvent if necessary, and as the solvent used, for example, alcohols such as methanol, ethanol and the like, ethers such as 1,4-dioxane, tetrehydrofuran, diethyl ether and the like, aliphatic hydrocarbons such as hexane, petroleum ether and the like, aromatic hydrocarbons such as toluene, xylene and the like, amides such as N,N-dimethylformamide and the like, dimethylsulfoxide and the like, and mixtures thereof are listed.

In this reaction, a difluoroacetyl semicarbazide compound of the formula [XXVI] described later is formed as a by-product in some cases, however, it can be separated off by purifying the intended compound by chromatography and the like. The separated difluoroacetyl semicarbazide compound of the formula [XXVI] can be utilized as a starting material for Production Method F described later.

The reaction solution after completion of the reaction can be, after neutralization or concentration if necessary, subjected to post treatment operations such as extraction with an organic solvent, concentration and the like, giving isolation of the intended compound. This intended compound can also be purified by re-crystallization, chromatography and the like.

Production Method E

The compound of the invention of the formula [I] can be produced from a semicarbazide compound of the formula [VII], for example, according to the following chemical reaction formula.

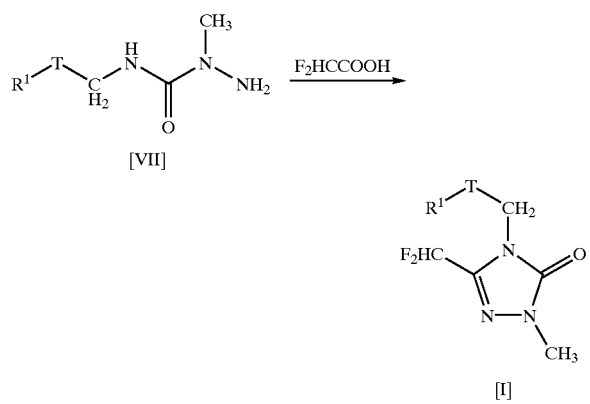

wherein, $R^1$ and T have the same meanings as described above.

The reaction temperature of the above-mentioned reaction of obtaining the compound of the invention of the formula [I] from the semicarbazide compound of the formula [VII] is usually in the range from 20° C. to 100° C., and the reaction time is usually in the range from 1 to 100 hours.

Regarding the amounts of reagents used for the reaction, the ratio of difluoroacetic acid is usually 1 to 100 mol per mol of the semicarbazide compound of the formula [VII].

The reaction is conducted in a solvent if necessary, and as the solvent used, for example, aromatic hydrocarbons such as toluene, xylene and the like, aliphatic hydrocarbons such as hexane, petroleum ether and the like, ethers such as 1,4-dioxane, tetrahydrofuran and the like, and mixtures thereof are listed.

In this reaction, the difluoroacetyl semicarbazide compound of the formula [XXVI] described later is formed as a by-product in some cases, however, it can be separated off by purifying the intended compound by chromatography and the like. The separated difluoroacetyl semicarbazide compound of the formula [XXVI] can be utilized as a starting material for Production Method F described later.

The reaction solution after completion of the reaction can be, after neutralization or concentration if necessary, subjected to post treatment operations such as extraction with an organic solvent, concentration and the like, giving isolation of the intended compound. This intended compound can also be purified by re-crystallization, chromatography and the like.

Production Method F

The compound of the invention of the formula [I] can be produced from the difluoroacetyl semicarbazide compound of the formula [XXVI], for example, according to the following chemical reaction formula.

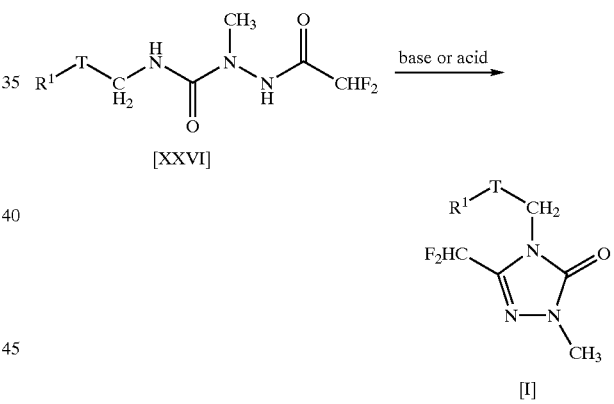

wherein, $R^1$ and T have the same meanings as described above.

The reaction temperature of the reaction of obtaining the compound of the invention of the formula [I] from the difluoroacetyl semicarbazide compound of the formula [XXVI] is usually in the range from 20° C. to 100° C., and the reaction time is usually in the range from 10 minutes to 10 hours.

The reaction is conducted in the presence of a base or acid, and as the base used, for example, metal alkoxides such as sodium methoxide, sodium ethoxide, potassium t-butoxide and the like, alkali metal hydroxides such as sodium hydroxide, potassium hydroxide and the like, alkaline earth metal hydroxides such as calcium hydroxide, magnesium hydroxide and the like, and organic bases such as triethylamine, pyridine and the like are listed. The ratio of the base used is usually 0.1 to 10 mol per mol of a difluoroacetyl semicarbazide compound of the formula [XXVI]. As the acid used, for example, organic acids such as difluoroacetic acid, trifluoroacetic acid and the like are listed, and the ratio of the acid used is usually 1 to 100 mol per mol of the difluoroacetyl semicarbazide compound of the formula [XXVI].

The reaction is conducted in a solvent if necessary, and as the solvent used, for example, alcohols such as methanol, ethanol and the like, ethers such as 1,4-dioxane, tetrahydrofuran, diethyl ether and the like, aliphatic hydrocarbons such as hexane, petroleum ether and the like, aromatic hydrocarbons such as toluene, xylene and the like, amides such as N,N-dimethylformamide and the like, sulfoxides such as dimethyl sulfoxide and the like, water and mixtures thereof are listed. These solvents are selected and used depending on the kinds of an acid and base used.

The reaction solution after completion of the reaction can be, after neutralization or concentration if necessary, subjected to post treatment operations such as extraction with an organic solvent, concentration and the like, giving isolation of the intended compound. This intended compound can also be purified by re-crystallization, chromatography and the like.

The difluoroacetyl semicarbazide compound of the formula [XXVI] can also be obtained as a by-product in Production Methods C, D and E, however, can be produced, for example, according to the following scheme.

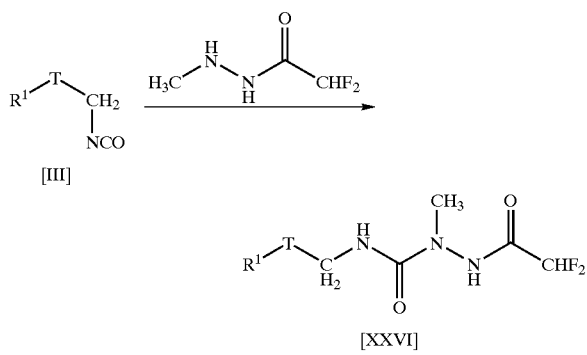

wherein, $R^1$ and T have the same meanings as described above.

The reaction temperature in obtaining the difluoroacetyl semicarbazide compound of the formula [XXVI] from the isocyanate compound of the formula [III] is usually in the range from 0° C. to 100° C., and the reaction time is usually in the range from 1 to 10 hours.

The ratio of N'-methyl-difluoroacetohydrazide used for the reaction is usually 1 to 10 mol per mol of the isocyanate compound of the formula [III].

The reaction is conducted in a solvent if necessary, and as the solvent used, for example, alcohols such as methanol, ethanol and the like, ethers such as 1,4-dioxane, tetrahydrofuran, diethyl ether and the like, halogenated hydrocarbons such as chloroform, chlorobenzene and the like, aliphatic hydrocarbons such as hexane, petroleum ether and the like, aromatic hydrocarbons such as toluene, xylene and the like, amides such as N,N-dimethylformamide and the like, dimethylsulfoxide and the like, and mixtures thereof are listed.

The reaction solution after completion of the reaction is subjected, after concentration, to post treatment operations such as extraction with an organic solvent, concentration and the like, giving isolation of the intended compound. This intended compound can also be purified by re-crystallization, chromatography and the like.

Production Method G

The compound of the invention of the formula [I] can be produced from a compound of the formula [XIII] and a triazolone compound of the formula [L], for example, according to the following chemical reaction formula.

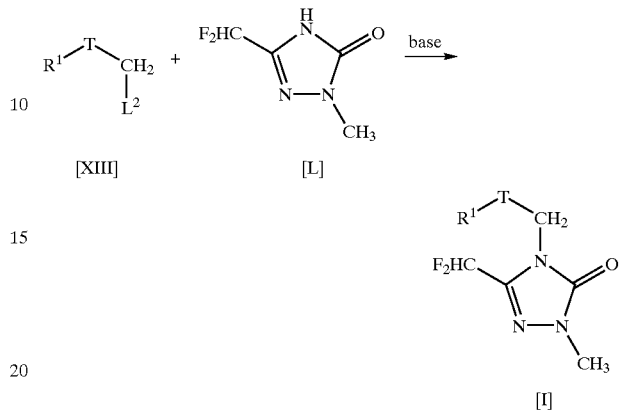

wherein, $R^1$, $L^2$ and T have the same meanings as described above.

The reaction is conducted in the presence of a base, and as the base used, inorganic bases such as lithium hydroxide, lithium hydride, sodium hydroxide, sodium hydride, potassium hydroxide, potassium hydride, sodium carbonate, potassium carbonate, and the like are listed. The reaction temperature is usually in the range from 0° C. to 100° C., and the reaction time is usually in the range from 1 to 100 hours.

Regarding the amounts of reagents used for the reaction, the ratio of the triazolone compound of the formula [L] is usually 1 to 5 mol and the ratio of a base is usually from 1 to 10 mol per mol of the compound of the formula [XIII].

The reaction is conducted in a solvent if necessary, and as the solvent used, for example, alcohols such as methanol, ethanol and the like, ethers such as 1,4-dioxane, ethylene glycol dimethyl ether, diethylene glycol dimethyl ether and the like, aromatic hydrocarbons such as toluene, xylene and the like, organic bases such as pyridine, triethylamine, N-methylaniline, N,N-dimethylaniline, N,N-diethylaniline and the like, nitriles such as acetonitrile, isobutylonitrile and the like, N,N-dimethylformamide, dimethyl sulfoxide, water and the like, and mixtures thereof are listed. These solvents are selected depending on the kinds of a base used.

The reaction solution after completion of the reaction is subjected to post treatment operations such as extraction with an organic solvent, concentration and the like, giving isolation of the intended compound. This intended compound can also be purified by re-crystallization, chromatography and the like.

The triazoline compound of the formula [L] can be produced, for example, according to the following chemical reaction formula.

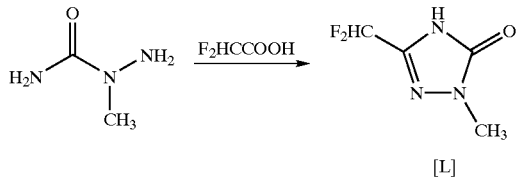

The reaction temperature in obtaining the triazolone compound of the formula [L] from 2-methyl semicarbazide is usually in the range from 50° C. to 150° C., and the reaction time is usually in the range from 1 to 100 hours.

The ratio of difluoroacetic acid used for the reaction is usually 1 to 100 mol per mol of 2-methyl semicarbazide.

The reaction is conducted in a solvent if necessary, and as the solvent used, for example, aromatic hydrocarbons such as toluene, xylene and the like, aliphatic hydrocarbons such as hexane, petroleum ether and the like, ethers such as 1,4-dioxane, tetrahydrofuranand the like, and mixtures thereof are listed.

In this reaction, 1-difluoroacetyl-2-methyl semicarbazide is formed as a by-product in some cases, however, it can be separated off by purification by chromatography and the like.

The reaction solution after completion of the reaction can be, after neutralization or concentration if necessary, subjected to post treatment operations such as extraction with an organic solvent, concentration and the like, giving isolation of the intended compound. This intended compound can also be purified by re-crystallization, chromatography and the like.

The triazolone compound of the formula [L] can be shown as tautomers described below.

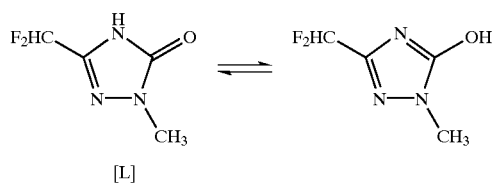

[L]

2-methyl semicarbazide can be produced, for example, according to the following chemical reaction formula.

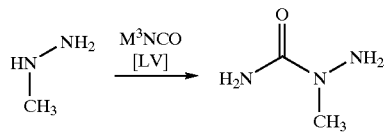

wherein, $M^3$ represents sodium or potassium.

This reaction is conducted usually in an acidic aqueous solution (for example, hydrochloric acid).

Trimethylsilyl isocyanate of the above-mentioned formula in which $M^3$ represents a trimethylsilyl is reacted with methylhydrazine, then, the reaction product is reacted with methanol. Thus, 2-methyl semicarbazide can be produced.

Production Method H

Production can be effected by the following methods (H-1) to (H-6).

(H-1): Method of producing the compound of the invention of the formula [I-2] wherein $R^1$ in the formula [I] is phenyl, naphthyl or heterocyclic group

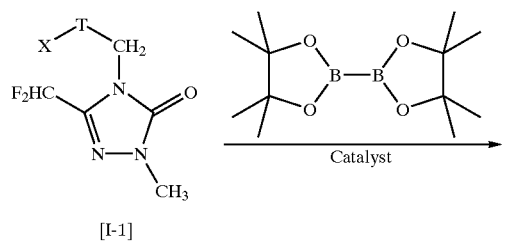

[I-1]

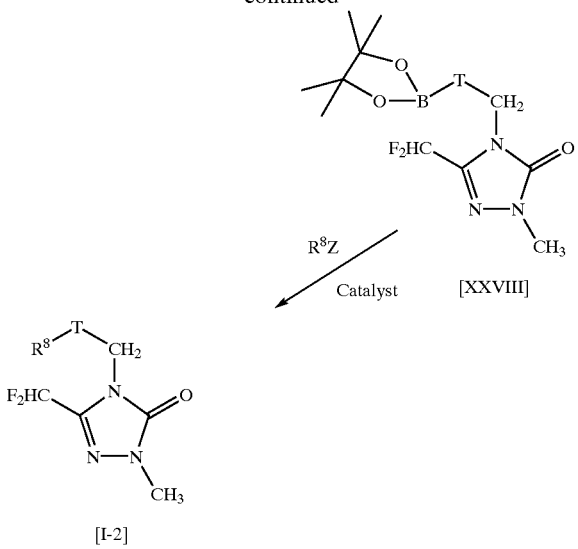

[I-2]

wherein, $R^8$ represents phenyl, naphthyl or heterocyclic group, and the phenyl, naphthyl or heterocyclic group may optionally be each substituted by one or more substituents selected from the group consisting of halogen atoms, cyano, nitro, $C_1$–$C_{10}$ alkyl, $C_1$–$C_{10}$ haloalkyl, $C_3$–$C_{10}$ cycloalkyl, $C_1$–$C_{10}$ alkoxy, $C_1$–$C_{10}$ haloalkoxy, $C_1$–$C_{10}$ alkylthio, $C_1$–$C_{10}$ haloalkylthio, ($C_1$–$C_9$ alkyl) carbonyl, ($C_1$–$C_9$ alkoxy)carbonyl, ($C_1$–$C_9$ alkyl)carbonylamino, phenyl, phenoxy, benzyloxy, $C_3$–$C_{20}$ Lrialkylsilyl, methylenedioxy and difluoromethylenedioxy; X and Z are the same or different and represent a chlorine atom, bromine atom, iodine atom or trifluoromethanesulfonyloxy; and T has the same meaning as described above.

(1) Method of producing aborate compound of the formula [XXVIII]

A borate compound of the formula [XXVIII] can be produced by reacting a compound of the formula [I-1] with bis(pinacolate)diboron in an organic solvent (for example, dimethyl sulfoxide, dimethylformamide) in the presence of a base (for example, potassium acetate, potassium carbonate) and a palladium catalyst (for example, dichloromethane complex of [bis(diphenylphosphino)ferrocene] dichloropalladium (II), tetrakistriphenylphosphinepalladium).

The reaction solution after completion of the reaction can be added to water, then, subjected to post treatments such as extraction with an organic solvent, concentration and the like, giving isolation of the intended compound. This intended compound can also be purified by chromatography and the like.

In this reaction, J. Org. Chem., 60, 7508–7510 (1995) can be refered, if necessary.

(2) Method of producing a compound of the invention of the formula [I-2]

The compound of the invention of the formula [I-2] can be produced by reacting the borate compound of the formula [XXVIII] with a compound of the general formula $R^8Z$ in an organic solvent (for example, dimethoxyethane) in the presence of a base (for example, potassium phosphate, potassium carbonate) and a palladium catalyst (for example, dichloromethane complex of [bis(diphenylphosphino) ferrocene]dichloropalladium (II), palladiumacetate (II), tetrakistriphenylphosphinepalladium, mixtures thereof).

A solvent in the reaction solution after completion of the reaction is distilled off, for example, then, the residue is subjected to chromatography, or the reaction solution after completion of the reaction is subjected to post treatments such as extraction with an organic solvent, concentration and the like. Thus the intended compound can be obtained. This intended compound can also be purified by re-crystallization, chromatography and the like.

In this reaction, TetrahedronLett., 38, 7645–7648 (1997) can be refered, if necessary. (H-2) Method shown in the following chemical reaction formula {method of producing the compound of the invention of the formula [I-3] wherein $R^1$ in the formula [I] is an alkynyl having a triple bond at the bonding end}

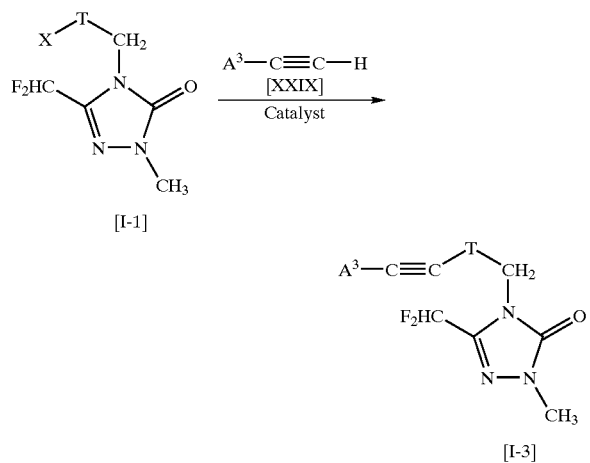

wherein, $A^3$—C≡C represents a $C_2$–$C_{10}$ alkynyl optionally substituted having a triple bond at the end. This alkynyl may optionally be substituted by one or more substituents selected from the group consisting of halogen atoms, cyano, nitro, $C_1$–$C_{10}$ alkoxy, $C_1$–$C_{10}$ haloalkoxy, $C_1$–$C_{10}$ alkylthio, $C_1$–$C_{10}$ haloalkylthio, ($C_1$–$C_9$ alkyl)carbonyl, ($C_1$–$C_9$ alkoxy)carbonyl, ($C_1$–$C_9$ alkyl) carbonylamino, phenyl, phenoxy, benzyloxy and $C_3$–$C_{20}$ trialkylsilyl; and T and X are the same as described above.

The reaction of obtaining a compound of the invention of the formula [I-3] from a compound of the formula [I-1] can be conducted, for example, in an aprotic polar solvent (for example, acetonitrile, N,N-dimethylformamide) in the presence of a base (for example, secondary amine such as disopropylamine and the like, tertiary amine such as triethylamine and the like) and a catalyst (for example, combination of triphenylphosphine, copper iodide (I) and palladium catalyst such as bis(triphenylphosphine)dichloropalladium {$PdCl_2(PPh_3)_2$} and the like). If necessary, WO98/03464, Example 1, Tetrahedron Lett., 16, 4467–4470 (1975), Synthesis, 1980, 627–630, or J. Org. Chem., 64, 2070–2079 (1999) can be referred.

The reaction solution after completion of the reaction can be subjected to post treatment operations such as extraction with an organic solvent, concentration and the like, to obtain the intended compound. This intended compound can also be purified by re-crystallization, chromatography and the like. (H-3) Method shown in the following chemical reaction formula {method of producing a compound of the invention of the formula [I-2] wherein $R^1$ in the formula [I] represents a phenyl, naphthyl or heterocyclic group}

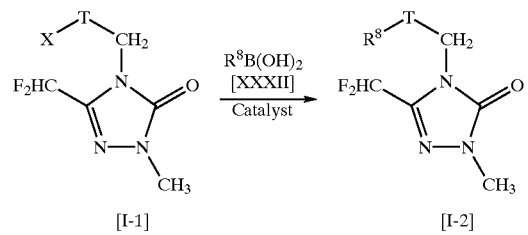

wherein, $R^8$, T and X are the same as described above.

The reaction of obtaining the compound of the invention of the formula [I-2] from a compound of the formula [I-1] can be conducted, for example, in a mixed solvent of water and diethoxyethane in the presence of a base (for example, inorganic base such as sodium bicarbonate) and a catalyst (for example, tetrakis(triphenyl)phosphinepalladium {Pd $(PPh_3)_4$}) (If necessary, see description in WO96/35669, Beispiel 2), or in a solvent in the presence of tetrabutylammonium bromide, base (for example, inorganic base such as potassium carbonate) and catalyst (for example, palladium acetate). The reaction solution after completion of the reaction can be subjected to post treatment operations such as extraction with an organic solvent, concentration and the like, to obtain the intended compound. This intended compound can also be purified by re-crystallization, chromatography and the like. If necessary, J. Org. Chem., 62, 7170–7173(1997) can be referred, for example. (H-4) Method shown in the following scheme {method of producing a compound of the invention of the formula [I-5] wherein $R^1$ in the formula [I] represents a phenoxy, naphthyloxy or heterocyclic-oxy optionally substituted}

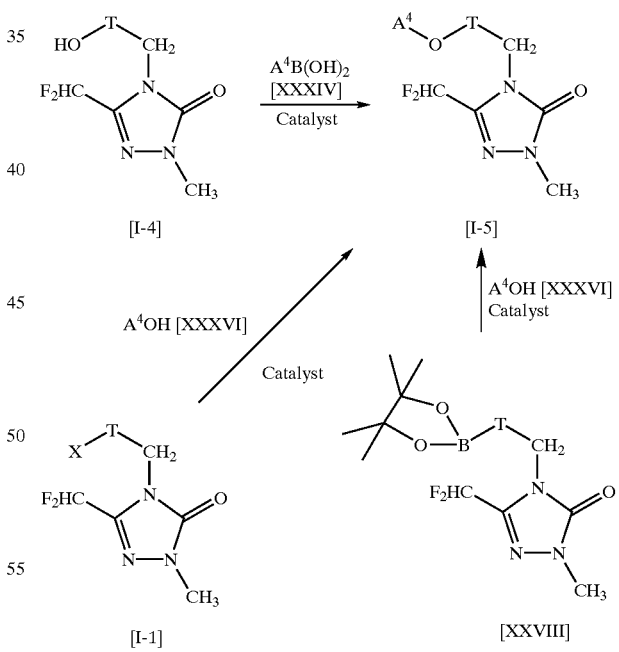

wherein, X and T have the same meanings as described above, and $A^4$ represents a phenyl, naphthyl or heterocyclic group, and the phenyl, naphthyl or heterocyclic group may optionally each be substituted by one or more substituents selected from the group consisting of halogen atoms, cyano, nitro, $C_1$–$C_{10}$ alkyl, $C_1$–$C_{10}$ haloalkyl, $C_3$–$C_{10}$ cycloalkyl, $C_1$–$C_{10}$ alkoxy, $C_1$–$C_{10}$ haloalkoxy, $C_1$–$C_{10}$ alkylthio, $C_1$–$C_{10}$ haloalkylthio, ($C_1$–$C_9$ alkyl) carbonyl, ($C_1$–$C_9$ alkoxy)carbonyl, ($C_1$–$C_9$ alkyl)carbonylamino, phenyl, phenoxy, benzyloxy, $C_3$–$C_{20}$ trialkylsilyl, methylenedioxy and difluoromethylenedioxy.

(1) Method of production from a compound of the formula [I-4]

The reaction of obtaining a compound of the invention of the formula [I-5] from a compound of the formula [I-4] can be conducted in an organic solvent (for example, methylene chloride) in the presence of a base (for example, organic base such as triethylamine and the like, inorganicbase such as sodium bicarbonate and the like) and a catalyst (for example, copper acetate (II)). If necessary, Tetrahedron Lett., 39, 2937–2940 (1998) can be refered.

(2) Method of production from a compound of the formula [I-1]

The reaction of obtaining a compound of the invention of the formula [I-5] from a compound of the formula [I-1] can be conducted in an organic solvent (for example, toluene, ethyl acetate) in the presence of a base (for example, organic base such as triethylamine and the like, inorganic base such as potassium carbonate, cesium carbonate and the like) and a catalyst (for example, copper iodide (I)). The reaction solution after completion of the reaction can be subjected to post treatment operations such as extraction with an organic solvent, concentration and the like, to obtain the intended compound. This intended compound can also be purified by re-crystallization, chromatography and the like.

In this reaction, if necessary, descriptions in J. Amer. Chem. Soc., 119, 10539–10540 (1997), J. Amer. Chem. Soc., 121, 3224–3225 (1999) and J. Amer. Chem. Soc., 121, 4369–4378 (1999) can be refered.

(3) Method of production from a compound of the formula [XXVIII]

The reaction of obtaining a compound of the invention of the formula [I-5] from a compound of the formula [XXVIII] can be conducted in an organic solvent (for example, methylene chloride) in the presence of a base (for example, organic base such as triethylamineand the like, inorganicbase such as sodium bicarbonate and the like) and a catalyst (for example, copper acetate (II)). If necessary, descriptions in Tetrahedron Lett., 39, 2937–2940 (1998) can be referred.

(H-5) Method shown in the following scheme {method of producing compounds of the inventionof the formulae [I-7] and [I-8] wherein $R^1$ in the formula [I] represents a $A^1$-ON=$CA^2$—}

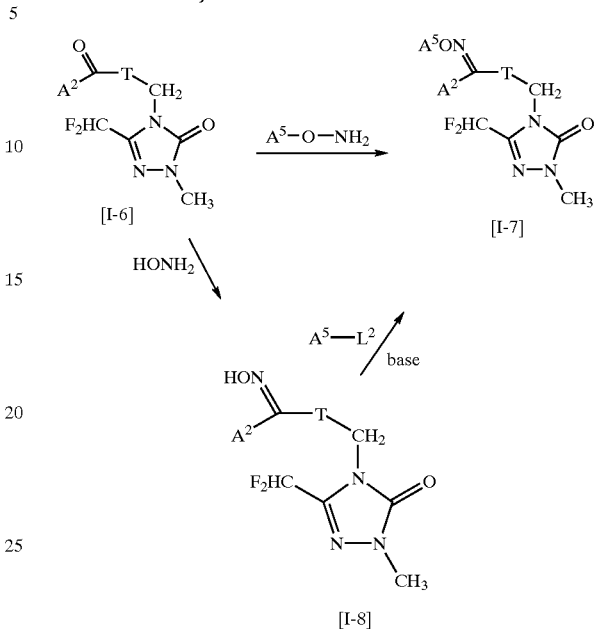

wherein, $A^5$ represents a group other than a hydrogen atom among represented by $A^1$, and $L^2$, $A^2$ and T have the same meanings as described above.

Compounds of the formula [I-7] in which $A^2$ is a methyl can be produced from a compound of the formula [I-6] according to a method described in J. Org. Chem., 57, 1481–1486 (1992). Other compounds can also be produced by ordinary methods according to the above-mentioned scheme. (H-6) Method shown in the following scheme

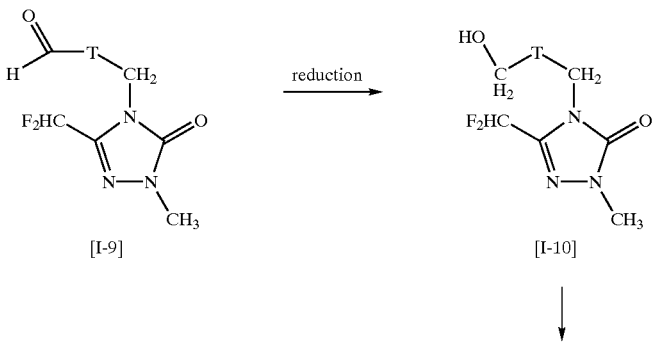

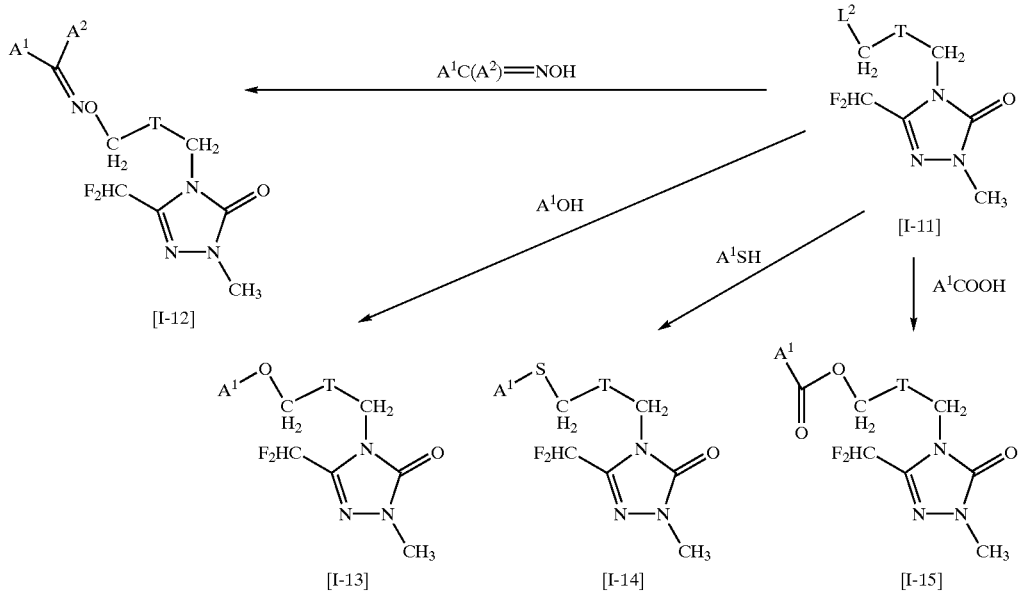

wherein, $A^1$, $A^2$, $L^2$ and T have the same meanings as described above.

Each process in the above-mentioned scheme can be conducted according to an ordinary method.

When the compound of the invention is used as an active ingredient of a fungicidal composition, it may be used itself without adding any other components, however, it is usually mixed with solid carriers, liquid carriers, surfactants and other adjuvants, to prepare emulsifiable concentrates, wettable powders, water dispersible granules, emulsion formulation, flowables, dust formulation, granules and the like, tobe used. These formulations contain the compound of the invention as an active ingredient in an amount of usually from 0.1 to 90 wt %.

The solid carrier to be used in the formulation may include, for example, the following materials in fine powder or granule form: mineral materials (e.g., kaolinite clay, attapulgite clay, bentonite clay, montmorillonite clay, acid clay, pyrophyllite, talc, diatomaceous earth, calcite), natural organic materials (e.g., stalks of corn, powder of wallnut-shell), synthetic organic materials (e.g., urea), salts (e.g., calciumcarbonate, ammonium sulfate) and synthetic inorganic materials (e.g., synthetic hydrated silicon oxide). The liquid carrier may include, for example, aromatic hydrocarbons (e.g., xylene, alkylbenzene, methylnaphthalene), alcohols (e.g., isopropyl alcohol, ethylene glycol, propylene glycol, ethylene glycol mono-ethyl ether), ketones (e.g., acetone, cyclohexanone, isophorone), vegetable oils (e.g., soybean oil, cotton seed oil), petroleum aliphatic hydrocarbons, esters, dimethyl sulufoxide, acetonitrileand-water. The surfactant may include, for example, anionic surfactants (e.g., alkylsulfate ester salts, alkyl (aryl) sulfonic acid salts, dialkylsulfosuccinic acid salts, phosphate salts of polyoxyethylenealkyl aryl ether, lignin sulfonic acid salts, naphthalenesulfonic acid formaldehyde condensations), nonionic surfactants (e.g., polyoxyethylene alkyl aryl ethers, polyoxyethylene propylene block copolymer, sorbitan fatty acid esters). The other adjuvants may include, for example, water-soluble polymers (e.g., polyvinyl alcohol, polyvinylpyrrolidone), polysaccharides (e.g., gumarabic, alginic acidand their salts, CMC (carboxy methyl cellulose), xanthan gum), inorganic materials (aluminum magnesium silicate, alumina sol), preservatives, coloringagents, PAP (isopropylacidphosphate), BHT.

The method of the application of the compound of the invention is concretely carried out, for example, by a foliar treatment, by a soil treatment, by a seed treatment and the like, also it is carried out by any method which is usually a person in the art uses.

When the compound of the invention is applied as the active ingredient of the fungicidal composition, the application amount of the active ingredient; although it may vary with a variety of plants (crops) to be protected, a variety of plant diseases to be controlled, a extent of disease damage, a formulation type, an application type, application times, weather condition and the like; is usually 1 to 5,000 g per hectare, preferably 5 to 1,000 g per hectare. In the case of emulsifiable concentrates, wettable powders, flowables and the like, they are usually applied after diluted with water, usually at a concentration of 0.0001 to 3% by weight, preferably at a concentration of 0.0005 to 1% by weight as active ingredients of the invention. In the case of dust formulations, granules and the like, they are usually applied as it is without diluting.

The compound of the invention can be used as a agricultural and horticultural antifungal agent in agricultural fields, paddy fields, orchards, tea plantations, grasslands, lawnsand the like. Increasing of the antifungal effect may be expected by using the compound of the invention with other agricultural and horticultural antifungal agent(s).

Example of the other agricultural and horticultural antifungal agents include:

azole antifungal compound such as propiconazole, triadimenol, prochloraz, penconazole, tebuconazole, flusilazole, diniconazole, bromoconazole, epoxyconazole, difenoconazole, cyproconazole, metconazole, triflumizole, tetraconazole, myclobutanil, fenbuconazole, hexaconazole, fluquinconazole, triticonazole, bitertanol, ipconazole, imibenconazole, imazalil, flutriafol and the like; cyclic amine antifungal compound such as fenpropimorph, tridemorph, fenpropidin and the like; benzimidazole antifungal compound such as carbendazim, benomyl, thiabendazole, thiophanate-methyl and the like; ethylen bis (dithiocarbamate) compound such as maneb, zineb, mancozeb and the like; phthalimide compound such as captan, folpet and the like; inorganic copper such as basic copper chloride, basic copper sulfate, copper sulfate, copper hydroxide and the like; organic copper such as copperoxinate, copper-nonylphenol-sulfonate and the like; procymidone, cyprodinil, pyrimethanil, diethofencarb, thiuram, fluazinam, iprodione, vinclozolin, chlorothalonil, mepanipyrim, fenpiclonil, fludioxonil, dichlofluanid, folpet, kresoxim-methyl, azoxystrobin, trifloxystrobin, picoxystrobin, N-methyl-α-methoxyimino-2-[(2,5-dimethylphenoxy)methyl]phenylacetamide, spiroxamine, quinoxyfen, fenhexamid, famoxadone, fenamidone (RP-407213), iprovalicarb, iminoctadine-triacetate, iminoctadine-albesilate, 6-iodo-3-propyl-2-propoxy-4(3H)-quinazolinone, (Z)-N-(α-cyclopropylmethoxyimino-2,3-difluoro-6-(trifluoro methyl)benzyl)-2-phenylacetamide, 2-chloro-N-(4'-chloro-(1,1'-biphenyl)-2-yl)-3-piridinecarboxamide, N-[2-(1,3-dimethylbutyl)-3-thienyl]-2,4-dimethylthiazole-5-carboxamide, N-[2-(1,3-dimethylbutyl)-3-thienyl]-3-trifluoromethyl-1-methylpyrazole-4-carboxamide and the like.

In the case of using the mixture of the compound of the invention and azole antifungal compound, the ratio of the compound of the invention to azole antifungal compound as the active ingredients is not limited to specific ratio; but when the ratio of azole antifungal compound to the compound of the invention by weight is 0.25 to 4, the excellent synergic effect can be achieved. In the case of using the mixture of the compound of the invention and cyclic amine antifungal compound, the ratio of the compound of the invention to cyclic amine antifungal compound as the active ingredients is not limited to specific ratio; but when the ratio of cyclic amine antifungal compound to the compound of the invention by weight is 1 to 8, the excellent synergic effect can be achieved. In the case of using the mixture of the compound of the invention and quinoxyfen, the ratio of the compound of the invention to quinoxyfen as the active ingredients is not limited to specific ratio; but when the ratio of quinoxyfen to the compound of the invention by weight is 0.25 to 2, the excellent synergic effect can be achieved. In the case of using the mixture of the compound of the invention and spiroxamine, the ratio of the compound of the invention to spiroxamine as the active ingredients is not limited to specific ratio; but when the ratio of spiroxamine to the compound of the invention by weight is 1 to 8, the excellent synergic effect can be achieved. In the case of using the mixture of the compound of the invention and ethylen bis (dithiocarbamate) compound, the ratio of the compound of the invention to ethylen bis(dithiocarbamate) compound as the active ingredients is not limited to specific ratio; but when the ratio of ethylen bis(dithiocarbamate) compound to the compound of the invention by weight is 1 to 20, the excellent synergic effect can be achieved. In the case of using the mixture of the compound of the invention and phthalimide compound, the ratio of the compound of the invention to phthalimide compound as the active ingredients is not limited to specific ratio; but when the ratio of phthalimide compound to the compound of the invention by weight is 1 to 20, the excellent synergic effect can be achieved. In the case of using the mixture of the compound of the invention and inorganic copper or organic copper, the ratio of the compound of the invention to inorganic copper or organic copper as the active ingredients is not limited to specific ratio; but when the ratio of inorganic copper or organic copper to the compound of the invention by weight is 1 to 20, the excellent synergic effect can be achieved. In the case of using the mixture of the compound of the invention and 6-iodo-3-propyl-2-propoxy-4(3H)-quinazolinone or (Z)-N-(α-cyclopropylmethoxyimino-2,3-difluoro-6-(trifluoromethyl)benzyl)-2-phenylacetamide, the ratio of the compound of the invention to 6-iodo-3-propyl-2-propoxy-4(3H)-quinazolinone or (Z)-N-(α-cyclopropylmethoxyimino-2,3-difluoro-6-(trifluoromethyl)benzyl)-2-phenylacetamide as the active ingredients is not limited to specific ratio; when the ratio of 6-iodo-3-propyl-2-propoxy-4(3H)-quinazolinone or (Z)-N-((-cyclopropylmethoxyimino-2,3-difluoro-6-(trifluoromethyl)benzyl)-2-phenylacetamide to the compound of the invention by weight is 0.1 to 4, the excellent synergic effect can be achieved. In the case of using the mixture of the compound of the invention and 2-chloro-N-(4'-chloro-(1,1'-biphenyl)-2-yl)-3-piridinecarboxamide, N-[2-(1,3-dimethylbutyl)-3-thienyl]-2,4-dimethylthiazole-5-carboxamide or N-[2-(1,3-dimethylbutyl)-3-thienyl]-3-trifluoromethyl-1-methylpyrazole-4-carboxamide, the ratio of the compound of the invention to 2-chloro-N-(4'-chloro-(1,1'-biphenyl)-2-yl)-3-piridinecarboxamide, N-[2-(1,3-dimethylbutyl)-3-thienyl]-2,4-dimethylthiazole-5-carboxamide or N-[2-(1,3-dimethylbutyl)-3-thienyl]-3-trifluoromethyl-1-methylpyrazole-4-carboxamide as the active ingredients is not limited to specific ratio; but when the ratio of 2-chloro-N-(4'-chloro-(1,1'-biphenyl)-2-yl)-3-piridinecarboxamide, N-[2-(1,3-dimethylbutyl)-3-thienyl]-2,4-dimethylthiazole-5-carboxamide or N-[2-(1,3-dimethylbutyl)-3-thienyl]-3-trifluoromethyl-1-methylpyrazole-4-carboxamide to the compound of the invention by weight is 0.2 to 5, the excellent synergic effect can be achieved.

6-Iodo-3-propyl-2-propoxy-4(3H)-quinazolinone is a compound described in WO94/26722, (Z)-N-(α-cyclopropylmethoxyimino-2,3-difluoro-6-(trifluoromethyl)benzyl)-2-phenylacetamide is a compound described in WO96/19442, 2-chloro-N-(4'-chloro-(1,1'-biphenyl)-2-yl)-3-piridinecarboxamide is a compound described in EP545099A, N-[2-(1,3-dimethylbutyl)-3-thienyl]-2,4-dimethylthiazole-5-carboxamide and N-[2-(1,3-dimethylbutyl)-3-thienyl]-3-trifluoromethyl-1-methylpyrazole-4-carboxamide are compounds JP-H09-235282-A.

The compound of the invention can be applied after mixed with other agricultural and horticultural insecticidal agent(s), acaricidal agent(s), nematocidal agent(s), herbicidal agent(s), plant growth controlling agent(s) or fertilizer (s). And also the compound of the invention can be applied at the same time without mixing it beforehand.

Examples of the insecticides and acaricides include: organophosphorus compounds such as fenitrothion [O,O-dimethyl O-(3-methyl-4-nitrophenyl)phosphorothioate], fenthion [O,O-dimethyl O-(3-methyl-4-(methythio)phenyl) phosphorothioate], diazinon [O,O-diethyl O-2-isopropyl-6-methylpyrimidin-4-yl phosphorothioate], chlorpyrifos [O,O-diethyl O-3,5,6-trichloro-2-pyridyl phosphorothioate], acephate [O,S-dimethyl acetylphosphoramidothioate], methidathion [S-2,3-dihydro-5-methoxy-2-oxo-1,3,4-thiadiazol-3-ylmethyl O,O-dimethylphosphorodithioate], disulfoton[O,O-diethylS-2-ethylthioethylphosphorothioate], DDVP [2,2-dichlorovinyl dimethyl phosphate], Sulprofos [O-ethyl O-4-(methylthio)phenyl S-propyl phosphorodithioate], cyanophos [O-4-cyanophenyl O,O-dimethyl phosphorothioate], dioxabenzofos [2-methoxy-4H-1,3,2-benzodioxaphosphinine-2-sulfide], dimethoate [O,O-dimethyl S-(N-methyl-carbamoylmethyl) dithiophosphate], phenthoate [ethyl 2-dimethoxyphosphinothioylthio(phenyl)acetate], malathion [diethyl (dimethoxyphosphinothioylthio)) succinate], trichlorfon [dimethyl 2,2,2-trichloro-1-hydroxyethyl-phosphonate], azinphos-methyl [S-3,4-dihydro-4-oxo-1,2,3-benzotriazin-3-ylmethyl O,O-dimethyl phosphorodithioate], monocrotophos [dimethyl (E)-1-methyl-2-(methylcarbamoyl)-vinylphosphate], ethion [O,O,O',O'-tetraethyl S,S'-methylenebis(phosphorodithioate)], phosphothiazate [N-(O-methyl-S-sec-butyl) phosphorylthiazolidine-2-one] and the like; carbamate compounds such as BPMC (2-sec-butylphenyl methylcarbamate), benfracarb [ethyl N-[2,3-dihydro-2,2-dimethylbenzofuran-7-yloxycarbonyl (methyl)aminothio]-N-isopropyl-β-alaninate], propoxur [2-isopropoxyphenyl N-methylcarbamate], Carbosulfan [2,3-dihydro-2,2-dimethyl-7-benzo[b]furanyl N-dibutylaminothio-N-methylcarbamate], carbaryl [1-naphthyl-N-methylcarbamate], methomyl [S-methyl-N-[(methylcarbamoyl)oxy]thioacetimidate], ethiofencarb [2-(ethylthiomethyl)phenylmethylcarbamate], aldicarb [2-methyl-2-(methylthio)propionaldehyde O-methylcarbamoyloxime], oxamyl [N,N-dimethyl-2-methyl-carbamoyloxyimino-2-(methylthio)acetamide], fenothiocarb [S-4-phenoxybutyl-N,N-dimethylthiocarbamate] and the like; pyrethroid compounds such as etofenprox [2-(4-ethoxyphenyl)-2-methylpropyl-3-phenoxybenzyl ether], fenvalerate [(RS)-α-cyano-3-phenoxybenzyl (RS)-2-(4-chlorophenyl)-3-methyl-butyrate], esfenvalerate [(S)-α-cyano-3-phenoxybenzyl (S)-2-(4-chlorophenyl)-3-methylbutyrate], fenpropathrin [(RS-α-cyano-3-phenoxybenzyl 2,2,3,3-tetramethylcyclopropanecarboxylate], cypermethrin [(RS)-α-cyano-3-phenoxybenzyl (1RS)-cis,trans-3-(2,2-dichlorovinyl)-2,2-dimethylcyclopropane-carboxylate], permethrin [3-phenoxybenzyl (1RS)-cis, trans-3-(2,2-dichlorovinyl)-2,2-dimethylcyclopropanecarboxylate], cyhalothrin [(RS)-α-cyano-3-phenoxybenzyl (Z)-(1RS)-cis-3-(2-chloro-3,3,3-trifluoroprop-1-enyl)-2,2-dimethylcyclopropanecarboxylate], deltamethrin [(S)-α-cyano-3-phenoxybenzyl (1R)-cis-3-(2,2-dibromovinyl)-2,2-dimethylcyclopropanecarboxylate], cycloprothrin [(RS)-α-cyano-3-phenoxybenzyl (RS)-2,2-dichloro-1-(4-ethoxyphenyl)cyclopropanecarboxylate], fluvalinate [α-cyano-3-phenoxybenzyl N-(2-chloro-α, α, α-trifluoro-p-tolyl)-D-valinate], bifenthrin [2-methyl-biphenyl-3-ylmethyl (Z)-(1RS)-cis-3-(2-chloro-3,3,3-tri-fluoroprop-1-enyl)-2,2-dimethyl-cyclopropanecarboxylate], acrinathrin [cyano-(3-phenoxyphenyl)methyl [1R-{1α(S*)-3α(Z)}]-2,2-dimethyl-3-[3-oxo-3-(2,2,2-trifluoro-1-(tri-fluoromethyl) ethoxy-1-propenyl)cyclopropanecarboxylate], 2-methyl-2-(4-bromodifluoromethoxyphenyl)propyl 3-phenoxybenzyl ether, tralomethrin [(S)-α-cyano-3-phenoxybenzyl (1R-cis)-3-{(1RS)(1,2,2,2-tetrabromoethyl)}-2,2-dimethyl-cyclopropanecarboxylate], silafluofen [(4-ethoxyphenyl)-{3-(4-fluoro-3-phenoxyphenyl)propyl} dimethylsilane] and the like; thiadiazine deribatives such as buprofezin [2-tert-butylimino-3-isopropyl-5-phenyl-1,3,5-triaziazinane-4-one]; nitroimidazolidine derivatives; nereistoxin derivatives such as cartap [S,S'-(2-dimethylaminotrimethylene) bis (thiocarbamate)], thiocyclam [N,N-dimethyl-1,2,3-trithian-5-ylamine], bensultap [S,S'-2-dimethylaminotrimethylene di (benzenethiosulfonate)] and the like;

N-cyanoamidine derivatives such as N-cyano-N'-methyl-N'-(6-chloro-3-pyridylmethyl)acetamidine and the like; chlorinated hydrocarbons such as endosulfan [6,7,8,9,10,10-hexachloro-1,5,5a,6,9,9a-hexahydro-6,9-methano-2,4,3-benzodioxathiepine oxide], γ-BHC [1,2,3,4,5,6-hexachlorocyclohexane], 1,1-bis(chlorophenyl)-2,2,2-trichloroethanol and the like; benzoylphenylurea compounds such as chlorfluazuron [1-(3,5-dichloro-4-(3-chloro-5-trifluoromethylpyridyn-2-yloxy)phenyl)-3-(2,6-difluorobenzoyl)urea], teflubenzuron [1-(3,5-dichloro-2,4-difluorophenyl)-3-(2,6-difluorobenzoyl)urea], flufenoxuron [1-(4-(2-chloro-4-trifluoromethylphenoxy)-2-fluorophenyl)-3-(2,6-difluorobenzoyl)urea and the like;

formamizine derivatives such as amitraz [N,N'-[(methylimino)dimethylidine]-di-2,4-xylidine], chlordimeform [N'-(4-chloro-2-methylphenyl)-N,N-dimethylmethinimidamide] and the like; thiourea derivatives such as diafenthiuron [N-(2,6-diisopropyl-4-phenoxyphenyl)-N'-tert-butylcarbodiimide] and the like; phenylpyrazole derivatives; tebfenozide [N-tert-butyl-N'-(4-ethylbenzoyl)-3,5-dimethylbenzohydrazide], bromopropylate [isopropyl 4,4'-dibromobenzylate], tetradifon [4-chlorophenyl 2,4,5-trichlorophenylsulfone], quinomethionate [S,S-6-methylquinoxaline-2,3-diyldithiocarbonate], propargate [2-(4-tert-butylphenoxy)cyclohexylprop-2-yl sulfite], fenbutatin oxide [bis[tris(2-methyl-2-phenylpropyl)tin] oxide], hexythiazox [(4RS,5RS)-5-(4-chlorophenyl)-N-chlorohexyl-4-methyl-2-oxo-1,3-thiazolidin e-3-carboxamide], chlofentezine [3,6-bis(2-chlorophenyl)-1,2,4,5-tetrazine], pyridathioben [2-tert-butyl-5-(4-tert-butylbenzylthio)-4-chloropyridazine-3(2H)-one], fenpyroximate [Lert-butyl (E)-4-[(1,3-dimethyl-5-phenoxypyrazol-4-yl)methyleneaminooxymethyl]-benzoate], tebfenpyrad [N-4-tert-butylbenzyl]-4-chloro-3-ethyl-1-methyl-5-pyrazolecarboxamide], polynactin complex [tetranactin, dinactin, trinactin], milbemectin, avermectin, ivermectin, azadilactin [AZAD], pyrimidifen [5-chloro-N-[2-{4-(2-ethoxyethyl)-2,3-dimethylphenoxy}ethyl]-6-ethylpyrimidine-4-amine], pymetrozine [2,3,4,5-tetrahydro-3-oxo-4-[(pyridin-3-yl) methyleneamino]-6-methyl-1,2,4-triazine] and the like.

The compound of the invention can control a variety of plant diseases, examples are described below: Blast (*Pyricularia oryzae*), *Helminthosporium* leaf spot (*Cochliobolus miyabeanus*) and sheath blight (*Rhizoctonia solani*) of rice plant; powderymildew (*Erysiphegraminis*), scab (*Gibberella zeae*), rust (*Puccinia striiformis, P. graminis, P. recondita, P. hordei*), snow blight (Typhula sp., *Micronectriella nivalis*), loose smut (*Ustilago tritici, U. nuda*), bunt (*Tilletia caries*), eyespot (*Pseudocercosporella herpotrichoides*), scald (*Rhynchosporium secalis*), leaf blight (*Septoria tritici*) and glume blotch (*Leptosphaeria nodorum*) of barley, wheat, oats and rye; melanose (*Diaporthe citri*), scab (*Elsinoe fawcetti*) and pencillium rot (*Penicillium digitatum, P. italicum*) of citrus; blossom blight (*Sclerotinla mali*), canker (*Valsa mali*), powdery mildew (*Podosphaera leucotricha*), Alternaria leaf spot (*Alternaria mali*) and scab (*Venturia inaequalis*) of apple; scab (*Venturia nashicola, V. pirina*), black spot (*Alternaria kikuchiana*) and rust (*Gymnosporangium haraeanum*) of pear; brown rot (*Sclerotinia cinerea*), scab (*Cladosporium carpophilum*) and Phomopsis rot (*Phomopsis sp.*) of peach; anthracnose (*Elsinoe-ampelina*), ripe rot (*Glomerella cingulata*), powdery mildew (*Uncinula necator*), rust (*Phakopsora ampelopsidis*), black rot (*Guignardia bidwellii*) and downy mildew (*Plasmopara viticola*) of grape; anthracnose (*Gloeosporium kaki*) and leaf spot (*Cercospora kaki, Mycosphaerella nawae*) of Japanese persimmon; anthracnose (*Colletotrichum lagenarium*), powdery mildew (*Sphaerotheca fuliginea*), gummy stem blight (*Mycosphaerella melonis*), stem rot (*Fusarium oxysporum*), downy mildew (*Pseudoperonospora cubensis*), late bright (*Phytophthora sp.*) and damping-off (*Pythium sp.*) of melons and cucumbers; early blight (*Alternaria solani*), leaf mold (*Cladosporium fulvum*) and late blight (*Phytophthora infestans*) of tomato; brown spot (*Phomopsis vexans*) and powdery mildew (*Erysiphe cichoracearum*) of eggplant; altenaria leaf spot (*Alternaria japonica*) and white spot (*Cercosporella brassicae*) of vegetables of Cruciferae; Welsh onion rust (*Puccinia allii*); purple stain (*Cercospora kikuchii*), Sphaceloma scab (*Elsinoe glycines*) and pod and stem blight (*Diaporthe phaseolorum* var. sojae) of soybean; kidney bean anthracnose (*Colletotrichum lindemthianum*); early leaf spot (*Cercospora personata*) and leaf spot (*Cercospora arachidicola*) of peanut; pea powdery mildew (*Erysiphe pisi*); early blight (*Alternaria solani*) and late blight (*Phytophthora infestans*) of potato; strawberry powdery mildew (*Sphaerotheca humuli*); net blister blight (*Exobasidium reticulatum*) and white scab (*Elsinoe leucospila*) of tea plant; brown spot (*Alternaria longipes*), powdery mildew (*Erysiphe cichoracearum*) anthracnose (*Colletotrichum tabacum*), downy mildew (*Peronospora tabacina*) and (*Phytophthora nicotianae*) of tobacco; beet leaf spot (*Cercospora beticola*); black spot (*Diplocarpon rosae*) and powdery mildew (*Sphaerotheca pannosa*) of rose; leaf spot (*Septoria chrysanthemi-indici*) and white rust (*Puccinia horiana*) of chrysanthemum; gray mold (*Botrytis cinerea*) and stem rot (*Sclerotinia sclerotiorum*) of various crops and the like.

EXAMPLES

The following production examples, formulation examples and test examples and the like describe the invention further in detail below, but do not limit the scope of the invention.

First, production examples of compounds of the invention and production examples of intermediates for the production are shown by Production Examples, Reference Production Examples and Intermediate Production Examples. The numbers of compounds of the invention are indicated by compound numbers described in Tables 1 to 17 described below.

Production Example 1

0.50 g (1.63 mmol) of 5-formyl-2-methyl-4-(2-methyl-5-phenylbenzyl)-2,4-dihydro-3H-1,2,4-triazol-3-one (produced by the same manner as in Reference Production Example 1) was added to 4 ml of chloroform, and to this was added 0.79 g (4.91 mmol) of diethylaminosulfur trifluoride under ice cooling. Then, the mixture was stirred at room temperature overnight. The reaction solution was washed with a 5 wt % sodium bicarbonate solution, then, the organic layer was dried over anhydrous magnesium sulfate, and concentrated to obtain 0.54 g (1.63 mmol) of 5-difluoromethyl-2-methyl-4-(2-methyl-5-phenylbenzyl)-2,4-dihydro-3H-1,2,4-triazol-3-one (Compound 1) having a melting point of 72.7° C.

$^1$H-NMR (CDCl$_3$, TMS) δ (ppm): 7.15–7.55 (8H, m), 6.33 (1H, t), 5.04 (2H, s), 3.54 (3H, s), 2.40 (3H, s)

Reference Production Example 1

(1) 117 g (998 mmol) of 2-methylbenzonitrile was dropped to 1000 g of a Na-X type zeolite dried powder (Zeolam type F-9 manufactured by Toyo Corp.; 100 mesh or less) while stirring under air cooling. The resulted mixed was allowed to cool, and after cooled to 50° C. or lower, to this was added 213 g (1.33 mol) of bromine, and the mixture was stirred at 80 to 85° C. for 1.5 hours, then, cooled to 15° C. or lower. This was added into mixture of 100 g of potassium carbonate, 500 ml of water and 2 L of methanol at 10° C. or lower. The mixture was stirred for 0.5 hours, then, filtrated. The filtrated residue, zeolite powder was washed with 90% methanol water (2.2L×2), the filtrate and washed solution were combined, and concentrated until the total liquid quality reached 750 ml. The resulted while crystal was filtrated, and the crystal was washed with water to obtain 162 g (826 mmol) of 5-bromo-2-methylbenzonitrile.

$^1$H-NMR (CDCl$_3$, TMS) δ (ppm): 7.68 (1H, d), 7.59 (1H, dd), 7.20 (1H, d), 2.50 (3H, s)

(2) A mixture of 27.4 g (140 mmol) of 5-bromo-2-methylbenzonitrile, 19.5 g (160 mmol) of dihydroxyphenylborane, 629 mg (2.8 mmol) of palladium acetate (II), 45.1 g (140 mmol) of tetrabutylammonium bromide, 48.4 g (350 mmol) of potassium carbonate and 280 ml of water was stirred at 75° C. for 11 hours under nitrogen flow. To the reaction solution was added chloroform, the organic layer was washed with water, dried over anhydrous magnesium sulfate, then, concentrated. The residue was re-crystallized from methanol to give 19.9 g (99.9 mmol) of 2-methyl-5-phenylbenzonitrile.

$^1$H-NMR (CDCl$_3$, TMS) δ (ppm): 7.35–7.78 (8H, m), 2.59 (3H, s)

(3) Under nitrogen atmosphere, 126 g (650 mmol) of 2-methyl-5-phenylbenzonitrile was dissolved in 700 ml of anhydrous toluene, and to the resulted solution was dropped 780 ml of a toluene solution of diisobutyl aluminum hydride (1.0 M solution; 780 mmol) at –10 to 0° C., and the mixture was stirred at room temperature overnight. To the reaction solution was dropped 25 ml of ethyl acetate, and this was poured into a mixture of 2.5 L of ice water and 270 ml of concentrated hydrochloric acid. After stirring at 70 to 75° C. for 1 hour, the mixture was cooled to room temperature, and separated. The organic layer was washed with water, saturated sodium bicarbonate solution, then, water, and concentrated to obtain 123 g of 2-methyl-5-phenylbenzaldehyde.

1H-NMR (CDCl$_3$, TMS) δ (ppm): 10.36 (1H, s), 7.30–8.08 (8H, m), 2.72 (3H, s)

(4) 123 g (625 mmol) of 2-methyl-5-phenylbenzaldehyde was dissolved in a mixture of 1.1 L of tetrahydrofuran and 110 ml of water, and to the resulted solution was dropped, at 15 to 20° C., a solution prepared by dissolving 7.7 g (203 mmol) of sodium boron hydride in 70 ml of a 0.1 wt % sodium hydroxide aqueous solution. After completion of dropping, the mixture was stirred for 4 hours at 15 to 20° C. To this reaction solution was dropped 10 g of glacial acetic acid at 20° C. or lower, and this was poured into ice water. The reaction solution was extracted with t-butyl methyl ether, the organic layer was washed with water, saturated sodium bicarbonate solution, then, saturated saline, dried over anhydrous magnesium sulfate, then, concentrated to obtain 121 of 2-methyl-5-phenylbenzyl alcohol.

$^1$H-NMR (CDCl$_3$, TMS) δ (ppm): 7.20–7.65 (8H, m), 4.74 (2H, s), 2.38 (3H, s), 1.71 (1H, br)

(5) 14.9 g (75.0 mmol) of 2-methyl-5-phenylbenzyl alcohol was dissolved in 100 ml of anhydrous diethyl ether, and to the resulted solution was dropped 8.12 g (30.0 mmol) of phosphorus tribromide under ice cooling. The mixture was stirred further for 3 hours under ice cooling, then, to the reaction solution was added ice water and t-butyl methyl ether, the mixture was stirred for 30 minutes, then, separated. The organic layer was washed with an about 5 wt % sodium bicarbonate solution and water sequentially, dried over anhydrous magnesium sulfate, then, concentrated to obtain 19.2 g (73.7 mmol) of 2-methyl-5-phenylbenzyl bromide.

$^1$H-NMR (CDCl$_3$, TMS) δ (ppm): 7.20–7.65 (8H, m), 4.57 (2H; s), 2.45 (3H, s)

(6) 7.83 g (30 mmol) of 2-methyl-5-phenylbenzyl bromide was dissolved in 90 ml of anhydrous tetrahydrofuran, and to this was added 5.84 g (39 mmol) of silver cyanide, and the mixture was heated under reflux for 2 hours. The reaction solution was filtrated, and the filtrate was concentrated to obtain 7.11 g of crude 2-methyl-5-phenylbenzyl isocyanate.

$^1$H-NMR (CDCl$_3$, TMS) δ (ppm): 7.25–7.65 (8H, m), 4.53 (2H, s), 2.37 (3H, s)

(7) 14.9 g of crude 2-methyl-5-phenylbenzyl isocyanate was added to 50 ml of toluene, and to the resulted suspension was added 6.01 g (66.7 mmol) of 2-hydroxyacetohydrazide, and the mixture was stirred at 60° C. for 1 hour. After cooling to room temperature, the reaction solution was concentrated, and to the residue was added ethanol to precipitate a crystal, obtaining 13.8 g (44.0 mmol) of 1-hydroxyacetyl-4-(2-methyl-5-phenylbenzyl) semicarbazide.

$^1$H-NMR (DMSO-d$_6$) δ (ppm): 9.47 (1H, br), 7.10–7.90 (8H, m), 6.83 (1H, br), 5.32 (1H, br), 4.26 (2H, d), 3.91 (2H, d), 2.29 (3H, s)

(8) 13.8 g (44.0 mmol) of 1-hydroxyacetyl-4-(2-methyl-5-phenylbenzyl) semicarbazide was added to 100 ml of a 2 wt % potassium hydroxide aqueous solution, and the mixture was stirred at 90° C. for 2 hours. After cooling to room temperature, the reaction solution was extracted with ethyl acetate, the organic layer was washed with water, dried over anhydrous magnesium sulfate, then, concentrated. The residue was subjected to silica gel column chromatography (eluant: ethyl acetate), to obtain 12.0 g (40.6 mmol) of 5-hydroxymethyl-4-(2-methyl-5-phenylbenzyl)-2,4-dihydro-3H-1,2,4-triazol-3-one.

$^1$H-NMR (CDCl$_3$, TMS)
δ (ppm): 7.15–7.60 (8H, m), 5.17 (1H, t), 5.02 (2H, s), 4.28 (2H, d), 2.40 (3H, s)

(9) 6.29 g (21.3 mmol) of 5-hydroxymethyl-4-(2-methyl-5-phenylbenzyl)-2,4-dihydro-3H-1,2,4-triazol-3-one, 3.53 g (25.6 mmol) of potassium carbonate and 3.63 g (25.6 mmol) of methyl iodide were stirred for 4 hours at 60° C. in 38 mol of anhydrous N,N-dimethylformamide. To the reaction solution was added 200 ml of a 5 wt % hydrochloric acid aqueous solution, and this was extracted with ethyl acetate. The organic layer was washed with water, 5 wt % sodium bicarbonate solution, then, saturated saline, dried over anhydrous magnesium sulfate, then, concentrated. The residuie was subjected to silica gel column chromatography (eluant: hexane/ethyl acetate=1/1 (v/v), then, ethyl acetate), to obtain 6.52 g (21.2 mmol) of 5-hydroxymethyl-2-methyl-4-(2-methyl-5-phenylbenzyl)-2,4-dihydro-3H-1,2,4-triazol-3-one.

$^1$H-NMR (CDCl$_3$, TMS) δ (ppm): 7.20–7.65 (8H, m), 5.00 (2H, s), 4.29 (2H, d), 3.48 (3H, s), 2.37 (3H, s)

(10) 6.52 g (21.2 mmol) of 5-hydroxymethyl-2-methyl-4-(2-methyl-5-phenylbenzyl-)2,4-dihydro-3H-1,2,4-triazol-3-o ne and 14 g of active manganese dioxide were stirred for 6 hours in nitrogen atmosphere under reflux with heating in 63 ml of chloroform. The reaction solution was filtrated through celite, and the filtrate was concentrated. The residue was subjected to silica gel column chromatography (eluant:hexane:ethyl acetate=1:1), to obtain 4.32 g (14.1 mmol) of 5-formyl-2-methyl-4-(2-methyl-5-phenylbenzyl)-2,4-dihydro-3H-1,2,4-triazol-3-one.

$^1$H-NMR (CDCl$_3$, TMS) δ (ppm): 9.49 (1H, s), 7.10–7.52 (8H, m), 5.25 (2H, s), 3.63 (3H, s), 2.47 (3H, s)

Production Example 2

5.04 g (16.2 mmol) of 4-(5-bromo-2-methylbenzyl)-5-formyl-2-methyl-2,4-dihydro-3 H-1,2,4-triazol-3-one (produced in the same manner as in Reference Production Example 2) was dissolved in 40 ml of chloroform, to this was added 7.8 g (48.4 mmol) of diethylaminosulfur trifluoride under ice cooling. Then, the mixture was stirred at room temperature overnight. The reaction solution was washed with a 5 wt % sodium bicarbonate solution, then, the organic layer was dried over anhydrous magnesium sulfate, and concentrated. The residue was subjected to silica gel column chromatography (eluant: hexane/ethyl acetate=1/2 (v/v)), to obtain 5.04 g (15.2 mmol) of 4-(5-bromo-2-methylbenzyl)-5-difluoromethyl-2-methyl-2,4-dihydro-3H-1,2,4-triazol-3-one (Compound 40) having a melting point of 107.6° C.

$^1$H-NMR (CDCl$_3$, TMS)
δ (ppm): 7.32 (1H, dd), 7.06 (1H, brs), 7.05 (1H, d), 6.36 (1H, t), 4.94 (2H, s), 3.55 (3H, s), 2.32 (3H, s)

Reference Production Example 2

(1) 81.7 g (417 mmol) of 5-bromo-2-methylbenzonitrile (produced in the same manner as in (1) of Reference Production Example 1) was dissolved in 500 ml of anhydrous toluene under nitrogen atmosphere, to the resulted solution was dropped 500 ml (500 mmol) of toluene solution (1.0 M) of diisobutyl aluminum hydride at from −10 to 0° C., and the mixture was stirred atom room temperature overnight. To the reaction solution was dropped ethyl acetate, and this was poured into a mixture of 2 L of ice water and 170 ml of concentrated hydrochloric acid. After stirring at 70 to 75° C. for 1 hour, then, the mixture was cooled to room temperature, and separated. The organic layer was washed with water, saturated sodium bicarbonate solution, then, water, and concentrated to obtain 80.4 g of 5-bromo-2-methylbenzaldehyde.

$^1$H-NMR (CDCl$_3$, TMS)
δ (ppm): 10.2 (1H, s), 7.91 (1H, d), 7.58 (1H, dd), 7.15 (1H, d), 2.62 (3H, s)

(2) 161.2 g (810 mmol) of 5-bromo-2-methylbenzaldehyde was dissolved in 1.5 L of tetrahydrofuran and 150 ml of water, and to the resulted solution was dropped, at 15 to 20° C., a solution prepared by dissolving 10.0 g (264 mmol) of sodium boron hydride in 100 ml of a 0.1 wt % sodium hydroxide aqueous solution. After completion of dropping, the mixture was stirred at 15 to 20° C. for 4 hours. To the reaction solution was dropped 12.0 g of glacial acetic acid at 20° C. or lower, then, this was poured into ice water. The reaction solution was extracted with t-butyl methyl ether, the organic layer was washed with water, further washed twice with a saturated sodium bicarbonate solution, then, washed with saturated saline, and dried over anhydrous magnesium sulfate, then, concentrated to obtain 168 g of 5-bromo-2-methylbenzyl alcohol.

$^1$H-NMR (CDCl$_3$, TMS) δ (ppm): 7.50 (1H, d), 7.30 (1H, dd), 7.00 (1H, d), 4.62 (2H, d), 2.25 (3H, s), 2.08 (1H, t)

(3) 24.4 g (121 mmol) of 5-bromo-2-methylbenzyl alcohol was dissolved in 200 ml of anhydrous diethyl ether, and to the resulted solution was dropped 16.4 g (60.7 mmol) of phosphorus tribromide under ice cooling. The mixture was stirred further for 3 hours under ice cooling, then, the reaction solution was poured into ice water, then, separated. The organic layer was washed with water, saturated sodium bicarbonate solution and saline sequentially, dried over anhydrous magnesium sulfate, then, concentrated to obtain 29.1 g (110 mmol) of 5-bromo-2-methylbenzyl bromide in the form of brown solid.

$^1$H-NMR (CDCl$_3$, TMS) δ (ppm): 7.44 (1H, d), 7.33 (1H, dd), 7.05 (1H, d), 4.43 (2H, s), 2.35 (3H, s)

(4) 23.4 g (88.8 mmol) of 5-bromo-2-methylbenzyl bromide was dissolved in 100 ml of anhydrous tetrahydrofuran, and to this was added 16.0 g (106 mmol) of silver cyanide, and the mixture was heated under reflux for 2 hours. The reaction solution was filtrated, and the filtrate was concentrated to obtain crude 5-bromo-2-methylbenzyl isocyanate. This was mixed with 100 ml of toluene and 8.0 g (88.8 mmol) of 2-hydroxyacetohydrazide, and the mixture was stirred at 60° C. for 2 hours. After cooling to the room temperature, the reaction solution was concentrated, to the residue was added ethanol to precipitate a crystal, obtaining 18.1 g (57.2 mmol) of 4-(5-bromo-2-methylbenzyl)-1-hydroxyacetyl semicarbazide.

$^1$H-NMR (DMSO-d$_6$) δ (ppm): 9.46 (1H, br), 7.85 (1H, br), 7.02–7.65 (3H, m), 6.85 (1H, br), 5.30 (1H, br), 4.16 (2H, d), 3.90 (2H, d), 2.20 (3H, s)

(5) 18.0 g (56.9 mmol) of 4-(5-bromo-2-methylbenzyl)-1-hydroxyacetyl semicarbazide was added to 170 ml of a 2 wt % potassium hydroxide aqueous solution, and the mixture was stirred at 90° C. for 2 hours. After cooling to the room temperature, the reaction solution was made acidic by addition of hydrochloric acid, and the solution was filtrated to obtain white solid. The filtrate was extracted with ethyl acetate, the organic layer was washed with water, dried over anhydrous magnesium sulfate, then, concentrated to obtain white solid. This was combined with the previously obtained white solid and dried under reduced pressure, to obtain 12.3 g (41.2 mmol) of 4-(5-bromo-2-methylbenzyl)-5-hydroxymethyl-2,4-dihydro-3H-1,2,4-triazol-3-one.

$^1$H-NMR (DMSO-d$_6$) δ (ppm): 7.34 (1H, dd), 7.16 (1H, d), 6.95 (1H, d), 5.53 (1H, br), 4.81 (2H, s), 4.20 (2H, br), 2.27 (3H, s)

(6) 7.16 g 624.0 mmol) of 4-(5-bromo-2-methN71benzyl)-5-hydroxymethyl-2,4-dihydro-3H-1,2,4-triazol-3-one, 3.98 g (28.8 mmol) of potassium carbonate and 4.09 g (28.8 mmol) of methyl iodide were stirred at 60° C. for 4 hours in 45 mml of anhydrous N,N-dimethylformamide. To the reaction solution, 300 ml of a 5 wt % hydrochloric acid aqueous solution was added, and the mixture was extracted with ethyl acetate. The organic layer was washed with water, 5 wt % sodium bicarbonate solution, then, saturated saline, and dried over anhydrous magnesium sulfate, then, concentrated to obtain 7.46 g (23.9 mmol) of 4-(5-bromo-2-methylbenzyl)-5-hydroxymethyl-2-methyl-2,4-dihydro-3H-1,2,4-triazol-3-one.

$^1$H-NMR (CDCl$_3$, TMS) δ (ppm): 7.33 (1H, dd), 7.11 (1H, d), 7.05 (1H, d), 4.91 (2H, s), 4.32 (2H, s), 3.49 (3H, s), 2.62 (1H, br), 2.29 (3H, s)

(7) 7.46 g (23.9 mmol) of 4-(5-bromo-2-methylbenzyl)-5-hydroxymethyl-2-methyl-2,4-dihydro-3H-1,2,4-triazol-3-one and 15.8 g of active manganese dioxide were stirred for 3 hours in nitrogen atmosphere under reflux with heating in 71 ml of chloroform. The reaction solution was filtrated through celite, and the filtrate was concentrated. The residue was subjected to silica gel column chromatography (eluant: hexane/ethyl acetate-1/2 (v/v)), to obtain 5.04 g (16.3 mmol) of 4-(5-bromo-2-methylbenzyl)-5-formyl-2-methyl-2,4-dihydro-3H-1,2,4-triazol-3-one having a melting point of 107.5° C.

$^1$H-NMR (CDCl$_3$, TMS) δ (ppm): 9.49 (1H, s), 7.28 (1H, dd), 7.04 (1H, d), 6.97 (1H, d), 5.15 (2H, s), 3.66 (3H, s), 2.38 (3H, s)

Production Example 3

0.16 g (1.18 mmol) of 4-methylphenylboronic acid, 355 mg (1.07 mmol) of 4-(5-bromo-2-methylbenzyl)-5-difluoromethyl-2-methyl-2,4-dihydro-3H-1,2,4-triazol-3-one (Compound 40; produced by the same method as in Production Example 2), 2 mg (0.008 mmol) of palladium acetate, 0.37 g (2.68 mmol) of potassium carbonate and 0.34 g (1.07 mmol) of tetrabutylammonium bromide were suspended in 5 ml of water, and stirred vigorously under nitrogen flow, then, reacted at a bath temperature of 75° C. for 1 hour under nitrogen atmosphere. Water was added the reaction mixture which was then extracted with ethyl acetate, the organic layer was dried over anhydrous magnesium sulfate, then, concentrated. 0.39 g of the residue was subjected to silica gel thin layer chromatography (eluant: toluene/ethyl acetate=4/1 (v/v), to obtain 0.33 g of 4-{2-methyl-5-(4-methylphenyl)benzyl}-5-difluoromethyl-2-metyl-2,4-dihydro-3H-1,2,4-triazol-3-one (Compound 4) in the form of oil.

$^1$H-NMR (CDCl$_3$, TMS) δ (ppm): 7.1–7.5 (7H, m), 6.32 (1H, t) 5.03 (2H, s), 3.53 (3H, s), 2.39 (3H, s), 2.38 (3H, s)

Production Example 4

175 mg (1.29 mmol) of 2-fluorophenylboronic acid, 285 mg (0.859 mmol) of 4-(5-bromo-2-methylbenzyl)-5-difluoromethyl-2-methyl-2,4-dihydro-3H-1,2,4-triazol-3-one (Compound 40; produced in the same manner as in Production Example 2), 1.06 g of tripotassium phosphate hydrate and 35 mg (0.043 mmol) of [1,1'-bis(diphenylphosphono)ferrocene]dichloropalladium (II) methylene chloride complex were suspended in 10 ml of 1,2-dimethoxyethane, and stirred for 2 hours in nitrogen atmosphere under reflux with heating. Ethyl acetate was added to the reaction solution and the mixture was filtrated through celite, then, the filtrate was concentrated. 0.43 g of the residue was subjected to silica gel thin layer chromatography (eluant: toluene/ethyl acetate=4/1 (v/v)), to obtain 0.29 g of 5-difluoromethyl-4-{5-(2-fluorophenyl)-2-methylbenzyl}-2-methyl-2,4-dihydro-3H-1,2,4-triazol-3-one (Compound 18) in the form of oil.

$^1$H-NMR (CDCl$_3$, TMS) δ (ppm): 7.05–7.45 (7H, m), 6.34 (1H, t), 5.03 (2H, s), 3.54 (3H, s), 2.40 (3H, s)

Production Example 5

175 mg (1.29 mmol) of 3-fluorophenylboronic acid, 285 mg (0.859 mmol) of 4-(5-bromo-2-methylbenzyl)-5-difluoromethyl-2-methyl-2,4-dihydro-3H-1,2,4-triazol-3-one (Compound40; produced in the same manner as in Production Example 2), 1.06 g of tripotassium phosphate hydrate and 35 mg (0.043 mmol) of [1,1'-bis(diphenylphosphono)ferrocene]-dichloropalladium (II) methylene chloride complex were suspended in 10 ml of 1,2-dimethoxyethane, and stirred for 2 hours in nitrogen atmosphere under reflux with heating. Ethyl acetate was added to the reaction mixture and the mixture was filtrated through celite, then, the filtrate was concentrated. 0.43 g of the residue was subjected to silica gel thin layer chromatography (eluant: toluene/ethyl acetate=4/1 (v/v)), to obtain 0.28 g of 5-difluoromethyl-4-{5-(3-fluorophenyl)-2-methylbenzyl}-2-methyl-2,4-dihydro-3H-1,2,4-triazol-3-one (Compound 19) in the form of oil.

$^1$H-NMR (CDCl$_3$, TMS) δ (ppm): 7.15–7.45 (6H, m), 7.00 (1H, dt), 6.36 (1H, t), 5.04 (2H, s), 3.55 (3H, s), 2.41 (3H, s)

Production Example 6

175 mg (1.29 mmol) of 4-fluorophenylboronic acid, 285 mg (0.859 mmol) of 4-(5-bromo-2-methylbenzyl)-5-difluoromethyl-2-methyl-2,4-dihydro-3H-1,2,4-triazol-3-one (Compound 40; produced in the same manner as in Production Example 2), 1.06 g of tripotassium phosphate hydrate and 35 mg (0.043 mmol) of [1,1'-bis(diphenylphosphono)ferrocene]dichloropalladium (II) methylene chloride complex were suspended in 10 ml of 1,2-dimethoxyethane, and stirred for 2 hours in nitrogen atmosphere under reflux with heating. Ethyl acetate was added to the reaction mixture and the mixture was filtrated through celite, then, the filtrate was concentrated. 0.43 g of the residue was subjected to silica gel thin layer chromatography (eluant: toluene/ethyl acetate=4/1 (v/v)), to obtain 0.29 g of 5-difluoromethyl-4-{5-(4-fluorophenyl)-2-methylbenzyl}-2-methyl-2,4-dihydro-3H-1,2,4-triazol-3-one (Compound 20) in the form of oil.

$^1$H-NMR (CDCl$_3$, TMS) δ (ppm): 7.05–7.5 (7H, m), 6.36 (1H, t), 5.03 (2H, s), 3.54 (3H, s), 2.40 (3H, s)

Production Example 7

200 mg (0.527 mmol) of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one (produced in the same manner as in Reference Production Example 3), 124 mg (0.683 mmol) of 2-chloro-6-trifluoromethylpyridine, 560 mg (2.64 mmol) of tripotassium phosphate hydrate, 22 mg (0.027 mmol) of {1,1'-bis(diphenylphosphino)ferrocene}-dichloropalladium (II) methylene chloride complex and 3.0 ml of ethylene glycol dimethyl ether were mixed and stirred at 80° C. for 3 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 183 mg of 5-difluoromethyl-2-methyl-4-{2-methyl-5-(6-trifluoromethyl-2-pyrodyl)benzyl-2,4-dihydro-3H-1,2,4-triazol-3-one (Compound 329) in the form of pale yellow powder.

$^1$H-NMR (CDCl$_3$, TMS) δ (ppm): 7.8–7.9 (3H, m), 7.72 (1H, s), 7.56 (1H, d), 7.42 (1H, d), 6.36 (1H, t), 5.06 (2H, s), 3.55 (3H, s), 2.44 (3H, s)

Reference Production Example 3

1.00 g (3.01 mmol) of 4-(5-bromo-2-methylbenzyl)-5-difluoromethyl-2-methyl-2,4-dihydro-3H-1,2,4-triazol-3-one (Compound 40; produced in the same manner as in Production Example 2), 0.99 g (3.90 mmol) of bis(pinacolate)diboron, 0.12 g (0.15 mmol) of {1,1'-bis(diphenylphosphino)ferrocene}-dichloropalladium (II) methylene chloride complex, 0.89 g (9.07 mmol) of potassium acetate and 20 ml of dimethyl sulfoxide were mixed, and stirred at 80° C. for 8 hours. The mixture was cooled to room temperature, water added to this, and the mixture was extracted with ethyl acetate. The organic layer was washed with water, washed with saturated saline, and dried over anhydrous magnesium sulfate, then, a small amount of hexane was added to this and the mixture was left at 0° C. for 3 days. The precipitated crystal was ground, then, filtrated, and washed with hexane, to obtain 1.12 g of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one in the form of brown powder.

$^1$H-NMR (CDCl$_3$, TMS) δ (ppm): 7.66 (1H, d), 7.45 (1H, s), 7.19 (1H, d), 6.21 (1H, t), 4.98 (2H, s), 3.55 (3H, s), 2.34 (3H, s), 1.31 (12H, s)

Production Example 8

200 mg (0.527 mmol) of 5-difluoromethyl-2-methyl-4-{2-methyl-5-(4,4,5,5-tetramethyl-1,3,2-dioxobororan-2-yl)benzylj-2,4-dihydro-3H-1,2,4-triazol-3-one (produced in the same manner as in Reference Production Example 3), 98 mg (0.683 mmol) of 2-chloro-6-methoxypyridine, 560 mg (2.64 mmol) of tripotassium phosphate hydrate, 22 mg (0.027 mmol) of {1,1'-bis(diphenylphosphino)ferrocene}dichloropalladium (II) methylene chloride complex and 3.0 ml of ethylene glycol dimethyl ether were mixed, then stirred at 80° C. for 3 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 170 mg of 5-difluoromethyl-2-methyl-4-{2-methyl-5-(6-methoxy-2-pyridyl)benzyl}-2,4-dihydro-3H-1,2,4-triazol-3-one (Compound 120) in the form of pale yellow liquid.

$^1$H-NMR (CDCl$_3$, TMS) δ (ppm): 7.90 (1H, dd), 7.77 (1H, s), 7.58 (1H, t), 7.2–7.3 (2H, m), 6.65 (1H, d), 6.35 (1H, t), 5.05 (2H, s), 3.98 (3H, s), 3.54 (3H, s), 2.42 (3H, s).

Production Example 9

200 mg (0.527 mmol) of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one (produced in the same manner as in Reference Production Example 3), 112 mg (0.687 mmol) of 3-bromo-thiophene, 560 mg (2.64 mmol) of tripotassium phosphate hydrate, 22 mg (0.027 mmol) of {1,1'-bis(diphenylphosphino)ferrocene}dichloropalladium (II) methylene chloride complex and 3.0 ml of ethylene glycol dimethyl ether were mixed, and stirred at 80° C. for 2 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography feluant: hexane/ethyl acetate=1/1 (v/v, addition of 1 vol % methanol)}, to obtain 146 mg of 5-difluoromethyl-2-methyl-4-{2-methyl-5-(3-thienyl)benzyl}-2,4-dihydro-3H-1,2,4-triazol-3-one (Compound 105) in the form of white powder.

$^1$H-NMR (CDCl$_3$, TMS) δ (ppm): 7.42 (1H, dd), 7.2–7.4 (5H, m), 6.33 (1H, t), 5.02 (2H, s), 3.55 (3H, s), 2.38 (3H, s)

Production Example 10

200 mg (0.527 mmol) of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one (produced in the same manner as in Reference Production Example 3), 107 mg (0.793 mmol) of 2-bromo-bis-2-butene, 560 mg (2.64 mmol) of tripotassium phosphate hydrate, 22 mg (0.027 mmol) of {1,1'-bis(diphenylphosphino)ferrocene}dichloropalladium (II) methylene chloride complex and 3.0 ml of ethylene glycol dimethyl ether were mixed, then stirred at 70° C. for 2 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 123 mg of 5-difluoromethyl-2-methyl-4-{2-methyl-5-((E)-1-methyl-1-propenyl)benzyl}-2,4-dihydro-3H-1,2,4-triazol-3-one (Compound 47) in the form of pale yellow powder.

$^1$H-NMR (CDCl$_3$, TMS) δ (ppm): 7.19–7.21 (1H, m), 7.10 (1H, d), 7.00 (1H, s), 6.27 (1H, t), 5.72–5.78 (1H, m), 4.97 (2H, s), 3.54 (3H, s), 2.33 (3H, s), 1.95 (3H, s), 1.76 (3H, d)

Production Example 11

200 mg (0.527 mmol) of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one (produced in the same manner as in Reference Production Example 3), 117 mg (0.676 mmol) of 2-bromo-4-methylpyrimidine, 560 mg (2.64 mmol) of tripotassium phosphate hydrate, 22 mg (0.027 mmol) of {1,1'-bis(diphenylphosphino)ferrocene}dichloropalladium (II) methylene chloride complex and 3.0 ml of ethylene glycol dimethyl ether were mixed, then stirred at 80° C. for 3 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 144 mg of 5-difluoromethyl-2-methyl-4-{2-methyl-5-(4-methyl-2-pyrimidinyl)benzyl}-2,4-dihydro-3H-1,2,4-triazol-3-one (Compound 343) in the form of pale yellow solid.

$^1$H-NMR (CDCl$_3$, TMS) δ (ppm): 8.59 (1H, d), 8.30 (1H, dd), 8.16 (1H, s), 7.30 (1H, d), 7.01 (1H, d), 6.29 (1H, t), 5.06 (2H, s), 3.56 (3H, s), 2.55 (3H, s), 2.41 (3H, s)

Production Example 12

200 mg (0.527 mmol) of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one (produced in the same manner as in Reference Production Example 3), 156 mg (0.743 mmol) of 2-iodothiophene, 560 mg (2.64 mmol) of tripotassium phosphate hydrate, 22 mg (0.027 mmol) of {1,1'-bis(diphenylphosphino)ferrocene}dichloropalladium (II) methylene chloride complex and 3.0 ml of ethylene glycol dimethyl ether were mixed, then stirred at 80° C. for 2 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 149 mg of 5-difluoromethyl-2-methyl-4-{2-methyl-5-(2-thienyl)benzyl}-2,4-dihydro-3H-1,2,4-triazol-3-one (Compound 104) in the form of white powder.

$^1$H-NMR (CDCl$_3$, TMS) δ (ppm): 7.44 (1H, dd), 7.2–7.3 (4H, m), 7.03–7.06 (1H, m), 6.34 (1H, t), 5.01 (2H, s), 3.55 (3H, s), 2.38 (3H, s)

Production Example 13

200 mg (0.527 mmol) of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one (produced in the same manner as in Reference Production Example 3), 112 mg (0.683 mmol) of 2-bromothiazole, 560 mg (2.64 mmol) of tripotassium phosphate hydrate, 22 mg (0.027 mmol) of {1,1'-bis(diphenylphosphino)ferrocene}dichloropalladium (II) methylene chloride complex and 3.0 ml of ethylene glycol dimethyl ether were mixed, then stirred at 80° C. for 2 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 120 mg of 5-difluoromethyl-2-methyl-4-{2-methyl-5-(2-thiazolyl)benzyl}-2,4-dihydro-3H-1,2,4-triazol-3-one (Compound 113) of pale yellow appearance.

$^1$H-NMR (CDCl$_3$, TMS) δ (ppm): 7.78–7.83 (2H, m), 7.63 (1H, s), 7.25–7.29 (2H, m), 6.35 (1H, t), 5.03 (2H, s), 3.56 (3H, s), 2.41 (3H, s)

Production Example 14

332 mg (1.00 mmol) of 4-(5-bromo-2-methylbenzyl)-5-difluoromethyl-2-methyl-2,4-dihydro-3H-1,2,4-triazol-3-one (Compound 40), 378 mg (3.00 mmol) of 3-ethyl-3-methoxy-1-pentine, 14 mg (0.020 mmol) of PdCl$_2$(PPh$_3$)$_2$, 9.5 mg (0.050 mmol) of copper iodide (I), 15.7 mg (0.060 mmol) of triphenylphosphine and 0.5 ml of triethylamine were added to 4.0 ml of acetonitrile, and the mixture was heated under reflux for 5 hours in nitrogen atmosphere. After cooling to room temperature, t-butyl methyl ether was added to the reaction solution, and the mixture was washed with water and dried over anhydrous magnesium sulfate, then, concentrated under reduced pressure. The residue was subjected to silica gel column chromatography (eluant: hexane/ethyl acetate=2/1 (v/v)), to obtain 319 mg of 5-difluoromethyl-4-{5-(3-ethyl-3-methoxy-1-pentynyl)-2-methylbenzyl}-2-methyl-2,4-dihydro-3H-1,2,4-triazol-3-one (Compound 277).

$^1$H-NMR (CDCl$_3$, TMS) δ (ppm): 7.28(1H, d), 7.12 (1H, d), 7.02 (1H, s), 6.34 (1H, t), 4.95 (2H, s), 3.56 (3H, s), 3.36 (3H, s), 2.36 (3H, s), 1.75 (4H, q), 0.97 (6H, t)

Production Example 15

332 mg (1.00 mmol) of 4-(5-bromo-2-methylbenzyl)-5-difluoromethyl-2-methyl-2,4-dihydro-3H-1,2,4-triazol-3-one (Compound 40), 332 mg (1.0 mmol) of 3,3-dimethyl-1-butine, 14 mg (0.020 mmol) of PdCl$_2$(PPh$_3$)$_2$, 9.5 mg (0.050 mmol) of copper iodide (I), 15.7 mg (0.060 mmol) of triphenylphosphine and 0.5 ml of triethylamine were added to 4.0 ml of acetonitrile, and the mixture was heated at 40° C. for 8 hours in nitrogen atmosphere. After cooling to room temperature, t-butyl methyl ether was added to the reaction solution, and the mixture was washed with water and dried over anhydrous magnesium sulfate, then, concentrated under reduced pressure. The residue was subjected to silica gel column chromatography (eluant:hexane/ethylacetate=2/1 (v/v)), then to silica gel thin layer chromatography (4 times with hexane:ethyl acetate=2:1) to obtain 40 mg (0.13 mmol) of 5-difluoromethyl-4-{5-(3,3-dimethyl-1-butynyl)-2-methylbenzyl}-2-methyl-2,4-dihydro-3H-1,2,4-triazol-3-one (Compound 294).

$^1$H-NMR (CDCl$_3$, TMS) δ (ppm): 7.22 (1H, d), 7.08 (1H, d), 6.97 (1H, s), 6.31 (1H, t), 4.93 (2H, s), 3.56 (3H, s), 2.33 (3H, s), 1.29 (9H, s)

Production Example 16

664 mg (2.0 mmol) of 4-(5-bromo-2-methylbenzyl)-5-difluoromethyl-2-methyl-2,4-dihydro-3H-1,2,4-triazol-3- one (Compound 40), 1.00 g (11.9 mmol) of 2-methyl-3-butyn-2-ol, 70.2 mg (0.10 mmol) of $PdCl_2(PPh_3)_2$, 57.1 mg (0.30 mmol) of copper iodide, 78.7 mg (0.30 mmol) of triphenylphosphine, 1.0 ml of triethylamine and 10 ml of acetonitrile were mixed, and the mixture was heated under reflux for 5 hours in nitrogen atmosphere. After cooling to room temperature, t-butyl methyl ether was added to the reaction solution, and the mixture was filtered through celite, then, concentrated under reduced pressure. The residue was subjected to silica gel column chromatography (eluant: hexane/ethyl acetate=2/1 (v/v)) to obtain 400 mg of 5-difluoromethyl-4-{5-(3-hydroxyl-3-methyl-1-butynyl)-2-methylbenzyl}-2-methyl-2,4-dihydro-3H-1,2,4-triazol-3-one (Compound 290).

Production Example 17

3.0 ml of pyridine was added to 400 mg (1.19 mmol) of 5-difluoromethyl-4-{5-(3-hydroxyl-3-methyl-1-butynyl)-2-methylbenzyl}-2-methyl-2,4-dihydro-3H-1,2,4-triazol-3-one (Compound 290), then, 286 mg (2.8 mmol) of acetic anhydride and 12.2 mg (0.10 mmol) of N,N-dimethylaniline were further added. The mixed solution was heated for 7 hours at a bath temperature of 80° C. This mixture was cooled to room temperature, then, poured into a dilute hydrochloric acid-ice mixture. The resulted mixture was extracted twice with ethyl acetate, the organic layer was washed with water, then, with saturated saline, dried over anhydrous magnesium sulfate, then, concentrated under reduced pressure. Hexane was added to the residue and the mixture was stirred, then, filtrated to obtain 295 mg (0.78 mmol) of 4-{5-(3-acetoxy-3-methyl-1-butynyl)-2-methylbenzyl}-5-difluoromethyl-2-methyl-2,4-dihydro-3H-1,2,4-triazol-3-one (Compound 306).

$^1$H-NMR (CDCl$_3$, TMS) δ (ppm): 7.27 (1H, d), 7.12 (1H, d), 7.03 (1H, s), 6.32 (1H, t), 4.94 (2H, s), 3.57 (3H, s), 2.36 (3H, s), 2.07 (3H, s), 1.53)

Production Example 18

498 mg (1.5 mmol) of 4-(5-bromo-2-methylbenzyl)-5-difluoromethyl-2-methyl-2,4-dihydro-3H-1,2,4-triazol-3-one (Compound 40), 378 mg (1.2 mmol) of 3-methyl-3-methoxy-1-butine, 21.1 mg (0.030 mmol) of $PdCl_2(PPh_3)_2$, 19.0 mg (0.050 mmol) of copper iodide, 39.3 mg (0.15 mmol) of triphenylphosphine, 607 mg of triethylamine and 6.0 ml of acetonitrile were mixed, and the mixture was heated under reflux for 4.5 hours in nitrogen atmosphere. After cooling to room temperature, t-butyl methyl ether was added to the reaction solution, and the mixture was filtrated through celite, then, concentrated under reduced pressure. The residue was subjected to silica gel column chromatography (eluant: hexane/ethyl acetate=2/1 (v/v)) to obtain 360 mg of 5-difluoromethyl-2-methyl-4-{2-methyl-5-(3-methyl-methoxy-1-butynyl)-benzyl}-2,4-dihydro-3H-1,2,4-triazol-3-one (Compound 326).

$^1$H-NMR (CDCl$_3$, TMS) δ (ppm): 7.27 (1H, d), 7.12 (1H, d), 7.01 (1H, s), 6.33 (1H, t), 4.95 (2H, s), 3.40 (3H, s), 2.36 (3H, s), 1.52 (6H, s)

Production Example 19

150 mg (0.396 mmol) of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one (produced in the same manner as in Reference Production Example 3), 89 mg (0.517 mmol) of 2-bromo-6-methylpyridine, 420 mg (1.98 mmol) of tripotassium phosphate hydrate, 16 mg (0.020 mmol) of {1,1'-bis(diphenylphosphino)ferrocene}dichloropalladium (II) methylene chloride complex and 2.0 ml of ethylene glycol dimethyl ether were mixed, then stirred at 80° C. for 3 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 115 mg of 5-difluoromethyl-2-methyl-4-{2-methyl-5-(6-methyl-2-pyridyl)benzyl}-2,4-dihydro-3H-1,2,4-triazol-3-one (Compound 117).

$^1$H-NMR (CDCl$_3$, TMS) δ (ppm): 7.84 (1H, d), 7.57–7.34 (2H, m), 7.41 (1H, d), 7.26–7.29 (1H, m), 7.06 (1H, d), 6.30 (1H, t), 5.05 (2H, s), 3.55 (3H, s), 2.59 (3H, s), 2.50 (3H. s)

Production Example 20

150 mg (0.396 mmol) of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one (produced in the same manner as in Reference Production Example 3), 88 mg (0.595 mmol) of 2,6-dichloropyridine, 420 mg (1.98 mmol) of tripotassium phosphate hydrate, 16 mg (0.020 mmol) of {1,1'-bis(diphenylphosphino)ferrocene}dichloropalladium (II) methylene chloride complex and 2.0 ml of ethylene glycol dimethyl ether were mixed, then stirred at 80° C. for 3 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 103 mg of 4-{5-(6-chloro-2-pyridyl)-2-methylbenzyl}-5-difluoromethyl-2-methyl-2,4-dihydro-3H-1,2,4-triazol-3-one (Compound 118).

$^1$H-NMR (CDCl$_3$, TMS) δ (ppm): 7.89 (1H, dd), 7.64–7.70(2H, m), 7.54 (1H, dd), 7.21–7.31 (2H, m), 6.33 (1H, t), 5.05 (2H, s), 3.56 (3H, t), 2.42 (3H, s)

Production Example 21

150 mg (0.396 mmol) of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one (produced in the same manner as in Reference Production Example 3), 94 mg (0.515 mmol) of 2-chloro-4-trifluoromethylpyrimidine, 420 mg (1.98 mmol) of tripotassium phosphate hydrate, 16 mg (0.020 mmol) of {1,1'-bis(diphenylphosphino)ferrocene}-dichloropalladium (II) methylene chloride complex and 2.0 ml of ethylene glycol dimethyl ether were mixed, then stirred at 80° C. for 3 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 132 mg of 5-difluoromethyl-2-methyl-4-{2-methyl-5-(4-trifluoromethyl-2-pyrimidinyl)benzyl}-2,4-dihydro-3H-1,2,4-triazol-3-one (Compound 345).

$^1$H-NMR (CDCl$_3$, TMS) δ (ppm): 8.99 (1H, d), 8.36 (1H, dd), 8.14 (1H, s), 7.46 (1H, d), 7.34 (1H, d), 6.35 (1H, t), 5.07 (2H, s), 3.57 (3H, s), 2.25 (3H, s)

Production Example 22

150 mg (0.396 mmol) of 5-difluoromethyl-2-methyl-4-{2-methyl-5-(4,4,5,5-tetramethyl-1,3,2-dioxobororan-2-yl)

benzyl}-2,4-dihydro-3H-1,2,4-triazol-3-one (produced in the same manner as in Reference Production Example 3), 116 mg (0.516 mmol) of 3-bromo-benzotrifluoride, 420 mg (1.98 mmol) of tripotassium phosphate hydrate, 16 mg (0.020 mmol) of {1,1'-bis(diphenylphosphino) ferrocene}dichloropalladium (II) methylene chloride complex and 2.0 ml of ethylene glycol dimethyl ether were mixed, then stirred at 80° C. for 3 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 126 mg of 5-difluoromethyl-2-methyl-4-{2-methyl-5-(3-trifluoromethylphenyl)benzyl}-2,4-dihydro-3H-1,2,4-triazol-3-one (Compound 24).

$^1$H-NMR (CDCl$_3$, TMS) δ (ppm): 7.73 (1H, s), 7.65–7.67 (1H, m), 7.49–7.59 (2H, m), 7.43 (1H, dd), 7.27–7.30 (1H, m), 7.19 (1H, s), 6.36 (1H, t), 5.05 (2H, s), 3.55 (3H, s), 2.42 (3H, s)

Production Example 23

150 mg (0.396 mmol) of 5-difluoromethyl-2-methyl-4-{2-methyl-5-(4,4,5,5-tetramethyl-1,3,2-dioxobororan-2-yl)benzyl}-2,4-dihydro-3H-1,2, 4-triazol-3-one (produced in the same manner as in Reference Production Example 3), 114 mg (0.595 mmol) of 3-bromochlorobenzene, 420 mg (1.98 mmol) of tripotassium phosphate hydrate, 16 mg (0.020 mmol) of {1,1'-bis(diphenylphosphino) ferrocene}dichloropalladium (II) methylene chloride complex and 2.0 ml of ethylene glycol dimethyl ether were mixed, then stirred at 80° C. for 3 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography (eluant: hexane/ethyl acetate=1/1 (v/v, addition of 1 vol % methanol)}, to obtain 118 mg of 4-{5-(3-chlorophenyl)-2-methylbenzyl}-5-difluoromethyl-2-methyl-2,4-dihydro-3H-1,2,4-triazol-3-one (Compound 6).

$^1$H-NMR (CDCl$_3$, TMS) δ (ppm): 7.47 (1H, s), 7.25–7.41 (5H, m), 7.15 (1H, s), 6.35 (1H, t), 5.04 (2H, s), 3.55 (3H, s), 2.41 (3H, s)

Production Example 24

150 mg (0.396 mmol) of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one (produced in the same manner as in Reference Production Example 3), 101 mg (0.591 mmol) of 3-bromo-toluene, 420 mg (1.98 mmol) of tripotassium phosphate hydrate, 16 mg (0.020 mmol) of {1,1'-bis(diphenylphosphino) ferrocene}dichloropalladium (II) methylene chloride complex and 2.0 ml of ethylene glycol dimethyl ether were mixed, then stirred at 80° C. for 3 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 106 mg of 5-difluoromethyl-2-methyl-4-{2-methyl-5-(3-methylphenyl)benzyl}-2,4-dihydro-3H-1,2,4-triazol-3-one (Compound 3).

$^1$H-NMR (CDCl$_3$, TMS) δ (ppm): 7.41 (1H, dd), 7.23–7.33 (4H, m), 7.13–7.18 (2H, m), 6.32 (1H, t), 5.04 (2H, s), 3.54 (3H, s), 2.40 (2H, s)

Production Example 25

150 mg (0.396 mmol) of 5-difluoromethyl-2-methyl-4-{2-methyl-5-(4,4,5,5-tetramethyl-1,3,2-dioxobororan-2-yl)benzyl}-2,4-dihydro-3H-1,2,4-triazol-3-one (produced in the same manner as in Reference Production Example 3), 114 mg (0.596 mmol) of 4-bromochlorobenzene, 420 mg (1.98 mmol) of tripotassium phosphate hydrate, 16 mg (0.020 mmol) of {1,1'-bis(diphenylphosphino) ferrocene}dichloropalladium (II) methylene chloride complex and 2.0 ml of ethylene glycol dimethyl ether were mixed, then stirred at 80° C. for 3 hours. The mixture was cooled, then, ethyl acetate was added to this and the mixture was filtrated through a glass filter precoated with celite. The solvent of the filtrate was distilled off under reduced pressure, and the residue was subjected to silica gel thin layer chromatography {eluant: hexane/ethyl acetate=1/1 (v/v, addition of 1 vol % methanol)}, to obtain 120 mg of 4-{5-(4-chlorophenyl)-2-methylbenzyl}-5-difluoromethyl-2-methyl-2,4-dihydro-3H-1,2,4-triazol-3-one (Compound 7).

$^1$H-NMR (CDCl$_3$, TMS) δ (ppm): 7.35–7.43 (5H, m), 7.24–7.27 (1H, m), 7.15 (1H, s), 6.35 (1H, t), 5.04 (2H, s), 3.54 (3H, s), 2.40 (1H, s)

Production Example 26

300 mg (1.11 mmol) of 2-methyl-4-(2-methyl-5-phenylbenzyl) semicarbazide (produced in the same manner as in Intermediate Production Example 4) was dissolved in 2 ml of methanol, and to this solution was added, in nitrogen atmosphre, 180 ml (1.45 mmol) of ethyl difluoroacetate and 0.23 ml (1.11 mmol) of a 28% sodium methoxide methanol solution. The mixture was stirred for 9 hours while heating under reflux, cooled to room temperature, then, 20 ml of water was added to the reaction solution, then, 2N hydrochloric acid was added to control pH to 1, and extracted with ethyl acetate. The organic layer was washed with a saturated sodium bicarbonate solution, then with saturated saline, and dried over anhydrous magnesium sulfate, then, concentrated. The residue was subjected to silica gel column chromatography (eluant: hexane/ethyl acetate=4/1, 2/1, then, 1/2 (v/v)) to obtain 279 mg of 5-difluoromethyl-2-methyl-4-(2-methyl-5-phenylbenzyl)-2,4-dihydro-3H-1,2, 4-triazol-3-one (Compound 1) and 88 mg of 1-difluoroacetyl-2-methyl-4-(2-methyl-5-phenylbenzyl) semicarbazide. 1-difluoroacetyl-2-methyl-4-(2-methyl-5-phenylbenzyl) semicarbazide:

$^1$H-NMR (CDCl$_3$, TMS) δ (ppm): 8.96 (1H, s), 7.60–7.12 (8H, m), 5.82 (1H, t), 5.45 (1H, t), 4.34 (2H, d), 3.04 (3H, s), 2.26 (3H, s)

Production Example 27

265 mg (0.984 mmol) of 2-methyl-4-(2-methyl-5-phenylbenzyl) semicarbazide (produced in the same manner as in Intermediate Production Example 4) was mixed with 0.5 ml (7.95 mmol) of difluoroacetic acid, and the mixture was stirred at 70° C. for 6.5 hours. The reaction solution was cooled to room temperature, then, 5 ml of water was added, and extracted with ethyl acetate. The organic layer was washed with a sodium bicarbonate solution, then, with saturated saline, and dried over anhydrous magnesium sulfate. The residue was subjected to silica gel column chromatography (eluant: hexane/ethyl acetate=1/1 (v/v), then ethyl acetate) to obtain 19 mg of 5-difluoromethyl-2-methyl-4-(2-methyl-5-phenylbenzyl)-2,4-dihydro-3H-1,2,4-triazol-3-one (Compound 1) and 297 mg of 1-difluoroacetyl-2-methyl-4-(2-methyl-5-phenylbenzyl) semicarbazide.

Production Example 28

146 mg (0.420 mmol) of 1-difluoroacetyl-2-methyl-4-(2-methyl-5-phenylbenzyl) semicarbazide (produced in the same manner as in Intermediate Production Example 27) was added to 2 ml of a 2 wt % potassium hydroxide aqueous solution, and the mixture was stirred while heating under reflux for 3 hours. The reaction solution was cooled to room temperature, then, pH was controlled to 3 by addition of 2 N hydrochloric acid, and extracted with ethyl acetate. The organic layer was washed with a sodium bicarbonate solution, then, with saturated saline, and dried over anhydrous magnesium sulfate, then, concentrated to obtain 133 mg of 5-difluoromethyl-2-methyl-4-(2-methyl-5-phenylbenzyl)-2,4-dihydro-3H-1,2,4-triazol-3-one (Compound 1).

Production Example 29

100 mg (0.371 mmol) of 2-methyl-4-(2-methyl-5-phenylbenzyl) semicarbazide (produced in the same manner as in Intermediate Production Example 4) and 53 mg (0.557 mmol) of difluoroacetic acid were added to 3.7 ml of toluene, the mixture was stirred at 100° C. for 3 hours, then, stirred for 5 hours under reflux with heating. The reaction solution was cooled to room temperature, then, washed with a saturated sodium bicarbonate solution, then with saturated saline, and dried over anhydrous magnesium sulfate, then, concentrated. The residue was subjected to silica gel thin layer chromatography (eluant: hexane/ethyl acetate=2/1 (v/v)) to obtain 98 mg of 5-difluoromethyl-2-methyl-4-(2-methyl-5-phenylbenzyl)-2,4-dihydro-3H-1,2,4-triazol-3-one (Compound 1) and 14 mg of N-(2-methyl-5-phenylbenzyl)-difluoroacetoamide. N-(2-methyl-5-phenylbenzyl)-difluoroacetoamide:

$^1$H-NMR (CDCl$_3$, TMS) δ (ppm): 7.19–7.60 (8H, m), 6.57 (1H, br), 5.91 (1H, t), 4.55 (2H, d), 2.35 (3H, s)

Production Example 30

91 mg (0.60 mmol) of 3-methoxyphenylboronic acid, 143 mg (0.43 mmol) of 4-(5-bromo-2-methylbenzyl)-5-difluoromethyl-2-methyl-2,4-dihydro-3H-1,2,4-triazol-3-one (Compound40; produced in the same manner as in Production Example 2), 0.54 g of tripotassium phosphate hydrate and 18 mg (0.022 mmol) of [1,1'-bis(diphenylphosphono)ferrocene]-dichloropalladium (II) methylene chloride complex were suspended in 8 ml of 1,2-dimethoxyethane, and stirred for 2 hours in nitrogen atmosphere under reflux with heating. Ethyl acetate was added to the reaction solution and the mixture was filtrated through celite, then, the filtrate was concentrated. The residue (0.19 g) was subjected to silica gel thin layer chromatography (eluant: toluene/ethyl acetate=4/1 (v/v)), to obtain 0.11 g of 5-difluoromethyl-4-{5-(3-methoxyphenyl)-2-methylbenzyl}-2-methyl-2,4-dihydro-3H-1,2,4-triazol-3-one (Compound 9) in the form of oil.
$^1$H-NMR (CDCl$_3$, TMS) δ (ppm): 6.85–7.45 (7H, m), 6.33 (1H, t), 5.03 (2H, s), 3.84 (3H, s), 3.53 (3H, s), 2.40 (3H, s)

Production Example 31

100 mg (0.671 mmol) of 5-difluoromethyl-2-methyl-2,4-dihydro-3H-1,2,4-triazol-3-one (produced in the same manner as in Intermediate Production Example 1) and 175 mg (0.671 mmol) of 2-methyl-5-phenylbenzyl bromide (produced in the same manner as in Reference Production Example 1 (5) ) were dissolved in 2 ml of N,N-dimethylformamide and the solution was cooled to 0° C., and to this was added 40 mg of sodium hydride (1.00 mmol, 60% in oil) slowly. The resulted suspension was allowed to cool to room temperature, and stirred for 2 hours. The reaction solution was cooled to 0° C., and water was added slowly, the mixture was extracted with ethyl acetate. The organic layer was washed with water, saturated sodium bicarbonate solution and saturated saline sequentially, dried over anhydrous magnesium sulfate, then, concentrated. The residue was subjected to silica gel thin layer chromatography (eluant: hexane/ethyl acetate=2/1 (v/v)), to obtain 98 mg of 5-difluoromethyl-2-methyl-4-(2-methyl-5-phenylbenzyl)-2,4-dihydro-3H-1,2,4-triazol-3-one (Compound 1) and 77 mg of 3-difluoromethyl-5-(2-methyl-5-phenylbenzyl)-1-methyl-1H-1,2,4-triazole as a by-product. 3-difluoromethyl-5-(2-methyl-5-phenylbenzyl.)-1-methyl-1H-1,2,4-triazole:

$^1$H-NMR (CDCl$_3$, TMS) δ (ppm): 7.28–7.70 (8H, m), 6.54 (1H, t), 5.55 (2H, s), 3.65 (3H, s), 2.45 (3H, s)

Production Example 32

5-difluoromethyl-2-methyl-2,4-dihydro-3H-1,2,4-triazol-3-one (produced in the same manner as in Intermediate Production Example 1) and 2-methyl-5-phenylbenzyl chloride (produced in the same manner as in Intermediate Production Example 9) are dissolved in N,N-dimethylformamide and the solution is cooled to 0° C., and to this is added sodium hydride slowly. The resulting suspension is allowed to cool to room temperature, and stirred. The reaction solution is cooled to 0° C., and water is added slowly, the mixture is extracted with ethyl acetate. The organic layer is washed with water, saturated sodium bicarbonate solution and saturated saline sequentially, dried over anhydrous magnesium sulfate, and then, concentrated. The residue is subjected to silica gel thin layer chromatography to obtain 5-difluoromethyl-2-methyl-4-(2-methyl-5-phenylbenzyl)-2,4-dihydro-3H-1,2,4-triazol-3-one (Compound 1).

Production Example 33

A mixed suspension of 203 mg (1.36 mmol) of 5-difluoromethyl-2-methyl-2,4-dihydro-3H-1,2,4-triazol-3-one (produced in the same manner as in Intermediate Production Example 1), 35 mg (1.46 mmol) of lithium hydroxide and 5 ml of toluene was stirred for 2 hours while heating under reflux. Toluene was distilled off under reduced pressure, 3 ml of anhydrous 1,4-dioxane was added to the residue under nitrogen atmosphere, then, 368 mg (1.33 mmol) of 2-methyl-5-phenylbenzyl methanesulfonate (produced in the same manner as in Intermediate Production Example 11) was added. The reaction solution was stirred for 2 hours while heating under reflux, then, concentrated. Ethyl acetate was added to the residue, the mixture was washed with water, washed with saturated saline, and dried over anhydrous magnesium sulfate, then, concentrated. The residue was subjected to silica gel thin layer chromatography (eluant: hexane/ethyl acetate=4/1, then 2/1 (v/v)), to obtain 385 mg of 5-difluoromethyl-2-methyl-4-(2-methyl-5-phenylbenzyl)-2,4-dihydro-3H-1,2,4-triazol-3-one (Compound 1) and 31 mg of 3-difluoromethyl-1-methyl-5-(2-methyl-5-phenylbenzyloxy)-1H-1,2,4-triazole as a by-product.

Production Example 34

A mixed suspension of 69 mg (0.461 mmol) of 5-difluoromethyl-2-methyl-2,4-dihydro-3H-1,2,4-triazol-3- one (produced in the same manner as in Intermediate Production Example), 12 mg (0.508 mmol) of lithium hydroxide, 14 mg (0.092 mmol) of sodium iodide and 3 ml of toluene was stirred for 2 hours while heating under reflux. Toluene was distilled off under reduced pressure, 3 ml of anhydrous 1,4-dioxane was added to the residue under nitrogen atmosphere, then, 100 mg (0.461 mmol) of 2-methyl-5-phenylbenzyl chloride was added. The reaction solution was stirred for 18 hours while heating under reflux, then, concentrated. Ethyl acetate was added to the residue, the mixture was washed with water, then, washed with saturated saline, and dried over anhydrous magnesium sulfate, then, concentrated. The residue was subjected to silica gel thin layer chromatography (eluant: hexane/ethyl acetate=3/1 (v/v)), to obtain 61 mg of 5-difluoromethyl-2-methyl-4-(2-methyl-5-phenylbenzyl)-2,4-dihydro-3H-1,2,4-triazol-3-one (Compound 1) and 11 mg of 3-difluoromethyl-1-methyl-5-(2-methyl-5-phenylbenzyloxy)-1H-1,2,4-triazole as a by-product.

Production Example 35

944 mg (3.35 mmol) of 2-chloro-5-phenylbenzyl bromide (produced in the same manner as in Reference Production Example 5) was dissolved in 10 ml of 1,4-dioxane, and cooled to 0° C. To this solution was added 500 mg (3.35 mmol) of 5-difluoromethyl-2-methyl-2,4-dihydro-3H-1,2,4-triazol-3-o ne (produced in the same manner as in Intermediate Production Example 1) and 40 mg (5.03 mmol) of lithium hydroxide. The mixture was stirred for 30 hours under reflux with heating, then allowed to cool to room temperature. To this mixture was added 6 ml of anhydrous N,N-dimethylformamide, and 180 mg (1.21 mmol) of 5-difluoromethyl-2-methyl-2,4-dihydro-3H-1,2,4-triazol-3-one and 200 mg (5.00 mmol, 60%, in oil) of sodium hydride were added, and the mixture was stirred at room temperature for 1 hour, then, a saturated ammonium chloride aqueous solution was added, and extracted with ethyl acetate. The organic layer was washed with a saturated sodium hydrogen carbonate aqueous solution and saturated saline sequentially, dried over anhydrous magnesium sulfate, then, concentrated. The residue was subjected to silica gel column chromatography (eluant: hexane/ethyl acetate=4/1, then, 2/1 (v/v)) to obtain 824 mg of 5-difluoromethyl-2-methyl-4-(2-chloro-5-phenylbenzyl)-2,4-dihydro-3H-1,2,4-triazol-3-one (Compound 377).

$^1$H-NMR (CDCl$_3$, TMS) δ (ppm): 7.17–7.51 (8H, m), 6.42 (1H, t), 5.18 (2H, s), 3.54 (3H, s)

Reference Production Example 5

(1) A mixture of 5.00 g (24.3 mmol) of 5-bromo-2-chlorotoluene, 3.56 g (29.2 mmol) of dihydroxyphenylborane, 546 mg (2.43 mmol) of palladium acetate (II), 9.41 g (29.2 mmol) of tetrabutylammonium bromide, 8.40 g (60.8 mmol) of potassium carbonate and 50 ml of water was stirred for 5 hours at 80° C. under nitrogen flow. The reaction solution was filtrated through celite, and the filtrate was extracted with ethyl acetate. The organic layer was washed with saturated saline, dried over anhydrous magnesium sulfate, then, concentrated. The residue was subjected to silica gel column chromatography (eluant: hexane) to obtain 3.92 g of 4-chloro-3-methylbiphenyl.

$^1$H-NMR (CDCl$_3$, TMS) δ (ppm): 7.30–7.60 (8H, m), 2.44 (3H, s)

(2) 3.90 g (19.2 mmol) of 4-chloro-3-methylbiphenyl was dissolved in 100 ml of carbon tetrachloride and to this solution was added 632 mg (3.85 mmol) of 2,2'-azobisisobutylonitrile, and the mixture was stirred at room temperature for 15 minutes. To this solution was added 3.43 g (19.2 mmol) of N-bromosuccinimide, and the mixture was stirred for 3.5 hours while heating under reflux. To the reaction solution was further added 632 mg (3.85 mmol) of 2,2'-azobisisobutyronitrile and 300 mg (1.69 mmol) of N-bromosuccinimide, and the mixture was stirred for 2 hours under reflux with heating. The reaction mixture was filtrated, and the filtrate was concentrated. The residue was subjected to silica gel column chromatography (eluant: hexane) to obtain 4.69 g of 2-chloro-5-phenylbenzyl bromide in the form of colorless transparent oil.

$^1$H-NMR (CDCl$_3$, TMS) δ (ppm): 7.31–7.69 (8H, m), 4.64 (2H, s)

Next, examples of producing intermediates of the invention are described.

First, the production example of 5-difluoromethyl-2-methyl-2,4-dihydro-3H-1,2,4-triazol-3-one of the formula [L] is shown below.

Intermediate Production Example 1

20 ml of toluene was added to 500 mg (5.61 mmol) of 2-methyl semicarbazide (produced in the same manner as in Reference Production Example 6), and to this mixture was added 808 mg (8.41 mmol) of difluoroacetic acid, and the mixture was stirred for 10 hours under reflux with heating. The reaction solution was cooled to room temperature, then, concentrated, and the residue was subjected to silica gel thin layer chromatography (eluant: chloroform/methanol=9/1 (v/v)), to obtain 305 mg of 5-difluoromethyl-2-methyl-2,4-dihydro-3H-1,2,4-triazol-3-one having a melting point of 141.2° C. in the form of colorless solid.

$^1$H-NMR (CDCl$_3$, TMS) δ (ppm): 12.2 (1H, br), 6.46 (1H, t), 3.52 (3H, s)

Next, the production example of difluoroacetyl semicarbazide of the formula [XXVI] is shown below.

Intermediate Production Example 2

1.00 g of crude 2-methyl-5-phenylbenzyl isocyanate is added to 5 ml of toluene, and to the resulted suspension is added 556 mg of N'-methyl-difluoroacetohydrazide, and the mixture is stirred at 60° C. The reaction solution is concentrated, and the residue is subjected to silica gel column chromatography, to obtain 1-difluoroacetyl-2-methyl-4-(2-methyl-5-phenylbenzyl) semicarbazide.

Next, the production example of a semicarbazide compound of the formula [VII] is shown below.

Intermediate Production Example 3

(1) 2.5 g (12.6 mmol) of diphosgene, 0.40 g of activated carbon and 30 ml of toluene were mixed, and allowed to left overnight, and to this solution was slowly dropped at room temperature a solution prepared by dissolving 1.00 g (5.07 mmol) of 2-methyl-5-phenylbenzylamine (produced in the same manner as in Intermediate Production Example 6) in 5 ml of toluene. The reaction mixture turned to white suspension directly after the dropping. The white suspension was stirred at room temperature for 1 hour, further stirred for 5 hours under reflux with heating, then, concentrated under reduced pressure to obtain 1.13 g of 2-methyl-5-phenybenzyl isocyanate.

$^1$H-NMR (CDCl$_3$, TMS) δ (ppm): 7.22–7.65 (8H, m), 4.54 (2H, s), 2.38 (3H, s)

(2) 254 mg (5.52 mmol) of methylhydrazine was dissolved in 10 ml of anhydrous toluene, and the mixture was cooled to 0° C. Tot this solution was slowly dropped while stirring a solution prepared by dissolving 1.12 g (5.02 mmol) of 2-methyl-5-phenylbenzyl isocyanate in 20 ml of anhydrous toluene. In this operation, the temperature of the reaction solution was controlled in the range from 0 to 5° C. After completion of dropping, the solution was stirred at 0° C. for 1 hour, further, stirring was continued for 2 hours at room temperature. The reaction solution was concentrated, and the residue was subjected to silica gel column chromatography (eluant: hexane/ethyl acetate=1/1, then, 1/2 (v/v), then only ethyl acetate), to obtain 1.28 g (4.75 mmol) of 2-methyl-4-(2-methyl-5-phenylbenzyl) semicarbazide having a melting point of 91.6° C.

$^1$H-NMR (CDCl$_3$, TMS) δ (ppm): 7.18–7.64 (8H, m), 6.68 (1H, br), 4.45 (2H, d), 3.56 (2H, s), 3.16 (3H, s), 2.38 (3H, s)

Intermediate Production Example 4

3.0 g (11.6 mmol) of 2-methyl-5-phenylbenzyl bromide (produced in the same manner as in Reference Production Example 1 (5)) was dissolved in 5 ml of anhydrous N,N-dimethylformamide, and to this solution was added 1.13 g (17.3 mmol) of sodium cyanide, and the mixture was stirred for 3 hours at 100° C., to obtain a 2-methyl-5-phenylbenzyl isocyanate solution. To this solution was added 5 ml of toluene, then, the solution was cooled to 0° C., and to this was slowly dropped 550 mg (11.9 mmol) of methylhydrazine. Further, the mixture was stirred for 3 hours at room temperature, and to this reaction mixture was added water, and the mixture was extracted with chloroform. The organic layer was washed with saturated saline, then, dried over anhydrous magnesium sulfate, and concentrated. The residue was subjected to silica gel column chromatography (eluant: ethyl acetate/methanol=9/1 (v/v)), to obtain 1.24 g of 2-methyl-4-(2-methyl-5-phenylbenzyl) semicarbazide.

Intermediate Production Example 5

1.0 g (4.61 mmol) of 2-methyl-5-phenylbenzyl chloride (produced in the same manner as in Intermediate Production Example 10) is dissolved in 2 ml of anhydrous N,N-dimethylformamide, and to this solution is added 450 mg (6.92 mmol) of sodium cyanide, and the mixture is stirred at 100° C. Subsequently, 2 ml of toluene is added to the reaction solution and the mixture is cooled to 0° C., to this is added 213 mg (4.61 mmol) of methylhydrazine, the mixture is stirred at room temperature, then, to this is added water, and the mixture is extracted with chloroform. The organic layer is washed with saturated saline, end-dried over anhydrous magnesium sulfate, and concentrated to obtain 2-methyl-4-(2-methyl-5-phenylbenzyl) semicarbazide.

Next, the production example of 2-methyl-5-phenylbenzylamine of the formula [XVI-1] is shown below.

Intermediate Production Example 6

1.0 g (5.17 mmol) of 2-methyl-5-phenylbenzonitrile (produced in the same manner as in the above-mentioned Reference Production Example 1 (2)) was dissolved in a mixed solvent of 8 ml of 1,4-dioxane and 8 ml of ethanol, and to this solution was added 1.0 g of a suspension of 2 ml of 28 wt % ammonia water and Raney nickel W2 (manufactured by Aldrich; 50 wt % in water). This mixture was stirred for 8 hours at room temperature under hydrogen atmosphere, then, filtrated through celite, and the celite was washed with ethanol and water. The filtrate and washed solution was combined and concentrated under reduced pressure, and the residue was distilled by using Kugelrohl distillation apparatus (0.5 mmHg, set temperature: 216° C.), to obtain 842 mg (4.27 mmol) of 2-methyl-5-phenylbenzylamine.

$^1$H-NMR (CDCl$_3$, TMS) δ (ppm): 7.20–7.66 (8H, m), 3.92 (2H, s), 2.38 (3H, s), 1.47 (2H, brs)

Intermediate Production Example 7

4.46 g (23.1 mmol) of 2-methyl-5-phenylbenzonitrile was dissolved in 26 ml of 1,4-dioxane and to this was added 5 ml of ethanol. To this solution was added 9 ml of 28 wt % ammonia water, and 3 g of a suspension of Raney nickel W2 (manufactured by Aldrich; 50 wt % in water). This mixture was stirred for 8 hours at room temperature under hydrogen atmosphere. To this mixture was further added 2 g of a suspension of Raney nickel W2 (manufactured by Aldrich; 50 wt % in water), 8 ml of 28 wt % ammonia water and 20 ml of ethanol, and the mixture was stirred for 4.5 hours at room temperature under hydrogen atmosphere. The reaction mixed was filtrated through celite, and the filtrate was concentrated. The residue was distilled by using Kugelrohl distillation apparatus (0.5 mmHg, set temperature: 216° C.), to obtain 4.25 g of 2-methyl-5-phenylbenzylamine.

Intermediate Production Example 8

100 mg (0.461 mmol) of 2-methyl-5-phenylbenzyl chloride (produced in the same manner as in Intermediate Production Example 9) was dissolved in 100 ml of chloroform, and to this solution was added 65 mg (0.461 mmol) of hexamethyltetramine, and the mixture was stirred for 15 hours under reflux with heating, then, 32 mg (0.228 mmol) of hexamethyltetramine was further added, and stirring was continued for 10 hours under reflux with heating. The resulted crystal was filtrated, and the crystal was washed with t-butyl methyl ether. The resulted crystal was dissolved in a mixture of 2 ml of ethanol and 0.5 ml of water, and to this solution was 0.2 ml of concentrated hydrochloric acid, and the mixture was stirred at room temperature overnight, then, concentrated. To the residue was added a 2N sodium hydroxide aqueous solution, and the mixture was extracted with t-butyl methyl ether. The organic layer was washed with saturated saline, dried over anhydrous magnesium sulfate, then, the mixture was concentrated to obtain 97 mg of crude 2-methyl-5-phenylbenzylamine.

Next, the production example of 2-methyl-5-phenylbenzyl chloride of the formula [XIII-1] is shown below.

Intermediate Production Example 9

500 mg (2.52 mmol) of 2-methyl-5-phenylbenzyl alcohol (produced in the same manner as in Reference Production Example 1 (4)) was dissolved in 2 ml of carbon tetrachloride, and to this solution was added 1.0 g (3.28 mmol) of triphenylphosphine under nitrogen atmosphere. The reaction mixture was stirred for 1.5 hours under reflux with heating, cooled to room temperature, then, concentrated. The residue was subjected to silica gel column chromatography (eluant: hexane/ethyl acetate=10/1 (v/v)), to obtain 508 mg of 2-methyl-5-phenylbenzyl chloride.

¹H-NMR (CDCl₃, TMS) δ (ppm): 7.19–7.63 (8H, m), 4.67 (2H, s), 2.46 (3H, s)

Intermediate Production Example 10

315 mg (1.40 mmol) of N,N-dimethyl-(2-methyl-5-phenylbenzyl)amine (produced in the same manner as in Intermediate Production Example 12) was dissolved in 3 ml of toluene, and to this solution was added 370 mg (3.92 mmol) of methyl chlorocarbonate at room temperature. Directly after addition, the reaction mixture tuned to white suspension. This while suspension was stirred at room temperature for 7 hours, then, washed with 1 N hydrochloric acid, saturated sodium bicarbonate water, and saturated saline, sequentially, and dried over anhydrous magnesium sulfate, then, concentrated. The residue was subjected to silica gel column chromatography (eluant: hexane, then, hexane/ethyl acetate=10/1 (v/v)), to obtain 282 mg of 2-methyl-5-phenylbenzyl chloride.

The production method of a compound of the formula [XIII-2] in which $R^9$ is a methyl is described below.

Intermediate Production Example 11

2.00 g (10.1 mmol) of 2-methyl-5-phenylbenzyl alcohol was dissolved in 100 ml of ethyl acetate, and to this solution was added 4.2 ml (30.3 mmol) of triethylamine and the mixture was cooled to 0° C. To the reaction mixture was slowly dropped 1.73 g (15.1 mmol) of methanesulfonyl chloride, and the reaction mixture was controlled to room temperature. After stirring for 1 hours at room temperature, the reaction mixture was made acidic by addition of 1 N hydrochloric acid, and the mixture was extracted with ethyl acetate. The organic layer was washed with a saturated sodium bicarbonate solution and saturated saline sequentially, dried over anhydrous magnesium sulfate, then, concentrated. The residue was subjected to silica gel column chromatography (eluant: hexane/ethyl acetate=4/1 (v/v)), to obtain 2.79 g of 2-methyl-5-phenylbenzyl methanesulfonate.

¹H-NMR (CDCl₃, TMS) δ (ppm): 7.25–7.68 (8H, m), 5.34 (2H, s), 2.93 (3H, s), 2.45 (3H, s)

Next, the production example of N-dimethyl-(2-methyl-5-phenylbenzyl)amine is shown below.

Intermediate Production Example 12

(1) A mixture of 3.0 g (14.8 mmol) of 4-phenylbenzyl chloride, 10 ml of toluene and 5.6 ml (26.6 mmol) of a 30 wt % trimethylamine aqueous solution was stirred for 3.7 hours at 60° C. The reaction solution was separated, and the resulted aqueous layer was washed with t-butyl methyl ether. The aqueous layer was filtrated through celite, and the filtrate was concentrated to obtain 4.07 g of (4-methylbenzyl)-trimethylammonium chloride having a melting point of 204.8° C.

¹H-NMR (DMSO-d₆, TMS) 67 (ppm): 7.35–7.87 (9H, m), 4.72 (2H, s), 3.11 (9H, s)

(2) 500 mg (1.91 mmol) of (4-phenylbenzyl)-trimethylammonium chloride was dissolved in 20 ml of anhydrous dimethyl sulfoxide, and to the resulted solution was added 153 mg (3.82 mmol, 60% in oil) of sodium hydride at room temperature under nitrogen atmosphere, and the mixture was stirred for 8 hours. To the reaction solution was added 180 ml of saturated saline, and extracted twice with each 70 ml of t-butyl methyl ether. The organic layer was washed with saturated saline, then, dried over anhydrous magnesium sulfate, and concentrated to obtain 452 mg of N,N-dimethyl-(2-methyl-5-phenylbenzyl)amine.

¹H-NMR (CDCl₃, TMS) δ (ppm): 7.20–7.66 (8H, m), 3.43 (2H, s), 2.40 (3H, s), 2.27 (6H, s)

Next, the production example of producing a benzyl alcohol compound of the formula [XIII-2] from a benzyl chloride compound of the formula [XVII] is shown below.

Reference Production Example 4

264 mg of magnesium and 0.5 ml of anhydrous diethyl ether were charged into a 4-necked round bottomed flask filled with nitrogen, then, small pieces of iodine were placed. After left for a while, the color of iodine disappeared, then, to this was dropped slowly a solution prepared by dissolving 2.0 g (9.87 mmol) of 4-phenylbenzyl chloride in 15 ml of anhydrous diethyl ether. After completion of dropping, the mixture was stirred until most of magnesium was dissolved. Into the resulted brown solution, formaldehyde obtained by thermal decomposition at 200° C. of 1.48 g (49.4 mmol) of para-formaldehyde sufficiently dried was blown over 1 hour at gas layer part of the reaction vessel together with nitrogen flow. After completion of blowing, stirring was further continued for 2 hours at room temperature, and a saturated ammonium chloride aqueous solution was added. The resulted solution was extracted with t-butyl methyl ether, washed with saturated saline, and concentrated. The residue was subjected to silica gel column chromatography (eluant: hexane/ethyl acetate=10/1, then 4:1 (v/v)), to obtain 787 mg of 2-methyl-5-phenylbenzyl alcohol.

¹H-NMR (CDCl₃, TMS) δ (ppm): 7.21–7.63 (8H, m), 4.77 (2H, d), 2.40 (3H, s), 1.56 (1H, dd)

Next, the production example of producing 2-methyl semicarbazide from methylhydrazine is shown below.

Reference Production Example 6

6.0 g (130 mmol) of methylhydrazine was dissolved in 25 ml of tetrahydrofuran and cooled to 0° C., to the resulted solution was slowly dropped 11.5 g (100 mmol) of trimethylsilyl isocyanate. After completion of dropping, the mixture was stirred for further 1 hour. Then, 20 ml of methanol was added to the reaction solution, the mixture was stirred for 5 hours at 40° C., and concentrated to obtain 7.77 g of 2-methyl semicarbazide in the form of pale yellow solid.

¹H-NMR (CDCl₃, TMS) δ (ppm): 5.61 (2H, br), 3.80 (2H, brs), 3.15 (3H, s)

Reference Production Example 7

1.3 g (200 mmol) of sodium cyanate, 9.67 g (210 mmol) of methylhydrazine and 100 ml of water were mixed, and the mixture was cooled to 0° C. To the resulted suspension, 18.3 ml (210 mmol) of concentrated hydrochloric acid was dropped over 20 minutes, the reaction mixture was controlled to room temperature, then, stirred for 3 hours. Then, the reaction mixture was filtrated, and the filtrate was concentrated to obtain 10.8 g of crude 2-methyl semicarbazide.

Next, examples of the compounds of the invention are shown with Compound Number.

The compound of the invention of the formula [I-a] (Table 1 to 15)

TABLE 1

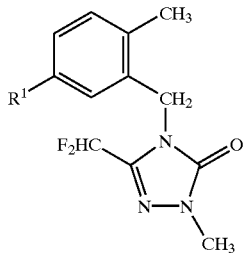

[I-a]

| Compound Number | R¹ |
|---|---|
| 1 | phenyl |
| 2 | 2-methylphenyl |
| 3 | 3-methylphenyl |
| 4 | 4-methylphenyl |
| 5 | 2-chlorophenyl |
| 6 | 3-chlorophenyl |
| 7 | 4-chlorophenyl |
| 8 | 2-methoxyphenyl |
| 9 | 3-methoxyphenyl |
| 10 | 4-methoxyphenyl |
| 11 | 2,4-dimethylphenyl |
| 12 | 3,4-dimethylphenyl |
| 13 | 2,4-dichlorophenyl |
| 14 | 3,4-dichlorophenyl |
| 15 | 4-tert-butylphenyl |
| 16 | 3-bromophenyl |
| 17 | 4-bromophenyl |
| 18 | 2-fluorophenyl |
| 19 | 3-fluorophenyl |
| 20 | 4-fluorophenyl |
| 21 | 4-ethylphenyl |
| 22 | 3-isopropylphenyl |
| 23 | 2-trifluoromethylphenyl |
| 24 | 3-trifluoromethylphenyl |
| 25 | 4-trifluoromethylphenyl |

TABLE 2

| Compound | R¹ |
|---|---|
| 26 | 3-acetylphenyl |
| 27 | 4-acetylphenyl |
| 28 | 3-acetoaminophenyl |
| 29 | methyl |
| 30 | formyl |
| 31 | acetyl |
| 32 | butyl |
| 33 | tert-butyl |
| 34 | hexyl |
| 35 | cyclohexyl |
| 36 | cyano |
| 37 | chloromethyl |
| 38 | bromomethyl |
| 39 | chloro |
| 40 | bromo |
| 41 | iodo |
| 42 | nitoro |
| 43 | amino |
| 44 | vinyl |
| 45 | 2-methylpropenyl |
| 46 | 1,2-dimethylpropenyl |
| 47 | (E)-1-methylpropenyl |
| 48 | methoxycarbonyl |

TABLE 2-continued

| Compound | R¹ |
|---|---|
| 49 | 1-pentenyl |
| 50 | 1-heptenyl |

TABLE 3

| Compound | R¹ |
|---|---|
| 51 | 1-octenyl |
| 52 | 3-phenylpropenyl |
| 53 | benzyl |
| 54 | styryl |
| 55 | phenoxy |
| 56 | phenylthio |
| 57 | 2-methylphenoxy |
| 58 | 3-methylphenoxy |
| 59 | 4-methylphenoxy |
| 60 | 2-ethylphenoxy |
| 61 | phenoxymethyl |
| 62 | phenylthiomethyl |
| 63 | benzyloxy |
| 64 | benzylthio |
| 65 | 2-methylphenylthio |
| 66 | 3-methylphenylthio |
| 67 | 4-methylphenylthio |
| 68 | 2-methylbenzyloxy |
| 69 | 3-methylbenzyloxy |
| 70 | 4-methylbenzyloxy |
| 71 | 2-methylbenzylthio |
| 72 | 3-methylbenzylthio |
| 73 | 4-methylbenzylthio |
| 74 | 2-chlorophenoxy |
| 75 | 3-chlorophenoxy |

TABLE 4

| Compound | R¹ |
|---|---|
| 76 | 4-chlorophenoxy |
| 77 | 2-chlorophenylthio |
| 78 | 3-chlorophenylthio |
| 79 | 4-chlorophenylthio |
| 80 | 2-methoxyphenylthio |
| 81 | 3-methoxyphenylthio |
| 82 | 4-methoxyphenylthio |
| 83 | phenoxymethyl |
| 84 | 2-methylphenoxymethyl |
| 85 | 3-methylphenoxymethyl |
| 86 | 4-methylphenoxymethyl |
| 87 | 3,3-diethylpropynyl |
| 88 | 2-(trimethylsilyl)ethynyl |
| 89 | 2-(cyclohexyl)ethynyl |
| 90 | 3,3-dimethyl3-phenoxypropenyl |
| 91 | hydroxymethyl |
| 92 | 4-nitrophenyl |
| 93 | 4-cyanophenyl |
| 94 | 3-cyanophenyl |
| 95 | 2-cyanophenyl |
| 96 | 4-ethoxyphenyl |
| 97 | 4-phenoxyphenyl |
| 98 | 3-phenoxyphenyl |
| 99 | 4-trifluoromethoxyphenyl |
| 100 | hydroxy |

TABLE 5

| Compound | R¹ |
|---|---|
| 101 | 2-pyridyl |
| 102 | 3-pyridyl |
| 103 | 4-pyridyl |
| 104 | 2-thienyl |

TABLE 5-continued

| Compound | R¹ |
|---|---|
| 105 | 3-thienyl |
| 106 | 2-furyl |
| 107 | 3-furyl |
| 108 | 2-benzothienyl |
| 109 | 3-benzothienyl |
| 110 | 2-pyrimidinyl |
| 111 | 4-pyrimidinyl |
| 112 | 1-pyrazolyl |
| 113 | 2-thiazolyl |
| 114 | 5-oxazolyl |
| 115 | 2-quinolyl |
| 116 | pyrrol-1-yl |
| 117 | 6-methyl-2-pyridyl |
| 118 | 6-chloro-2-pyridyl |
| 119 | 3-chloro-2-pyridyl |
| 120 | 6-methoxy2-pyridyl |
| 121 | 5-methoxy2-pyridyl |
| 122 | 3-methyl2-pyridyl |
| 123 | benzothiazol-2-ylthio |
| 124 | 3-chloro-5-trifluoromethyl-2-pyridyl |
| 125 | 2-pyridyloxy |

TABLE 6

| Compound | R¹ |
|---|---|
| 126 | 3-chloro-5-trifluoromethyl-2-pyridyloxy |
| 127 | 5-trifluoromethyl-2-pyridyloxy |
| 128 | 4-pyrimidinyloxy |
| 129 | 2-pyrimidinyloxy |
| 130 | 6-chloro-4-pyrimidinyloxy |
| 131 | 5-chloro-2-pyridyloxy |
| 132 | allyloxy |
| 133 | propargyloxy |
| 134 | cyclopropylmethoxy |
| 135 | isopropoxy |
| 136 | tert-buthoxy |
| 137 | N-methylbenzylamino |
| 138 | 3-chloro-5-trifluoromethyl-2-pyridylamino |
| 139 | 5-trifluoromethyl-2-pyridylamino |
| 140 | 4-pyrimidinylthio |
| 141 | 2-pyrimidinylthio |
| 142 | 2-pyridylthio |
| 143 | 5-trifluoromethyl-2-pyridylthio |
| 144 | 3-chloro5-trifluoromethyl-2-pyridylthio |
| 145 | propylthio |
| 146 | tert-butylthio |
| 147 | 5-methoxy2-pyridylthio |
| 148 | propargylthio |
| 149 | cyclopropylmethylthio |
| 150 | 3,4-dimethylphenylthio |

TABLE 7

| Compound | R¹ |
|---|---|
| 151 | $CH_3ON=C(CH_3)$ |
| 152 | $C_2H_5ON=C(CH_3)$ |
| 153 | $CH_3CH_2CH_2ON=C(CH_3)$ |
| 154 | $(CH_3)_2CHON=C(CH_3)$ |
| 155 | $CH_3CH_2CH_2CH_2ON=C(CH_3)$ |
| 156 | $(CH_3)_2CHCH_2ON=C(CH_3)$ |
| 157 | $C_2H_5(CH_3)CHON=C(CH_3)$ |
| 158 | $CH_3CH_2CH_2CH_2CH_2ON=C(CH_3)$ |
| 159 | $CH_3CH_2CH_2CH_2CH_2CH_2ON=C(CH_3)$ |
| 160 | $(CH_3)_3CON=C(CH_3)$ |
| 161 | 1-(cyclopropylmethoxyimino)ethyl |
| 162 | 1-(cyclopentylmethoxyimino)ethyl |
| 163 | $(CH_3)_3CCH_2ON=C(CH_3)$ |
| 164 | $C_6H_5CH_2ON=C(CH_3)$ |
| 165 | $4-CH_3C_6H_4CH_2ON=C(CH_3)$ |
| 166 | $3-CH_3C_6H_4CH_2ON=C(CH_3)$ |

TABLE 7-continued

| Compound | R¹ |
|---|---|
| 167 | $2-CH_3C_6H_4CH_2ON=C(CH_3)$ |
| 168 | $3,4-(CH_3)_2C_6H_3CH_2ON=C(CH_3)$ |
| 169 | $2,5-(CH_3)_2C_6H_3CH_2ON=C(CH_3)$ |
| 170 | $2-ClC_6H_4CH_2ON=C(CH_3)$ |
| 171 | $3-ClC_6H_4CH_2ON=C(CH_3)$ |
| 172 | $4-ClC_6H_4CH_2ON=C(CH_3)$ |
| 173 | $3,4-Cl_2C_6H_3CH_2ON=C(CH_3)$ |
| 174 | $HC\equiv CCH_2ON=C(CH_3)$ |
| 175 | $H_2C=CCH_2ON=C(CH_3)$ |

TABLE 8

| Compound | R¹ |
|---|---|
| 176 | $CH_3OCH_2CH_2ON=C(CH_3)$ |
| 177 | $C_2H_5OCH_2CH_2ON=C(CH_3)$ |
| 178 | $C_6H_5CH_2CH_2ON=C(CH_3)$ |
| 179 | $2,4-Cl_2C_6H_3CH_2ON=C(CH_3)$ |
| 180 | $C_6H_5OCH_2CH_2ON=C(CH_3)$ |
| 181 | $C_6H_5O(CH_2)_3ON=C(CH_3)$ |
| 182 | $4-CH_3C_6H_4CH_2CH_2ON=C(CH_3)$ |
| 183 | $2-CH_3C_6H_4CH_2CH_2ON=C(CH_3)$ |
| 184 | $C_6H_5O(CH_2)_4ON=C(CH_3)$ |
| 185 | $4-CH_3C_6H_4OCH_2CH_2ON=C(CH_3)$ |
| 186 | $2-CH_3C_6H_4OCH_2CH_2ON=C(CH_3)$ |
| 187 | $4-ClC_6H_4CH_2CH_2ON=C(CH_3)$ |
| 188 | $2-ClC_6H_4CH_2CH_2ON=C(CH_3)$ |
| 189 | $4-CH_3C_6H_4CH(CH_3)ON=C(CH_3)$ |
| 190 | $2-CH_3C_6H_4CH(CH_3)ON=C(CH_3)$ |
| 191 | $C_6H_5CH(CH_3)ON=C(CH_3)$ |
| 192 | $4-(CH_3)_3CC_6H_4CH_2ON=C(CH_3)$ |
| 193 | $CH_3ON=C(CH_3)CH_2ON=C(CH_3)$ |
| 194 | $C_6H_5ON=C(CH_3)CH_2ON=C(CH_3)$ |
| 195 | $C_6H_5CH(CN)ON=C(CH_3)$ |
| 196 | $C_6H_5CH(CH_3O)ON=C(CH_3)$ |
| 197 | $C_6H_5C(=O)O$ |
| 198 | $HON=C(CH_3)$ |
| 199 | $C_6H_5CH_2ON=CH$ |
| 200 | 5-chloro-2-thienyl |

TABLE 9

| Compound | R¹ |
|---|---|
| 201 | $CH_3SC(CH_3)=N$ |
| 202 | $CH_3C(=S)NH$ |
| 203 | cyclopropyl-C(=S)NH |
| 204 | $CH_3(CH_2)_3SC(CH_3)=N$ |
| 205 | $CH_3SC(C_2H_5)=N$ |
| 206 | $CH_3SC(CH_3CH_2CH_2)=N$ |
| 207 | $CH_3SC(cyclopropyl)=N$ |
| 208 | $C_6H_5CH_2SC(CH_3)=N$ |
| 209 | $C_6H_5CH_2SC(C_2H_5)=N$ |
| 210 | $C_2H_5SC(C_6H_5)=N$ |
| 211 | $CH_3SC(SCH_3)=N$ |
| 212 | $C_6H_5SC(SCH_3)=N$ |
| 213 | $C_6H_5CH_2SC(SCH_3)=N$ |
| 214 | $C_2H_5SC(SC_2H_5)=N$ |
| 215 | $C_6H_5CH_2SC(SC_2H_5)=N$ |
| 216 | $CH_3SC(=S)NH$ |
| 217 | $C_6H_5CH_2SC(=S)NH$ |
| 218 | $4-CH_3C_6H_4CH_2SC(cyclopropyl)=N$ |
| 219 | $CH_3SC(cyclopentyl)=N$ |
| 220 | $CH_3SC(cyclohexyl)=N$ |
| 221 | $4-CH_3OC_6H_4CH_2SC(cyclopropyl)=N$ |
| 222 | $4-ClC_6H_4CH_2SC(cyclopropyl)=N$ |
| 223 | $C_6H_5CH_2SC(cyclopentyl)=N$ |
| 224 | $4-CH_3C_6H_4CH_2SC(CH_3)=N$ |
| 225 | $4-ClC_6H_4CH_2SC(CH_3)=N$ |

TABLE 10

| Compound | R$^1$ |
|---|---|
| 226 | 4-CH$_3$OC$_6$H$_4$CH$_2$SC(CH$_3$)=N |
| 227 | CH$_3$CH$_2$CH$_2$SC(C$_6$H$_5$)=N |
| 228 | (CH$_3$)$_2$CHCH$_2$SC(CH$_3$)=N |
| 229 | C$_6$H$_5$CH$_2$SC(cyclopropyl)=N |
| 230 | 4-CH$_3$OC$_6$H$_4$CH$_2$SC(SCH$_3$)=N |
| 231 | 4-ClC$_6$H$_4$CH$_2$SC(SCH$_3$)=N |
| 232 | 4-CH$_3$C$_6$H$_4$CH$_2$SC(SCH$_3$)=N |
| 233 | 4-CF$_3$C$_6$H$_4$CH$_2$SC(SCH$_3$)=N |
| 234 | 4-CF$_3$OC$_6$H$_4$CH$_2$SC(SCH$_3$)=N |
| 235 | CH$_3$CH$_2$CH$_2$SC(SCH$_3$)=N |
| 236 | 4-ClC$_6$H$_4$CH$_2$SC(=S)NH |
| 237 | 4-CH$_3$C$_6$H$_4$CH$_2$SC(=S)NH |
| 238 | 4-CF$_3$C$_6$H$_4$CH$_2$SC(=S)NH |
| 239 | 2-CH$_3$C$_6$H$_4$CH$_2$SC(SCH$_3$)=N |
| 240 | 4-C$_2$H$_5$C$_6$H$_4$CH$_2$SC(SCH$_3$)=N |
| 241 | 4-ClC$_6$H$_4$CH$_2$SC(S-cyclopropyl)=N |
| 242 | 4-CH$_3$C$_6$H$_4$CH$_2$SC(S-cyclopropyl)=N |
| 243 | 4-CF$_3$C$_6$H$_4$CH$_2$SC(S-cyclopropyl)=N |
| 244 | 4-CF$_3$OC$_6$H$_4$CH$_2$SC(S-cyclopropyl)=N |
| 245 | 4-CH$_3$OC$_6$H$_4$CH$_2$SC(S-cyclopropyl)=N |
| 246 | CH$_3$OCH$_2$CH=C(CH$_3$) |
| 247 | C$_2$H$_5$OCH$_2$CH=C(CH$_3$) |
| 248 | C$_6$H$_5$CH=C(CH$_3$) |
| 249 | C$_6$H$_5$CH$_2$OCH=C(CH$_3$) |
| 250 | 4-CH$_3$C$_6$H$_5$CH$_2$OCH=C(CH$_3$) |

TABLE 11

| Compound | R$^1$ |
|---|---|
| 251 | (C$_2$H$_5$)$_3$SiC≡C |
| 252 | [(CH$_3$)$_2$CH]$_3$SiC≡C |
| 253 | (CH$_3$)$_3$CSi(CH$_3$)$_2$C≡C |
| 254 | C$_2$H$_5$Si(CH$_3$)$_2$C≡C |
| 255 | (CH$_3$)$_2$CHSi(CH$_3$)$_2$C≡C |
| 256 | CH$_3$Si(C$_2$H$_5$)$_2$C≡C |
| 257 | (CH$_3$)$_3$CHSi(C$_2$H$_5$)$_2$C≡C |
| 258 | cyclo-C$_3$H$_5$C≡C |
| 259 | cyclopentylC≡C |
| 260 | 2-ClC$_6$H$_4$OC(CH$_3$)$_2$C≡C |
| 261 | 3-ClC$_6$H$_4$OC(CH$_3$)$_2$C≡C |
| 262 | 4-ClC$_6$H$_4$OC(CH$_3$)$_2$C≡C |
| 263 | 2-CH$_3$C$_6$H$_4$OC(CH$_3$)$_2$C≡C |
| 264 | 3-CH$_3$C$_6$H$_4$OC(CH$_3$)$_2$C≡C |
| 265 | 4-CH$_3$C$_6$H$_4$OC(CH$_3$)$_2$C≡C |
| 266 | 2-CH$_3$OC$_6$H$_4$OC(CH$_3$)$_2$C≡C |
| 267 | 3-CH$_3$OC$_6$H$_4$OC(CH$_3$)$_2$C≡C |
| 268 | 4-CH$_3$OC$_6$H$_4$OC(CH$_3$)$_2$C≡C |
| 269 | C$_2$H$_5$C(CH$_3$)$_2$C≡C |
| 270 | CH$_3$CH$_2$CH$_2$C(CH$_3$)$_2$C≡C |
| 271 | (CH$_3$)$_2$CHC(CH$_3$)$_2$C≡C |
| 272 | CH$_3$CH$_2$CH$_2$CH$_2$C(CH$_3$)$_2$C≡C |
| 273 | (CH$_3$)$_2$CHCH$_2$C(CH$_3$)$_2$C≡C |
| 274 | C$_2$H$_5$CH(CH$_3$)C(CH$_3$)$_2$C≡C |
| 275 | CH$_3$CH$_2$CH$_2$CH$_2$CH$_2$C(CH$_3$)$_2$C≡C |

TABLE 12

| Compound | R$^1$ |
|---|---|
| 276 | CH$_3$C(C$_2$H$_5$)$_2$C≡C |
| 277 | CH$_3$OC(C$_2$H$_5$)$_2$C≡C |
| 278 | C$_2$H$_5$OC(C$_2$H$_5$)$_2$C≡C |
| 279 | C$_6$H$_5$C(CH$_3$)$_2$C≡C |
| 280 | 2-CH$_3$C$_6$H$_4$C(CH$_3$)$_2$C≡C |
| 281 | 3-CH$_3$C$_6$H$_4$C(CH$_3$)$_2$C≡C |
| 282 | 4-CH$_3$C$_6$H$_4$C(CH$_3$)$_2$C≡C |
| 283 | 2-ClC$_6$H$_4$C(CH$_3$)$_2$C≡C |
| 284 | 3-ClC$_6$H$_4$C(CH$_3$)$_2$C≡C |
| 285 | 4-ClC$_6$H$_4$C(CH$_3$)$_2$C≡C |
| 286 | C$_6$H$_5$C≡C |
| 287 | 2-CH$_3$C$_6$H$_4$C≡C |

TABLE 12-continued

| Compound | R$^1$ |
|---|---|
| 288 | 2-ClC$_6$H$_4$C≡C |
| 289 | 2-CH$_3$OC$_6$H$_4$C≡C |
| 290 | HOC(CH$_3$)$_2$C≡C |
| 291 | C$_6$H$_5$CH$_2$C≡C |
| 292 | C$_6$H$_5$(CH$_2$)$_2$C≡C |
| 293 | C$_6$H$_5$(CH$_2$)$_3$C≡C |
| 294 | (CH$_3$)$_3$CC≡C |
| 295 | (CH$_3$)$_3$SiCH$_2$C≡C |
| 296 | (C$_2$H$_5$)$_3$SiCH$_2$C≡C |
| 297 | 1-hexynyl |
| 298 | C$_2$H$_5$OSi(CH$_3$)$_2$C≡C |
| 299 | 4-methyl1-pentynyl |
| 300 | 3-methyl1-pentynyl |

TABLE 13

| Compound | R$^1$ |
|---|---|
| 301 | C$_6$H$_5$Si(CH$_3$)$_2$CH$_2$ON=C(CH$_3$) |
| 302 | 4-CH$_3$C$_6$H$_4$Si(CH$_3$)$_2$CH$_2$ON=C(CH$_3$) |
| 303 | 2-CH$_3$OC$_6$H$_4$Si(CH$_3$)$_2$CH$_2$ON=C(CH$_3$) |
| 304 | 2-ClOC$_6$H$_4$Si(CH$_3$)$_2$CH$_2$ON=C(CH$_3$) |
| 305 | C$_6$H$_5$(CH$_2$)$_2$Si(CH$_3$)$_2$CH$_2$ON=C(CH$_3$) |
| 306 | CH$_3$COOC(CH$_3$)$_2$C≡C |
| 307 | 1-cyclohexenyl |
| 308 | 3-methyl-1-cyclohexenyl |
| 309 | CH$_3$O(CH$_2$)$_5$C≡C |
| 310 | C$_2$H$_5$O(CH$_2$)$_5$C≡C |
| 311 | CH$_3$O(CH$_2$)$_4$C≡C |
| 312 | C$_2$H$_5$O(CH$_2$)$_4$C≡C |
| 313 | CH$_3$O(CH$_2$)$_3$C≡C |
| 314 | C$_2$H$_5$O(CH$_2$)$_3$C≡C |
| 315 | cyclo-C$_3$H$_5$O(CH$_2$)$_3$C≡C |
| 316 | cyclo-C$_3$H$_5$C(CH$_3$O)C≡C |
| 317 | cyclo-C$_3$H$_5$C(CH$_3$)(C$_2$H$_5$O)C≡C |
| 318 | cyclo-C$_3$H$_5$OC(CH$_3$)(cyclo-C$_3$H$_5$)C≡C |
| 319 | C$_2$H$_5$C(CH$_3$)(CH$_3$O)C≡C |
| 320 | C$_2$H$_5$C(CH$_3$)(C$_2$H$_5$O)C≡C |
| 321 | cyclo-C$_3$H$_5$OC(CH$_3$)(C$_2$H$_5$)C≡C |
| 322 | cyclo-C$_3$H$_5$OC(CH$_3$)$_2$C≡C |
| 323 | 3-NO$_2$C$_6$H$_5$ |
| 324 | 4-NO$_2$C$_6$H$_5$ |
| 325 | 3-(CH$_3$)$_2$CHOC$_6$H$_5$ |

TABLE 14

| Compound | R$^1$ |
|---|---|
| 326 | (CH$_3$)$_2$C(CH$_3$O)C≡C |
| 327 | cyclo-C$_4$H$_7$C≡C |
| 328 | 2-cyclopentyl-2-methyl-1-ethynyl |
| 329 | 6-trifluoromethyl-2-pyridyl |
| 330 | 6-phenoxy-2-pyridyl |
| 331 | 6-benzyloxy-2-pyridyl |
| 332 | 6-ethyl-2-pyridyl |
| 333 | 6-propyl-2-pyridyl |
| 334 | 6-isopropyl-2-pyridyl |
| 335 | 6-butyl-2-pyridyl |
| 336 | 6-isobutyl-2-pyridyl |
| 337 | 6-sec-butyl-2-pyridyl |
| 338 | 6-tert-butyl-2-pyridyl |
| 339 | 2-cyclopentyl-2-ethyl-1-ethynyl |
| 340 | 4-phenyl2-pyrimidinyl |
| 341 | 4-phenoxy2-pyrimidinyl |
| 342 | 4-benzyloxy-2-pyrimidinyl |
| 343 | 4-methyl-2-pyrimidinyl |
| 344 | 4-ethyl-2-pyrimidinyl |
| 345 | 4-trifluoromethyl-2-pyrimidinyl |
| 346 | 4-methoxy2-pyrimidinyl |
| 347 | 4-cyano-2-pyrimidinyl |

TABLE 14-continued

| Compound | R¹ |
|---|---|
| 348 | 4-propyl-2-pyrimidinyl |
| 349 | 4-isopropyl-2-pyrimidinyl |
| 350 | 4-sec-butyl2-pyrimidinyl |

TABLE 15

| Compound | R¹ |
|---|---|
| 351 | 4-butyl-2-pyrimidinyl |
| 352 | 4-isobutyl-2-pyrimidinyl |
| 353 | 4-tert-butyl-2-pyrimidinyl |
| 354 | 4-pentyl-2-pyrimidinyl |
| 355 | 4-hexyl-2-pyrimidinyl |
| 356 | 4-cyclopropyl-2-pyrimidinyl |
| 357 | 6-methyl-4-pyrimidinyl |
| 358 | 6-ethyl-4-pyrimidinyl |
| 359 | 6-propyl-4-pyrimidinyl |
| 360 | 6-isopropyl-4-pyrimidinyl |
| 361 | 6-butyl-4-pyrimidinyl |
| 362 | 6-methoxy-4-pyrimidinyl |
| 363 | 6-phenoxy-4-pyrimidinyl |
| 364 | 6-benzyloxy-4-pyrimidinyl |
| 365 | 6-ethoxy-4-pyrimidinyl |
| 366 | 6-propoxy-4-pyrimidinyl |
| 367 | 6-pentyl-2-pyridyl |
| 368 | 6-hexyl-2-pyridyl |
| 369 | 2-pyrazinyl |
| 370 | 6-methyl-2-pyrazinyl |
| 371 | 6-ethyl-2-pyrazinyl |
| 372 | 6-propyl-2-pyrazinyl |
| 373 | 6-butyl-2-pyrazinyl |
| 374 | 6-phenoxy-2-pyrazinyl |
| 375 | 6-benzyloxy-2-pyrazinyl |

The compound of the invention of the formula [I-b] (Table 16 to 17)

TABLE 16

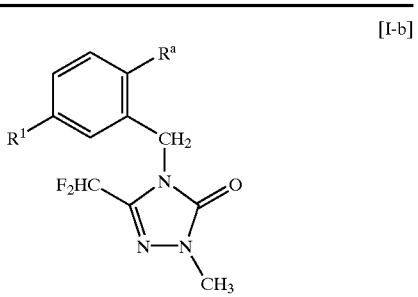

[I-b]

| Compound | R¹ | Rᵃ |
|---|---|---|
| 376 | phenyl | F |
| 377 | phenyl | Cl |
| 378 | phenyl | CF₃ |
| 379 | 4-chlorophenyl | F |
| 380 | 4-chlorophenyl | Cl |
| 381 | 4-chlorophenyl | CF₃ |
| 382 | (CH₃)₃CC≡C | F |
| 383 | (CH₃)₃CC≡C | Cl |
| 384 | (CH₃)₃CC≡C | CF₃ |
| 385 | 2-methylphenoxy | Cl |
| 386 | 3-methylphenoxy | Cl |
| 387 | 4-methylphenoxy | Cl |
| 388 | 2-methylphenoxymethyl | Cl |
| 389 | 3-methylphenoxymethyl | Cl |
| 390 | 4-methylphenoxymethyl | Cl |

TABLE 16-continued

[I-b]

| Compound | R¹ | Rᵃ |
|---|---|---|
| 391 | 2-methylbenzyloxy | Cl |
| 392 | 3-methylbenzyloxy | Cl |
| 393 | 4-methylbenzyloxy | Cl |
| 394 | 2-pyrazinyl | Cl |
| 395 | 2-pyrimidinyl | Cl |
| 396 | 4-pyrimidinyl | Cl |
| 397 | 1-pyrazolyl | Cl |
| 398 | CH₃ON=C(CH₃) | Cl |
| 399 | C₂H₅ON=C(CH₃) | Cl |
| 400 | 6-benzyloxy-2-pyrazinyl | Cl |

TABLE 17

| Compound | R¹ | Rᵃ |
|---|---|---|
| 401 | 4-CH₃C₆H₄CH₂ON=C(CH₃) | Cl |
| 402 | 3-CH₃C₆H₄CH₂ON=C(CH₃) | Cl |
| 403 | 2-CH₃C₆H₄CH₂ON=C(CH₃) | Cl |
| 404 | 3,4-(CH₃)₂C₆H₄CH₂ON=C(CH₃) | Cl |
| 405 | 2,5-(CH₃)₂C₆H₄CH₂ON=C(CH₃) | Cl |
| 406 | 6-trifluoromethyl-2-pyridyl | Cl |
| 407 | 6-phenoxy-2-pyridyl | Cl |
| 408 | 6-benzyloxy-2-pyridyl | Cl |
| 409 | 6-ethyl-2-pyridyl | Cl |
| 410 | 6-propyl-2-pyridyl | Cl |
| 411 | 6-isopropyl-2-pyridyl | Cl |
| 412 | 6-butyl-2-pyridyl | Cl |
| 413 | 6-isobutyl-2-pyridyl | Cl |
| 414 | 6-sec-butyl-2-pyridyl | Cl |
| 415 | 6-tert-butyl-2-pyridyl | Cl |
| 416 | 4-methyl-2-pyrimidinyl | Cl |
| 417 | 4-ethyl-2-pyrimidinyl | Cl |
| 418 | 4-trifluoromethyl-2-pyrimidinyl | Cl |
| 419 | 4-methoxy-2-pyrimidinyl | Cl |
| 420 | 6-methyl-2-pyrazinyl | Cl |
| 421 | 6-ethyl-2-pyrazinyl | Cl |
| 422 | 6-propyl-2-pyrazinyl | Cl |
| 423 | 6-butyl-2-pyrazinyl | Cl |
| 424 | 6-phenoxy-2-pyrazinyl | Cl |
| 425 | 6-benzyloxy-2-pyrazinyl | Cl |

The compound of the invention of formula [I-c] (Table 18)

TABLE 18

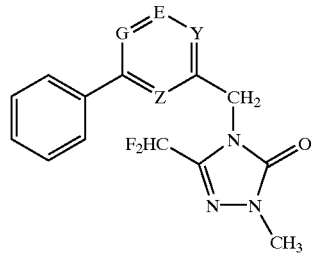

[I-c]

| Compound | Y | E | G | Z |
|---|---|---|---|---|
| 426 | CH | CH | CH | N |
| 427 | CH | CH | N | CH |
| 428 | CH | N | CH | CH |
| 429 | N | CH | CH | CH |
| 430 | CCH$_3$ | CH | CH | N |
| 431 | CCH$_3$ | CH | N | CH |
| 432 | CCH$_3$ | N | CH | CH |
| 433 | CH | CH | N | N |
| 434 | CH | N | CH | N |
| 435 | N | CH | CH | N |
| 436 | N | CH | N | CH |
| 437 | CH | N | N | CH |
| 438 | CCH$_3$ | CH | N | N |

Next, examples of the formulation are shown. In these examples, "part(s)" represents "part(s) by weight", the compounds of the invention are represented by Compound Numbers in Table 1 to 18.

Formulation Example 1 fifty (50) parts of each of the Compounds 1 to 438, 3 parts of calcium liqninunsulfonate, 2 parts of sodium laurylsulfate, and 45 parts of synthetic hydrated silica are well pulverized and mixed, to separately obtain wettable powders of each compound.

Formulation Example 2

Twenty (20) parts of each of the Compounds 1 to 438, 1.5 parts of sorbitan trioleate and 28.5 parts of an aqueous solution including 2 parts of polyvinyl alcohol are well mixed and wet pulverized. Then 40 parts of anaqueous solution including 0.05 part of xanthan gum and 0.1 part of aluminum magnesium silicate are added to the mixture, and 10 parts of propylene glycol are added, and the mixture is well mixed to give separately a flowable of each compound.

Formulation Example 3

Two (2) parts of each of the Compounds 1 to 438, 88 parts of kaolinite clay and 10 parts of talc are well pulverized and mixed to give separately a dust formulation of each compound.

Formulation Example 4

Five (5) parts of each of the Compounds 1 to 438, 14 parts of polyoxyethylenestyryl phenyl ether, 6 parts of calcium dodecylbenzenesulfonate, and 75 parts of xylene are well mixed to give separately an emulsifiable concentrates of each compound.

Formulation Example 5

Two (2) parts of each of the Compounds 1 to 438, 1 part of synthetic hydrated silicon oxide, 2 parts of calcium lignin sulfonate, 30 parts of bentonite, and 63.5 parts of kaolinite clay are well pulverized, and water is added Then the mixture is well kneaded and granulated and dried to give separately a granule of each compound.

Formulation Example 6

Ten (10) parts of each of the Compounds 1 to 438, 35 parts of white carbons including 50% of ammonium polyoxyethlenealkylethersulfate salts and 55 parts of water are well mixed and wet pulverized to give separately a flowable of each compound.

Formulation Example 7

Ten (10) parts of each of the Compounds 1 to 438, 5 parts of Sorpol 1200 (surfactant produced by Toho Chemical Co., Ltd.), 47 parts of dimethylsulfoxide and 38 parts of xylene are well mixed to give separately an emulsifiable concentrates of each compound.

Next, usefulness of the compounds of the invention as an active ingredient of an agricultural and horticultural fungicidal composition is shown by Test Examples.

Test Examples 1 to 6 are tests using a large amount (about 2000 L/ha) of spray on plants, and the extent of spraying is so that the whole surface of a plant body is completely wet and the sprayed liquid drips.

Test Examples 7 and 8 are tests using a small amount (corresponding 200 L/ha) of spray on plants, in which fine small liquid drops of a spray are uniformly adhere to the surface of a plant body and the extent of spraying is insufficient to for complete wetting of the surface of a plant body.

Controlling on a wheat disease in a field is so conducted in some cases that the spray liquid amount is about 200 L/ha. In this case, the amount of the sprayed liquid is insufficient for wetting of the whole plant body, and the sprayed liquid is adheres on a plant as fine liquid drops. For exerting high control effect on the subject diseases even under such spray condition, suitable physicochemical properties such as permeation transfer property, volatility and the like are required in addition to a basic effect.

In the following tests, compounds of the invention are represented by compound numbers described in Tables 1 to 8. The control effect of a compound of the invention was evaluated by visually observing the area of a lesion on a sample plant in investigation and comparing the area of a lesion in a non-treatment district and the area of a lesion in a districts treated with the compound of the invention.

Test Example 1

*Pyricularia oryzae* Control Test

Sand loam was compacted in a plastic pot, a rice (NIHONBARE) was seeded and grown in a green house for 20 days. Then, the Compounds 1, 3, 4, 6, 7, 9, 18, 19, 20, 24, 47, 104, 105, 113, 117, 118, 120, 294, 326, 329, 343 and 345 were formulated into flowable formulations according the Formulation Example 6, then, diluted with water to provide given concentration, and these were sprayed onto stems and leaves so as to give sufficient adhesion on the surface of rice leaves. After spraying, the plant was air-dried, and a suspension of *Pyricularia oryzae* was inoculated by spraying. After inoculation, the plant was left for 6 days at 28° C. under high humidity, then, the control effect was checked.

As a result, the lesion areas on plants in the 500 ppm treatment districts and 200 ppm treatment districts using compound 1 of the invention were not more than 10% of the lesion area of a non-treatment district. The lesion areas on the plant in the 200 ppm treatment districts of the Compounds 3, 4, 6, 7, 9, 18, 19, 20, 24, 47, 104, 105, 113, 117, 118, 120, 294, 326, 329, 343 and 345 were not more than 10% of the lesion area of a non-treatment district.

Test Example 2

Erysiphe Graminis Control Test

Sand loam was compacted in a plastic pot, a wheat (NORIN No. 73) was seeded and grown in a green house for 10 days. Then, the Compounds 1, 3, 4, 6, 7, 9, 18, 19, 20, 24, 47, 104, 105, 113, 117, 118, 120, 277, 294, 326, 329, 343 and 345 were formulated into flowable formulations according the Formulation Example 6, then, diluted with water to provide given concentration, and these were sprayed onto stems and leaves so as to give sufficient adhesion on the surface of wheat leaves of wheat seedling carrying a spread second leaf. After spraying, the plant was air-dried, and one day after, Erysiphe graminis spores were inoculated by falling. After inoculation, the plant was placed under illumination at 23° C. for 7 days, then, the control effect was checked.

As a result, the lesion areas on plants in the 500 ppm treatment districts and 200 ppm treatment districts using compound 1 of the invention were not more than 10% of the lesion area of a non-treatment district. The lesion areas on the plant in the 200 ppm treatment districts of the Compounds 3, 4, 6, 7, 9, 18, 19, 20, 24, 47, 104, 105, 113, 117, 118, 120, 277, 294, 326, 329, 343 and 345 were not more than 10% of the lesion area of a non-treatment district.

Test Example 3

Puccinia Striiformis Control Test

Sand loam was compacted in a plastic pot, a wheat (NORIN No. 73) was seeded and grown in a green house for 10 days. Then, the Compounds 1, 3, 4, 6, 7, 9, 18, 19, 20, 24, 47, 104, 105, 113, 117, 118, 120, 277, 294, 326, 329, 343 and 345 were formulated into flowable formulations according the Formulation Example 6, then, diluted with water to provide given concentration, and these were sprayed onto stems and leaves so as to give sufficient adhesion on the surface of wheat leaves. After spraying, the plant was air-dried, and Erysiphe graminis spores were inoculated. After inoculation, the plant was first left for 1 day at 23° C. in dark high humidity atmosphere, then, further left for 6 days under illumination, then, the control effect was checked.

As a result, the lesion areas on plants in the 500 ppm treatment districts and 200 ppm treatment districts using compound 1 of the invention were not more than 10% of the lesion area of a non-treatment district. The lesion areas on the plant in the 200 ppm treatment districts of the Compounds 3, 4, 6, 7, 9, 18, 19, 20, 24, 47, 104, 105, 113, 117, 118, 120, 277, 294, 326, 329, 343 and 345 were not more than 10% of the lesion area of a non-treatment district.

Test Example 4

Leptosphaeria nodorum Control Test

Sand loam was compacted in a plastic pot, a wheat (NORIN No. 73) was seeded and grown in a green house for 10 days. Then, the Compounds 1, 3, 4, 6, 7, 9, 18, 19, 20, 24, 47, 104, 105, 113,118,120,277,329, 343 and 345 were formulated into flowable formulations according the Formulation Example 6, then, diluted with water to provide given concentration, and these were sprayed onto stems and leaves so as to give sufficient adhesion on the surface of wheat leaves. After spraying, the plant was air-dried, and a suspension of *Leptosphaeria nodorum* spores was inoculated by spraying. After inoculation, the plant was first left for 4 days at 15° C. in dark high humidity atmosphere, then, further left for 7 days under illumination, then, the control effect was checked.

As a result, the lesion areas on plants in the 500 ppm treatment districts and 200 ppm treatment districts using compound 1 of the invention were not more than 10% of the lesion area of a non-treatment district. The lesion areas on the plant in the 200 ppm treatment districts of the Compounds 3, 4, 6, 7, 9, 18, 19, 20, 24, 47, 104, 105, 113, 118, 120, 277, 329, 343 and 345 were not more than 10% of the lesion area of a non-treatment district.

Test Example 5

Plasmopara Viticola Control Effect Test

Sand loam was compacted in a plastic pot, a grape (Berry A) was seeded and grown in a green house for 40 days. Then, the Compounds 1, 3, 4, 6, 7, 9, 18, 19, 20, 24, 47, 104, 105, 113, 117, 118, 120,277,294, 326,329, 343 and 345 were formulated into flowable formulations according the Formulation Example 6, then, diluted with water to provide given concentration (200 ppm), and these were sprayed onto stems and leaves so as to give sufficient adhesion on the surface of wheat leaves. After spraying, the plant was air-dried, and a suspension of zoosporangiua of Plasmopara viticola was inoculated by spraying. After inoculation, the plant was first left for 1 day at 23° C. under high humidity, then, further left for 6 days at room temperature, then, the control effect was checked.

As a result, the lesion areas on plants in the treatment districts using the Compounds 1, 3, 4, 6, 7, 9, 18, 19, 20, 24, 47, 104, 105, 113, 117, 118, 120, 277, 294, 326, 329, 343 and 345 were not more than 10% of the lesion area of a non-treatment district.

Test Example 6

*Sphaerotheca fuliginea* Control Effect Test

Sand loam was compacted in a plastic pot, a cucumber (SAGAMI HANJIRO) was seeded and grown in a green house for 12 days. Then, the Compound 1 was formulated into flowable fomulation according the Formulation Example 6, then, diluted with water to provide given concentration (200 ppm), and this was sprayed onto stems and leaves so as to give sufficient adhesion on the surface of cucumber leaves. After spraying, the plant was air-dried, and *Sphaerotheca fuliginea* spores were inoculated. After inoculation, the plant was first left for 12 days at 23° C., then, the control effect was checked.

As a result, the lesion area on plants in the treatment district using the Compound 1 was not more than 10% of the lesion area of a non-treatment district.

Test Example 7

Erysiphe Graminis Control Effect Test

Sand loam was compacted in a plastic pot, a wheat (NORIN No. 73) was seeded and grown in a green house for 10 days. Then, the Compound 1 was fomulated into emulsifiable formulation according the Formulation Example 7, then, diluted with water to provide given concentration (1000 ppm), and this was sprayed onto stems and leaves at a spraying liquid amount corresponding to 200 L/ha over wheat seedling carrying a spread second leaf. After spraying, the plant was air-dried, and one day after, Erysiphe graminis spores were inoculated by falling. After inoculation, the plant was placed under illumination at 23° C. for 7 days, then, the control effect was checked.

As a result, no lesion was recognized at all in the treatment district using the Compound 1.

Test Example 8

Puccinia striiformis Control Test

Sand loam was compacted in a plastic pot, a wheat (NORIN No. 73) was seeded and grown in a green house for 10 days. Then, the Compound 1 was formulated into emulsifiable formulation according the Formulation Example 7, then, diluted with water to provide given concentration (1000 ppm), and this was sprayed onto stems and leaves at a spraying liquid amount corresponding to 200 L/ha over wheat seedling carrying a spread second leaf. After spraying, the plant was air-dried, and Puccinia striiformis spores were inoculated. After inoculation, the plant was placed in dark high humidity atmosphere at 23° C. for 1 day, further, for 6 days under illumination, then, the control effect was checked.

As a result, no lesion was recognized at all in the treatment district using the Compound 1.

INDUSTRIAL APPLICABILITY

The compound of the invention has a excellent fungicidal activity.

What is claimed is:
1. A triazolone compound of the formula [I]:

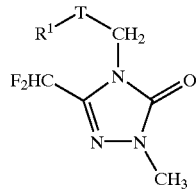

[I]

wherein,
R$^1$ represents A$^1$-L$^1$-, A$^1$-ON=CA$^2$—, A$^1$-ON=C(Me)CH$_2$ON=CA$^2$—, A$^1$-C(A$^2$)=N—OCH$_2$—, A$^1$S—C(A$^2$)=N—, A$^1$—C(=S)NH—, A$^1$S—C(=S)NH—, A$^1$S—C(SA$^2$)=N—, A$^1$-ON=C(CN)—, A$^1$-ON=C(Me)CH$_2$ON=C(CN)—, A$^1$—C(CN)=N—OCH$_2$—, halogen atom, nitro or cyano;
wherein, L$^1$ represents single bond, oxygen atom, sulfur atom, carbonyl, —OCH$_2$—, —SCH$_2$—, —C(=O)O—, —OC(=O)—, —C(=O)OCH$_2$—, —NH— or C$_1$–C$_6$ alkylimino;
A$^1$ and A$^2$, which are the same or different, represent hydrogen atom, C$_1$–C$_{10}$ alkyl, C$_2$–C$_{10}$ alkenyl, C$_2$–C$_{10}$ alkynyl, C$_3$–C$_{10}$ cycloalkyl, (C$_3$–C$_{10}$ cycloalkyl) C$_1$–C$_{10}$ alkyl, C$_5$–C$_{10}$ cycloalkenyl, (C$_5$–C$_{10}$ cycloalkenyl) C$_1$–C$_{10}$ alkyl, phenyl, naphthyl, phenyl C$_1$–C$_{10}$ alkyl, naphtyl C$_1$–C$_{10}$ alkyl, 5- or 6-membered heterocyclic group optionally condensed with a benzene ring, or methyl substituted by a 5- or 6-membered heterocyclic group optionally condensed with a benzene ring;
the alkyl, the alkenyl, the alkynyl, the cycloalkyl, the cycloalkylalkyl, the cycloalkenyl and the cycloalkenylalkyl, represented by A$^1$ and A$^2$, may optionally be each substituted by one or more substituents selected from the group consisting of halogen atom(s), cyano, nitro, C$_1$–C$_{10}$ alkoxy, C$_1$–C$_{10}$ haloalkoxy, C$_1$–C$_{10}$ alkylthio, C$_1$–C$_{10}$ haloalkylthio, (C$_1$–C$_9$ alkyl)carbonyl, (C$_1$–C$_9$ alkoxy) carbonyl, (C$_1$–C$_9$ alkyl)carbonylamino, phenyl, phenoxy, benzyloxy and tri(C$_1$–C$_{10}$ alkyl)silyl;
the phenyl, the naphthyl, the benzene ring in the phenylalkyl, the naphthalene ring in the phenylnaphthyl, the heterocyclic group, and the heterocyclic ring in the methyl substituted by a heterocylic group, represented by A$^1$ and A$^2$, may optionally be each substituted by one or more substituents selected from the group consisting of halogen atom(s), cyano, nitro, C$_1$–C$_{10}$ alkyl, C$_1$–C$_{10}$ haloalkyl, C$_3$–C$_{10}$ cycloalkyl, C$_1$–C$_{10}$ alkoxy, C$_1$–C$_{10}$ haloalkoxy, C$_1$–C$_{10}$ alkylthio, C$_1$–C$_{10}$ haloalkylthio, (C$_1$–C$_9$ alkyl)carbonyl, (C$_1$–C$_9$ alkoxy)carbonyl, (C$_1$–C$_9$ alkyl) carbonylamino, phenyl, phenoxy, benzyloxy, tri(C$_1$–C$_{10}$ alkyl)silyl, methylenedioxy and difluoromethylenedioxy;
with the proviso, when L$^1$ is single bond, A$^1$ is not a hydrogen atom;
T represents optionally substituted m-phenylene, optionally substituted m-azaphenylene or optionally substituted m-diazaphenylene bonded to R$^1$ and to CH$_2$ each via a carbon atom;
wherein the substituent(s) are one or more substituents selected from the group consisting of halogen atom(s), cyano, nitro, C$_1$–C$_6$ alkyl, C$_1$–C$_6$ haloalkyl, C$_1$–C$_6$ alkoxy, C$_1$–C$_6$ haloalkoxy, C$_1$–C$_6$ alkylthio, C$_1$–C$_6$ haloalkylthio and (C$_1$–C$_5$ alkoxy)carbonyl.
2. The triazolone compound according to claim 1, wherein
T is optionally substituted m-phenylene;
wherein the substituent(s) are one or more substituents selected from the group of halogen atom(s), cyano, nitro, C$_1$–C$_6$ alkyl, C$_1$–C$_6$ haloalkyl, C$_1$–C$_6$ alkoxy, C$_1$–C$_6$ haloalkoxy, C$_1$–C$_6$ alkylthio, C$_1$–C$_6$ haloalkylthio and (C$_1$–C$_5$ alkoxy)carbonyl.
3. The triazolone compound according to claim 1, wherein
T is optionally substituted m-azaphenylene or optionally substituted m-diazaphenylene bonded to R$^1$ and to CH$_2$ each via a carbon atom;
wherein the substituent(s) are one or more substituents selected from the group of halogen atom(s), cyano, nitro, C$_1$–C$_6$ alkyl, C$_1$–C$_6$ haloalkyl, C$_1$–C$_6$ alkoxy, C$_1$–C$_6$ haloalkoxy, C$_1$–C$_6$ alkylthio, C$_1$–C$_6$ haloalkylthio and (C$_1$–C$_5$ alkoxy)carbonyl.
4. The triazolone compound according to claim 1, wherein
T is optionally substituted m-phenylene;
wherein the substituent(s) are halogen atom(s) or methyl;
R$^1$ is optionally substituted phenyl;
wherein the substituent(s) are one or more substituents selected from the group consisting of halogen atom(s), cyano, nitro, C$_1$–C$_{10}$ alkyl, C$_1$–C$_{10}$ haloalkyl, C$_3$–C$_{10}$ cycloalkyl, C$_1$–C$_{10}$ alkoxy, C$_1$–C$_{10}$ haloalkoxy, C$_1$–C$_{10}$ alkylthio, C$_1$–C$_{10}$ haloalkylthio, ($C_1$–$C_9$ alkyl)carbonyl, ($C_1$–$C_9$ alkoxy)carbonyl, ($C_1$–$C_9$ alkyl)carbonylamino, phenyl, phenoxy, benzyloxy, tri($C_1$–$C_{10}$ alkyl)silyl, methylenedioxy and difluoromethylenedioxy.

5. The triazolone compound according to claim 1, which is represented by the formula [LX]:

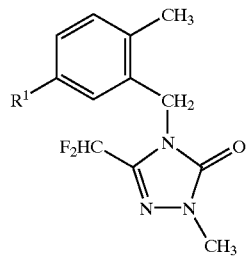

[LX]

wherein;

$R^1$ is optionally substituted phenyl;
wherein the substituent(s) are one or more substituents selected from the group consisting of halogen atom(s), cyano, nitro, $C_1$–$C_{10}$ alkyl, $C_1$–$C_{10}$ haloalkyl, $C_3$–$C_{10}$ cycloalkyl, $C_1$–$C_{10}$ alkoxy, $C_1$–$C_{10}$ haloalkoxy, $C_1$–$C_{10}$ alkylthio, $C_1$–$C_{10}$ haloalkylthio, ($C_1$–$C_9$ alkyl)carbonyl, ($C_1$–$C_9$ alkoxy)carbonyl, ($C_1$–$C_9$ alkyl)carbonylamino, phenyl, phenoxy, benzyloxy, tri($C_1$–$C_{10}$ alkyl)silyl, methylenedioxy and difluoromethylenedioxy.

6. 5-Difluoromethyl-2-methyl-4-(2-methyl-5-phenylbenzyl)-2,4-dihydro-3H-1,2,4-triazol-3-one; which is the triazolone compound according to claim 4, wherein $R^1$ is phenyl.

7. A fungicidal composition containing the triazolone compound according to claim 1 as an active ingredient, and an inactive carrier.

8. The fungicidal composition according to claim 7, which is containing 5-difluoromethyl-2-methyl-4-(2-methyl-5-phenylbenzyl)-2,4-dihydro-3H-1,2,4-triazol-3-one as an active ingredient, and an inactive carrier.

9. 5-Difluoromethyl-2-methyl-2,4-dihydro-3H-1,2,4-triazol-3-one of the formula [L]:

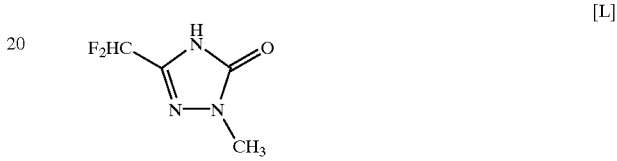

[L]

* * * * *